US010209240B2

(12) United States Patent
Smith et al.

(10) Patent No.: US 10,209,240 B2
(45) Date of Patent: Feb. 19, 2019

(54) PREDICTING HUMAN DEVELOPMENTAL TOXICITY OF PHARMACEUTICALS USING HUMAN STEM-LIKE CELLS AND METABOLOMIC RATIOS

(71) Applicant: STEMINA BIOMARKER DISCOVERY, INC., Madison, WI (US)

(72) Inventors: Alan Smith, Madison, WI (US); Paul West, Arena, WI (US); Jessica Palmer, Prairie du Sac, WI (US)

(73) Assignee: Stemina Biomarker Discovery, Inc., Madison, WI (US)

( * ) Notice: Subject to any disclaimer, the term of this patent is extended or adjusted under 35 U.S.C. 154(b) by 0 days.

(21) Appl. No.: 15/848,188

(22) Filed: Dec. 20, 2017

(65) Prior Publication Data

US 2018/0128814 A1 May 10, 2018

Related U.S. Application Data

(62) Division of application No. 14/439,723, filed as application No. PCT/US2013/067980 on Nov. 1, 2013.

(60) Provisional application No. 61/721,746, filed on Nov. 2, 2012, provisional application No. 61/827,407, filed on May 24, 2013.

(51) Int. Cl.
G01N 33/50 (2006.01)
G01N 33/68 (2006.01)

(52) U.S. Cl.
CPC ..... *G01N 33/5014* (2013.01); *G01N 33/5073* (2013.01); *G01N 33/6812* (2013.01); *G01N 33/6815* (2013.01)

(58) Field of Classification Search
None
See application file for complete search history.

(56) References Cited

U.S. PATENT DOCUMENTS

| | | | |
|---|---|---|---|
| 6,200,806 | B1 | 3/2001 | Thomson |
| 7,550,258 | B2 | 6/2009 | Kaddurah-Daouk et al. |
| 7,910,301 | B2 | 3/2011 | Kaddurah-Daouk et al. |
| 7,947,453 | B2 | 5/2011 | Kaddurah-Daouk et al. |
| 8,703,424 | B2 | 4/2014 | West et al. |
| 8,703,483 | B2 | 4/2014 | Cezar et al. |
| 2006/0258672 | A1 | 11/2006 | Barbosa et al. |
| 2007/0248947 | A1* | 10/2007 | Cezar ................ G01N 33/5038 435/4 |
| 2011/0312019 | A1 | 12/2011 | West et al. |
| 2012/0071543 | A1 | 3/2012 | Carter et al. |
| 2014/0027306 | A1 | 1/2014 | Whitemore |
| 2014/0255969 | A1 | 9/2014 | Cezar |

FOREIGN PATENT DOCUMENTS

WO WO 2011/119637 A1 9/2011

OTHER PUBLICATIONS

Abramovici et al., "Myeloschisis in a six weeks embryo of a leukemic woman treated with busulfan," *Teratology*, 2005; 18:241-245.
Accutane™ (isotretinoin), Product Monograph, 2014; Roche Laboratories, Nutley, New Jersey.
Adler et al., "First steps in establishing a developmental toxicity test method based on human embryonic stem cells," *Toxicology In vitro*, 2008; 22:200-211.
Afinitor® (everolimus), Highlights of Prescribing Information, February 016; Novartis Sverige AB, Taby, Sweden.
Agenerase® (Prescribing Information), 2005; GlaxoSmithKline, Research Triangle Park, NC.
Alexander et al., "Role of nitric oxide in chick embryonic organogenesis and dysmorphogenesis," *Birth Defects Research Part A: Clinical and Molecular Teratology*, 2007; 79:581-594.
Alpert, "Hydrophilic-interaction chromatography for the separation of peptides, nucleic acids, and other polar compounds," *Journal of Chromatography*, 1990; 499:177-196.
Altoprev® lovastatin extended-release tablets Description, accessed May 18, 2016 at: http://www.accessdata.fda.gov/drugsatfda_docs/label/2012/021316s029lbl.pdf.
Amoxil® (Full Prescribing Information), Dr. Reddy's Laboratories, Bridgewater, NJ; accessed May 18, 2016 at: http://www.accessdata.fda.gov/drugsatfda_docs/label/2011/050542s026s027s028,050754s013s014s017,050760s012s013s015,050761s012s013s015lbl.pdf.
Aquasol A® (Product Information), 2007, Mayne Pharma, Paramus, New Jersey.
Avandia® (Product Monograph), 2012, GlaxoSmithKline, Research Triangle Park, NC.
Baker et al., "Vitamin profile of 174 mothers and newborns at parturition," *Am J Clin Nutr.*, 1975; 28:56-65.
Barr et al., "Assessing human exposure to phthalates using monoesters and their oxidized metabolites as biomarkers," *Environmental Health Perspective*, 2003; 11:1148-1151.
Basketter et al., "A roadmap for the development of alternative (non-animal) methods for systemic toxicity testing," *ALTEX*, 2012; 29(1):3-91.
Beckman and Brent, "Mechanisms of teratogenesis," *Ann Rev Pharmacol*, 1984; 24:483-500.
Bhattacharya et al., "Toxicity testing in the 21 century: defining new risk assessment approaches based on perturbation of intracellular toxicity pathways," *PLoS One*, 2011; 6(6):e20887.
Bogdanov et al., "Metabolomic profiling to develop blood biomarkers for Parkinson's disease," *Brain*, 2008; 131: 389-396.
Brannen et al., "Development of a zebrafish embryo teratogenicity assay and quantitative prediction model," *Birth Defects Res B Devl Reprod Toxicol*, 2010; 89:66-67.

(Continued)

*Primary Examiner* — Thomas J. Visone
(74) *Attorney, Agent, or Firm* — Adam M. Schoen, Esq.; Brown Rudnick LLP

(57) ABSTRACT

This present invention provides rapid, reproducible, biomarker-based screening methods for the developmental toxicity testing of compounds. The methods are designed to identify the exposure level at which a test compound perturbs metabolism in a manner predictive of developmental toxicity. In particular, the perturbation of two metabolites, ornithine and cystine, is measured, wherein a ratio of the fold change in ornithine to the fold change in cystine of less than or equal to about 0.88 is indicative of the teratogenicity of a test compound.

15 Claims, 12 Drawing Sheets

(56) References Cited

OTHER PUBLICATIONS

Brent and Beckman, "Environmental teratogens," *Bull NY Acad Med*, 1990; 66:123-163.

Brent and Holmes, "Clinical and basic science from the thalidomide tragedy: what have we learned about the causes of limb defects?" *Teratology*, 1988; 38:241-251.

Brieman, "Random Forests," *Machine Learning*, 2001; 45: 5-32.

Brown, "Selection of test chemicals for the ECVAM international validation study on in vitro embryotoxicity tests. European Centre for the Validation of Alternative Methods," *Altern Lab Anim*, 2002; 30:177-198.

Busulfex® (busulfan) "Highlights of Prescribing Information," Jan. 2016, Otsuka America Pharmaceutical, Rockville, MD.

Caffeine—Patient Handout, Oct. 2015, accessed on May 18, 2016 at: http://reference.medscape.com/drug/cafcit-nodoz-caffeine-342995#91.

Caffeine—Pharmacology, accessed at on May 18, 2016 at: http://reference.medscape.com/drug/cafcit-nodoz-caffeine-342995#10.

Cezar and Donley, "Stemina Biomarker Discovery," *Regenerative Medicine*, 2008; 3(5):665-669.

Cezar et al., "Identification of small molecules from human embryonic stem cells using metabolomics," *Stem Cells and Development*, 2007; 16:869-882.

Chan and Lau, "Effect of rosiglitazone on embryonic growth and morphology: a study using a whole rat embryo culture model," *Fertil Steril*, 2006; 86:490-492.

Chapin et al., "State of the art in developmental toxicity screening methods and a way forward: a meeting report addressing embryonic stem cells, whole embryo culture, and zebrafish," *Birth Defects Research Part B: Developmental and Reproductive Toxicology*, 2008; 83:446-456.

Chaudhary et al., "Embryonic stem cells in predictive cardiotoxicity: laser capture microscopy enables assay development," *Toxicol Sci*, 2006; 90(1):149-58.

Clark, "Embryotoxicity of the artemisinin antimalarials and potential consequences for use in women in the first trimester," *Reprod Toxicol*, 2009; 28:285-296.

Claudio et al., "NIEHS investigates links between children, the environment, and neurotoxicity," *Environ Health Perspect*, 2001; 109:A258-A261.

Cole et al., "Phase II trial of oral aminopterin for adults and children with refractory acute leukemia," *Clin Cancer Res*, 2005; 11:8089-8096.

Comtan® (entacapone), Prescribing Information, Jul. 2014, Novartis Pharmaceuticals, East Hanover, NJ.

Cuprimine® (penicillamine), description, 1992, Merck, Whitehouse Station, NJ.

Depacon® (valproate sodium) Product Information, Jan. 2006, Abbott Laboratories, North Chicago, IL.

Department of Health and Human Services, Food and Drug Administration, "Content and Format of Labeling for Human Prescription Drug and Biological Products; Requirements for Pregnancy and Lactation Labeling," *Federal Register*, 2008; 73(104):30831-30868.

DevTOX Discovery Brochure 2016, accessed May 24, 2016 at: http://www.stemina.com/wp-content/uploads/2016/04/2016_Stemina_Folder_Insert_9_in_FINAL.pdf.

Dilantin® (phenytoin sodium capsule, extended release), Description, Apr. 2016; Pfizer, New York, NY.

DiLiberti et al., "The fetal valproate syndrome," *Am. J. Med. Genetic.*, 1984; 19:473-481.

Drewe et al., "Effect of intravenous infusions of thiamine on the disposition kinetics of thiamine and its pyrophosphate," *J Clin Pharm Ther*, 2003; 28:47-51.

Egnash et al., "A Biomarker Based Developmental Toxicity Screen Using Human Induced Pluripotent Stem Cells for Compound Prioritization," presented at the Society of Toxicology 53rd Annual Meeting, Mar. 23-27, 2014, in Phoenix, Arizona.

Egnash et al., "A Biomarker-Based Human Stem Cell Assay Applied for Ranking a Retinoid Series Based on Relative Developmental Toxicity Potential," presented at the Society of Toxicology's 55th Annual Meeting and ToxExpo, Mar. 22-24, 2015, in San Diego, California.

Egnash et al., "Toward Validation of a Human In Vitro Assay for Developmental Toxicity Assessment," poster presented at the 9th World Congress on Alternatives and Animal Use in the Life Sciences, Prague, Czech Republic, (Aug. 24-28, 2014.

Environmental Protective Agency (EPA), 1998, Chemical Hazard Data Availability Study, Office of Pollution Prevention and Toxins.

European Extended Search Report for Application No. 13850210.9-1408, dated May 3, 2016, 9 pages.

General Accounting Office (GAO), 1994, Toxic Substances Control Act: Preliminary Observations on Legislative Changes to Make TSCA More Effective, Testimony, Jul. 13, 1994, GAO/T-RCED-94-263.

Genschow et al., "Considering the Test Performance for Three Class Data Using Linear Discriminant Analysis: A Case Study", *Alternatives to Laboratory Animals*, 2004; 32:713-723.

Genschow et al., "Development of prediction models for three in vitro embryotoxicity tests in an ECVAM validation study," *In vitro Molecular Toxicology*, 2000; 13:51-66.

Genschow et al., "The ECVAM international validation study on in vitro embryotoxicity tests: results of the definitive phase and evaluation of prediction models, European Centre for the Validation of Alternative Methods," *Alternatives to Laboratory Animals*, 2002; 30:151-176.

Genschow et al., "Validation of the Embryonic Stem Cell Test in the International ECVAM Validation Study on Three in Vitro Embryotoxicity Tests," *Alternatives to Laboratory Animals*, 2004; 32:209-244.

Goodacre et al., "Metabolomics by numbers: acquiring and understanding global metabolite data," *Trends in Biotechnology*, 2004; 22:245-252.

Greaves et al., "First dose of potential new medicines to humans: how animals help," *Nat Rev Drug Discovery*, 2004; 3:226-236.

Gustafson et al., "Inter-laboratory assessment of a harmonized zebrafish developmental toxicology assay—progress report on phase I," *Reprod Toxicol*, 2012; 33:155-164.

Hansen, "Oxidative stress as a mechanism of teratogenesis," *Birth Defects Res C Embryo Today*, 2006; 78:293-307.

Hepsera® (adefovir dipivoxil), Highlights of Prescribing Information, 2012; Gilead Sciences, Foster City, CA.

Herrmann, "Teratogenic effects of retinoic acid and related substances on the early development of the zebrafish (*Brachydanio rerio*) as assessed by a novel scoring system," *Toxicol In Vitro*, 1995; 9:267-283.

Higuera et al., "Patterns of Amino Acid Metabolism by Proliferating Human Mesenchymal Stem Cells," *Tiss Eng. A.*, 2012; 18(5&6):654-664.

Hilbert et al., "Pharmacokinetics and dose proportionality of loratadine," *J Clin Pharmacol*, 1987; 27:694-698.

Hoyert et al., "Annual summary of vital statistics: 2004," *Pediatrics*, 2006; 117:168-183.

Huuskonen, "New models and molecular markers in evaluation of developmental toxicity," *Toxicology & Applied Pharm*, 2005; 207:S495-S500.

International Preliminary Report on Patentability for PCT/US2013/067980, issued by the International Bureau of WIPO dated May 14, 2015; 9 pgs.

International Search Report and Written Opinion for PCT/US2007/008923, issued by the International Bureau of WIPO dated Nov. 30, 2007, 9 pgs.

International Search Report and Written Opinion for PCT/US2013/067980, issued by the United States Patent Office dated Jan. 29, 2014; 11 pgs.

Isibashi et al., "Oxygen-induced embryopathy and the significance of glutathione-dependent antioxidant system in the rate embryo during early organogenesis," *Free Raid Biol Med*, 1997; 22:447-54.

Januvia® (sitagliptin) (Highlights of Prescribing Information), Apr. 2016; Merck, Whitehouse Station, New Jersey.

(56) References Cited

OTHER PUBLICATIONS

Jelovsek et al., "Prediction of risk for human developmental toxicity: how important are animal studies for hazard identification?," *Obset Gynecol*, 1989; 74:624-636.
Kalhan and Bier, "Protein and amino acid metabolism in the human newborn," *Annu Rev Nutr*, 2008; 28:389-410.
Karim et al., "Disposition kinetics and tolerance of escalating single doses of ramelteon, a high-affinity MT1 and MT2 melatonin receptor agonist indicated for treatment of insomnia," *J Clin Pharmacol.*, 2006; 46:140-148.
Kemper and Bauman, "Neuropathology of infantile autism," *Journal of Neuropathology and Experimental Neurology*, 1998; 57, 645-652.
Kind et al., "A comprehensive urinary metabolomic approach for identifying kidney cancer," *Analytical Biochemistry*, 2007; 363:185-195.
Kleinsteuer et al., "Identifying developmental toxicity pathways for a subset of ToxCast chemicals using human embryonic stem cells and metabolomics," *Toxicology and Applied Pharmacology*, 2011; 257:111-121.
Klug et al., "Effect of acyclovir on mammalian embryonic development in culture," *Arch Toxicol*, 1985; 58:89-96.
Klug et al., "Influence of 13-cis and all-trans retinoic acid on rat embryonic development in vitro: correlation with isomerisation and drug transfer to the embryo," *Arch Toxicol*, 1989; 63:185-192.
Knudsen et al., "Evaluation of 1066 Toxcast Chemicals in a Human Stem Cell Assay for Developmental Toxicity," Poster Board No. P651 presented at the 2016 Society of Toxicology Annual Meeting, New Orleans, LA, Mar. 16, 2016.
Knutson, "ToxCast Profiling in a Human Stem Cell Assay for Developmental Toxicity," presentation at the 2016 Society of Toxicology Annual Meeting, New Orleans, LA, Mar. 13-17, 2016.
Kovacic and Somanathan, "Mechanism of teratogenesis: electron transfer, reactive oxygen species, and antioxidants," *Birth Defects Res C Embryo Today*, 2006; 78:308-325.
Kuster and Mann, "Identifying proteins and post-translational modifications by mass spectrometry," *Curr Opin Struct Biol*, Jun. 1998; 8(3):393-400.
Laniazid (isoniazid), Product Information, Jun. 30, 2000; accessed at www.drugs.com/mmx/isoniazid.html on May 19, 2016.
Lankas et al., "The role of maternal toxicity in lovastatin-induced developmental toxicity," *Birth Defects Res B Dev Reprod Toxicol*, 2004; 71:111-123.
Lee and Juchau, "Dysmorphogenic effects of nitric oxide (NO) and NO-synthase inhibition: studies with intra-amniotic injections of sodium nitroprusside and N-monmethyl-L-arginine," *Teratology*, 2005; 49:452-464.
Leucuta et al., "Pharmacokinetic interaction study between ranitidine and metoclopramide," *Rom J Gastroenterol*, 2004; 13:211-214.
Levenstein et al., "Basic fibroblast growth factor support of human embryonic stem cell self-renewal," *Stem Cells*, 2005; 24:568-574.
Li et al., "Expansion of human embryonic stem cells in defined serum-free medium devoid of animal-derived products," *Biotechnol Bioeng*, 2005; 91(6):688-698.
Liaw and Weiner, "Classification and regression by random forest," *R News: The Newsletter of the R Project*, 2002; 2:18-22.
Liebelt et al., "NTP-CERHR expert panel report on the reproductive and developmental toxicity of hydroxyurea," *Birth Defects Res B Dev Reprod Toxicol*, 2007; 80:259-366.
Louisse et al., "Relative developmental toxicity potencies of retinoids in the embryonic stem cell test compared with their relative potencies in in vivo and two other in vitro assays for developmental toxicity," *Toxicol Lett*, 2011; 203:1-8.
Lu et al., "Nicotinamide N-methyl transferase (NNMT) gene polymorphisms and risk for spina bifida," *Birth Defects Research Part A: Clinical and Molecular Teratology*, 2008; 82(10):670-675.
Ludwig et al.,"Feeder-independent culture of human embryonic stem cells," *Nat Methods*, 2006; 3:637-646.
Lujan et al., "Glutamate and GABA receptor signaling in the developing brain," *Neuroscience*, 2005; 130:567-580.

Luna et al., "Doxylamine and diphenhydramine pharmacokinetics in women on low-dose estrogen oral contraceptives ," *J Clin Pharmacol*, 1989; 29:257-260.
Madureira et al., "The toxicity potential of pharmaceuticals found in the Douro River estuary (Portugal)—experimental assessment using a zebrafish embryo test," *Environ Toxicol Pharmacol*, 2011; 32:212-217.
Mahmood and Chamberlin, "A limited sampling method for the estimation of AUC and Cmax of carbamazepine and carbamazepine epoxide following a single and multiple dose of a sustained-release product," *Br J Clin Pharmacol*, 1998; 45:241-246.
Mao et al., "Retinoic acid regulates ornithine decarboxylase gene expression at the transcriptional level," *Biochem J*, 1993; 295;641-644.
Marx-Stoelting et al., "A review of the implementation of the embryonic stem cell test (EST). The report and recommendations of an ECVAM/ReProTect Workshop," *Alternatives to Laboratory Animals*, 2009; 37:313-328.
McGrath and Li, "Zebrafish: a predictive model for assessing drug-induced toxicity," *Drug Discov Today*, 2008; 13:394-401.
Miller and Stromland, "Teratogen update: Thalidomide: a review, with a focus on ocular findings and new potential uses," *Teratology*, 1999; 60:306-321.
Miller et al., "Pharmacokinetic profiles of artesunate following multiple intravenous doses of 2, 4, and 8 mg/kg in healthy volunteers: phase 1b study," *Malar J*, 2012; 11:255.
Muindi et al., "Clinical pharmacology of oral all-trans retinoic acid in patients with acute promyelocytic leukemia," *Cancer Res*, 1992; 52:2138-2142.
Nachmany et al., "Neural tube closure depends on nitric oxidase synthase activity," *J. Neurochem.*, 2006; 96:247-253.
National Research Council, *Scientific Frontiers in developmental toxicology and risk assessment*, The National Academies Press, Washington, D.C.; 2000. Cover page, title page and table of contents (24 pages).
Nelson et al., "Teratogenic effects of pantothenic acid deficiency in the rat," *J Nutr.*, 1957; 62:395-405.
Nieden et al., "Molecular markers in embryonic stem cells," *Toxicology in vitro*, 2001; 15:455-461.
Oman et al., "Phase I/II trial of intraperitoneal 5-Fluorouracil with and without intravenous vasopressin in non-resectable pancreas cancer," *Cancer Chemother Pharmacol*, 2005; 56:603-609.
Padayatty et al., "Vitamin C pharmacokinetics: implications for oral and intravenous use," *Ann Intern Med*, 2004; 140:533-537.
Palma-Aguirre et al., "Bioavailability of two oral suspension and two oral tablet formulations of acyclovir 400 mg: two single-dose, open-label, randomized, two-period crossover comparisons in healthy Mexican adult subjects," *Clin Ther*, 2007; 29:1146-1152.
Palmer et al., "Combination of a Human Pluripotent Stem Cell and Zebrafish Assay to Predict the Developmental Toxicity of Chemicals," Poster Board No. P651 presented at the 2016 Society of Toxicology Annual Meeting, New Orleans, LA, Mar. 16, 2016.
Palmer et al., "Development of a Targeted Biomarker Assay to Predict Developmental Toxicity Using Induced Pluripotent Stem Cells," Poster presented at the 34th American College of Toxicology Annual Conference, San Antonio, Texas, Nov. 4-5, 2013.
Palmer et al., "Establishment and Assessment of a New Human Embryonic Stem Cell Based Biomarker Assay for Developmental Toxicity Screening," *Birth Defects Res B Dev Reprod Toxicity*, 2013; 98(4):343-363.
Palmer et al., "Establishment and Assessment of a New Human Embryonic Stem Cell Based Biomarker Assay for Developmental Toxicity Screening," poster presented at the 11th International Conference on Environmental Mutagens in Foz do Iguassu, Brazil, Nov. 5, 2013.
Palmer et al., "Metabolic biomarkers of prenatal alcohol exposure in human embryonic stem cell-derived neural lineages," *Alcohol Clin Exp Res*, 2012; 36(8):1314-24.
Palmer et al., "Metabolomics Based Comparison of Human Embryonic and Induced Pluripotent Stem Cells to Predict Developmental Toxicity," presented at the Society of Toxicology's 51st Annual Meeting, Mar. 11-15, 2012, in San Francisco, California.

(56) References Cited

OTHER PUBLICATIONS

Paquette et al., "Assessment of the embryonic stem cell test and application and use in the pharmaceutical industry," *Birth Defects Research Part B: Developmental and Reproductive Toxicology*, 2008; 83:104-111.

Pearl and Bigson, "Clinical aspects of the disorder of GABA metabolism in children," *Current Opinion in Neurology*, 2004; 17:107-113.

Pearl et al., "The Pediatric neurotransmitter disorders," *Journal of Child Neurology*, 2007; 22:606-616.

Pegg, "Mammalian polyamine metabolism and function," *IUBMB Life*, 2009; 61:880-894.

Penicillin G Potassium Injection (Product Information), Aug. 2014; Baxter Healtcare, Deerfield, IL.

Piersma et al., "Interlaboratory evaluation of embryotoxicity in the postimplantation rat embryo culture," *Reprod Toxicol*, 1995; 9:275-280.

Piersma, "Validation of alternative methods for developmental toxicity testing," *Toxicology Letters*, 2004; 149:147-153.

Qu et al., "Validation of biomarkers in humans exposed to benzene: Urine metabolites," *American Journal of Industrial Medicine*, 2000; 37:522-531.

Ramirez et al., "Metabolomics in Toxicology and Preclinical Research," *ALTEX*, 2013; 30:209-225.

Repine et al., "Oxidative stress in chronic obstructive pulmonary disease," *American Journal of Respiratory and Critical Care Medicine*, 1997; 156(2):341-357.

Ritchie et al., "Effect of co-administration of retinoids on rat embryo development in vitro," *Birth Defects Res A Clin Mol Teratol*, 2003; 67:444-451.

Ritz and Streibig, *J Statistical Software*, 2005; 12:1-22.

Robinson et al., "Embryotoxicant-specific transcriptomic responses in rat postimplantation whole-embryo culture," *Toxicol Sci*, 2010; 118:675-685.

Rock et al., "Pantothenate kinase regulation of the intracellular concentration of coenzyme A," *The Journal of Biological Chemistry*, 2000; 275:1377-1383.

Rosano et al., "Infant mortality and congenital anomalies from 1950 to 1994: an international perspective," *J Epidemiol Community Health*, 2000; 54:660-666.

Sabatine et al., "Metabolomic identification of novel biomarkers of myocardial ischemia," *Circulation*, 2005; 112:3868-3875.

Sarafem® (fluoxetine hydrochloride tablet), Highlights of Prescribing Information, Oct. 2014; Warner Chilcott, Rockaway, NJ.

Scott et al., "Human induced pluripotent stem cells and their use in drug discovery for toxicity testing," *Toxicol Lett*, 2013; 219:49-58.

Sekowski et al., "Key Metabolic Pathway Changes in Human Embryonic Stem Cells Exposed to Methyl Parathion and Methyl Paraoxon," posted at https://www.stemina.com/news-publications/posters on Jan. 23, 2014. Accessed at www.stemina.com/key-metabolic-pathway-changes-in-human-embryonic-stem-cells-exposed-to-methyl-parathion-and-methyl-paraoxon on Aug. 30, 2017.

Selderslaghs et al., "Development of a screening assay to identify teratogenic and embryotoxic chemicals using the zebrafish embryo," *Reproductive Toxicology*, 2009; 28:308-320.

Selderslaghs et al., "Feasibility study of the zebrafish assay as an alternative method to screen for developmental toxicity and embryotoxicity using a training set of 27 compounds," *Reprod Toxicol*, 2012; 33:142-154.

Serkova et al., "Early detection of graft failure using the blood metabolic profile of a liver recipient," *Transplantation*, 2007; 83: 517-521.

Shanks et al., "Are animal models predictive for humans?" *Philosophy, Ethics, and Humanities in Medicine*, 2009; 4:2.

Shinka et al., "Effect of valproic acid on the urinary metabolic profile of a patient with succinic semialdehyde dehydrogenase deficiency," *J Chromatogr B Analyt Technol Biomed Life Sci*, 2003; 792:99-106.

Shoda et al., "Higher maximal serum concentration of methotrexate predicts the incidence of adverse reactions in Japanese rheumatoid arthritis patients," *Mod Rheumatol*, 2007; 17:311-316.

Simonian et al., "Oxidative stress in neurodegenerative diseases," *Annual Review of Pharmacology and Toxicology*, 1996; 36:83-106.

Smith et al., "XCMS: processing mass spectrometry data for metabolite profiling using nonlinear peak alignment, matching, and identification,"*Anal Chem*, 2006; 78:779-787.

Soga et al., "Differential metabolomics reveals ophthalmic acid as an oxidative stress biomarker indicating hepatic glutathione consumption," *J Biol Chem*, 2006; 281:16768-16778.

Spielmann et al., *In vitro Toxicology*, 1997; 10:119-127.

Sreekumar et al., "Metabolomic profiles delineate potential role for sarcosine in prostate cancer progression," *Nature*, 2009; 457: 910-914.

Stark et al., "Dysmorphogenesis elicited by microinjected acetaminophen analogs and metabolites in rat embryos cultured in vitro," *J Pharmacol Exp Ther*, 1990; 255:74-82.

Summar, M., "Current strategies for the management of neonatal urea cycle disorders," *J Pediatr*, 2001; 131:S30-S39.

Tan et al., "A novel melatonin metabolite, cyclic 3-hydroxymelatonin: a biomarker of in vitro hydroxyl radical generation," *Biochemical and Biophysical Research Communications*, 1998; 253:614-620.

Tashiro et al., "NMDA-receptor-mediated, cell-specific integration of new neurons in adult dentate gyrus," *Nature*, 2006; 442:929-933.

Teratology Society, "Teratology Society position paper: recommendations for vitamin A use during pregnancy," *Teratology*, 1987; 35:267-268.

Teris Clinical Teratology Web; accessed at http://depts.washington.edu/terisdb/terisweb/index.html on May 19, 2016.

Thalomid® (thalidomide), Patient Handout, revised Oct. 2015, accessed at http://reference.medscape.com/drug/thalomid-thalidomide-343211#91 on May 19, 2016.

Thalomid® (thalidomide), Pharmacology, accessed at http://reference.medscape.com/drug/thalomid-thalidomide-343211#10 on May 19, 2016.

Theunissen and Piersma, "Innovative approaches in the embryonic stem cell test (EST)," *Front Biosci*, 2012; 17:1965-1975.

Thiotepa (Product Information), 2006, Bedford Laboratories, Bedford, OH; accessed at https://dailymed.nlm.nih.gov/dailymed/archives/fdaDrugInfo.cfm?archiveid=2444 on May 19, 2016.

Thomson et al., "Embryonic stem cell lines derived from human blastocysts," *Science*, 1998; 282:1145-1147.

Thomson et al., "Not a walk in the park: the ECVAM whole embryo culture model challenged with pharmaceuticals and attempted improvements with random forest design," *Birth Defects Res B Dev Reprod Toxicol*, 2011; 92:111-121.

Toms, D., "Thalidomide and congenital abnormalities," *Lancet*, 1962; 2:400.

Tykerb® (labatinib), Highlights of Prescribing Information, 2007; GlaxoSmithKline, Research Triangle Park, NC.

Tylenol® (acetaminophen tablet), Drug Label Information, Mar. 2015, Cardinal Health.

Ubeda et al., "Physiologic changes in homocysteine metabolism in pregnancy: a longitudinal study in Spain," *Nutrition*, 2011; 27:925-930.

Ushmorov et al., "Differential Reconsitution of Mitochondrial Respiratory Chain Activity and Plasma Redox State by Cysteine and Ornithine in a Model of Cancer Cachexia," *Can Res.*, 1999; 59:3527-3534.

Vaisman et al., "Comparative bioavailability of two oral L-thyroxine formulations after multiple dose administration in patients with hypothyroidism and its relation with therapeutic endpoints and dissolution profiles," *Arzneimittelforschung*, 2001; 51:246-252.

Van Giersbergen et al., "Inhibitory and inductive effects of rifampin on the pharmacokinetics of bosentan in healthy subjects," *Clin Pharm Ter*, 2007; 81:414-419.

Villas-Bôas et al., "Mass spectrometry in metabolome analysis," *Mass Spectrom Rev*, 2005; 24(5):613-46.

Visitide® (cidofovir injection), Package Insert, 2010, Gilead Sciences, Foster City, CA.

Vrana et al., "Nonhuman primate parthenogenetic stem cells," *Proc Natl Acad Sci USA*, 2003; 100(Supp 1): 11911-11916.

(56) References Cited

OTHER PUBLICATIONS

Vriend et al., "Effects of valproate on amino acid and monoamine concentration in striatum of audiogenic seizure-prone balb/c mice," *Molecular and Chemical Neruopathology*, 1996; 27: 307-324.

Walsh S., "Maternal-placental interactions of oxidative stress and antioxidants in preeclampsia," *Semin Reprod Med*, 1998; 16(1):93-104.

Weigt et al., "Zebrafish (*Danio rerio*) embryos as a model for testing proteratogens," *Toxicology*, 2011; 281:25-36.

Weinstein et al., "Pharmacokinetics of continuous intravenous and subcutaneous infusions of cytosine arabinoside," *Blood*, 1982; 59:1351-1353.

Weir et al., "An Alternative Developmental Toxicity Screening Capability," posted at https://www.stemina.com/news-publications/posters on Nov. 3, 2013. Accessed at www.stemina.com/an-alternative-development-toxicity-screening-capability on Aug. 30, 2017.

Welle-Watne et al., "Bioavailability of warfarin from three tablet perparations," *Medd Norsk Farm Selsk*, 1980; 42:103-114.

West et al., "A High Throughout Metabolite-Based Biomarker Approach to Predict Developmental Toxicity Using Human Embryonic Stem Cells", *International Journal of Toxicology*, vol. 32, No. 1, Jan. 2013, p. 70.

West et al., "A Metabolite-Based Biomarker Approach to Predict Developmental Toxicity Using Human Embryonic Stem Cells," poster presented Mar. 12, 2013, at the 2013 Society of Toxicology Annual Meeting, San Antonio, Texas, Mar. 10-14, 2013.

West et al., "Metabolomics as a tool for discovery of biomarkers of autism spectrum disorder in the blood plasma of children," *PLoS One*, Nov. 2014; 9(11):e112445.

West et al., "Predicting Human developmental toxicity of pharmaceuticals using human embryonic stem cells and metabolomics," *Toxicology and Applied Pharmacology*, 2010; 247:18-27.

West, Paul "SBIR Phase II: Metabolomics of Human Embryonic Stem Cells to Predict Teratogenicity: An Alternative Developmental Toxicity Model," Grant Abstract, Grant No. IIP-1058355 [online]. National Science Foundation, project dates Feb. 15, 2011 to Jul. 3, 2015 [retrieved on Aug. 30, 2017]. Retrieved from the Internet:<URL:https://www.nsf.gov/awardsearch/showAward?AWD_ID=1058355&HistoricalAwards=false>; 2 pgs.

Zhang et al., "Development of a streamlined rat whole embryo culture assay for classifying teratogenic potential of pharmaceutical compounds," *Toxicol Sci*, 2012; 127:535-546.

Zhao et al., "Neural tube defects and maternal biomarkers of folate, homocysteine, and glutathione metabolism," *Birth Defects Research Part A: Clinical and Molecular Teratology*, 2006; 76(4):230-236.

Ziagen® (abacavir sulfate), Highlights of Prescribing Information, 2008; GlaxoSmithKline, Research Triangle Park, NC.

\* cited by examiner

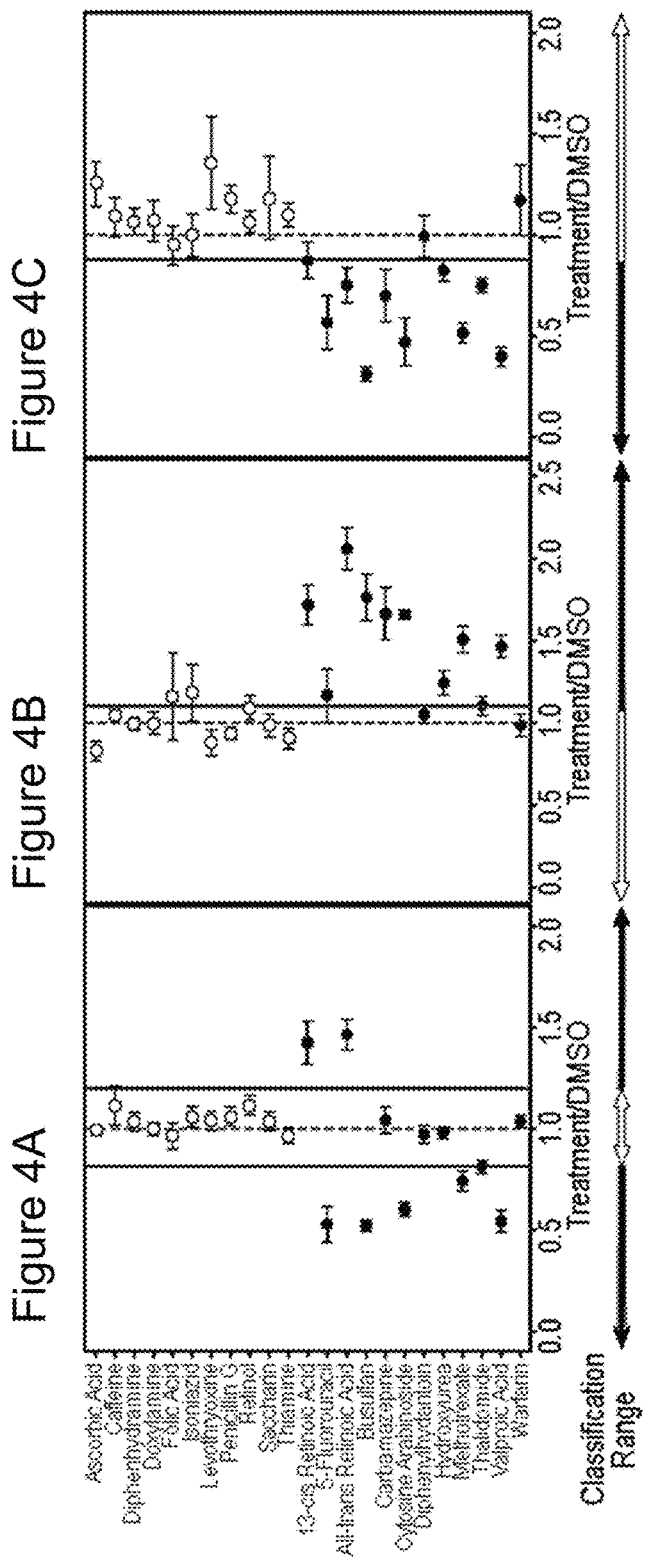

US 10,209,240 B2

PREDICTING HUMAN DEVELOPMENTAL TOXICITY OF PHARMACEUTICALS USING HUMAN STEM-LIKE CELLS AND METABOLOMIC RATIOS

CONTINUING APPLICATION DATA

This application is a divisional application of U.S. application Ser. No. 14/439,723, filed Apr. 30, 2015, and which is a § 371 U.S. National Stage of International Application No. PCT/US2013/067980, filed Nov. 1, 2013, which claims the benefit of U.S. Provisional Applications Ser. No. 61/721,746, filed Nov. 2, 2012, and Ser. No. 61/827,407, filed May 24, 2013, each of which are incorporated by reference herein.

GOVERNMENT FUNDING

This invention was made with government support under Grant No. IIP-1058355, awarded by the National Science Foundation. The Government has certain rights in the invention.

BACKGROUND

Birth defects are reported in approximately 3% of all human births and are the largest cause of infant mortality in the United States (Hoyert et al., 2006, *Pediatrics;* 117:168-183). Exposure to toxic chemicals and physical agents is believed to be responsible for approximately 3% of all birth defects (National Research Council, 2000, "Scientific frontiers in developmental toxicology and risk assessment," Washington, D.C.: The National Academies Press).

It is understood that developmental toxicity can cause birth defects, and can generate embryonic lethality, intrauterine growth restriction (IUGR), dysmorphogenesis (such as skeletal malformations), and functional toxicity, which can lead to cognitive disorders such as autism. There is an increasing concern about the role that chemical exposure can play in the onset of these disorders. Indeed, it is estimated that 5% to 10% of all birth defects are caused by in utero exposure to known teratogenic agents that induce developmental abnormalities in the fetus (Beckman and Brent, 1984, *Annu Rev Pharmacol;* 24: 483-500). Concern exists that chemical exposure may be playing a significant and preventable role in producing birth defects (Claudio et al., 2001, *Environm Health Perspect;* 109: A254-A261).

However, this concern has been difficult to evaluate, due to the lack of robust and efficient models for testing developmental toxicity for the more than 80,000 chemicals in the market, plus the new 2,000 compounds introduced annually (General Accounting Office (GAO), 1994, Toxic Substances Control Act: Preliminary Observations on Legislative Changes to Make TSCA More Effective, Testimony, Jul. 13, 1994, GAO/T-RCED-94-263). Fewer than 5% of these compounds have been tested for reproductive outcomes and even fewer for developmental toxicity (Environmental Protective Agency (EPA), 1998, Chemical Hazard Data Availability Study, Office of Pollution Prevention and Toxins). Although some attempts have been made to use animal model systems to assess toxicity (Piersma, 2004, *Toxicology Letters;* 149: 147-53), inherent differences in the sensitivity of humans in utero have limited the predictive usefulness of such models.

Toxicity, particularly developmental toxicity, is also a major obstacle in the progression of compounds through the drug development process. Currently, toxicity testing is conducted on animal models as a means to predict adverse effects of compound exposure, particularly on development and organogenesis in human embryos and fetuses. The most prevalent models that contribute to FDA approval of investigational new drugs are whole animal studies in rabbits and rats (Piersma, 2004, *Toxicology Letters;* 149: 147-53). In vivo studies rely on administration of compounds to pregnant animals at different stages of pregnancy and embryonic/fetal development (first week of gestation, organogenesis stage and full gestation length). However, these in vivo animal models are limited by a lack of biological correlation between animal and human responses to chemical compounds during development due to differences in biochemical pathways. Species differences are often manifested in trends such as dose sensitivity and pharmacokinetic processing of compounds. According to the reported literature, animal models are approximately 60% efficient in predicting human developmental response to compounds (Greaves et al., 2004, *Nat Rev Drug Discov;* 3:226-36). Thus, there is a need for human-directed predictive in vitro models.

The thalidomide tragedy in the 1960s emphasized the importance of preclinical developmental toxicity testing, the significant differences among species in their response to potentially teratogenic compounds, and how the developing fetus can be affected by such compounds. Developmental toxicity testing of thalidomide in rodent models did not indicate the compound's teratogenic potential in humans. Over 10,000 children were born with severe birth defects following in utero exposure. Current preclinical models for detecting developmental toxicity have varying degrees of concordance with observed developmental toxicity in humans, with rats and rabbits (the most commonly used species for developmental toxicity testing) having approximately 70-80% concordance to known human teratogens (Daston G P and Knudsen T B, 2010, "Fundamental concepts, current regulatory design and interpretation," In: Knudsen T B, Daston G P, editors. *Comprehensive Toxicology*. Vol 12, 2nd ed. New York: Elsevier. p 3-9). These decades-old in vivo animal models require large numbers of animals, kilogram quantities of test compound, and are both time consuming and expensive. Due to the cost and complexity of these models, safety assessments often occur too late in the compound's life cycle for the developer to react to a positive developmental toxicity signal, and can result in the termination of the development of the compound or series. Though these animal models are, and have long been, considered the regulatory gold standard, differences in species response to a compound may lead to missed signals of developmental toxicity and biological misinterpretation. As such, the development of a new generation of tools using human cells for assessment of potential developmental toxicity risk related to chemical exposure is needed. The appropriate tests would also reduce product development time, control costs, and respond proactively to the call to decrease animal use.

Thus, there is a need for a relevant, predictive, accurate, low cost, and rapid human in vitro tests for reliably determining developmental toxicity of pharmaceutical agents and other chemical compounds.

SUMMARY OF THE INVENTION

The present invention includes a method of classifying a test compound as a teratogen or a non-teratogen, the method including culturing undifferentiated human stem cell-like cells (hSLCs) in the presence of the test compound and in the absence of the test compound; determining the fold change in ornithine, or fragment, adduct, deduct or loss thereof, in the culture media of undifferentiated hSLCs cultured in the presence of the test compound in comparison with hSLCs cultured in the absence of the test compound; determining the fold change in cystine, or fragment, adduct, deduct or loss thereof, in the culture media of undifferentiated hSLCs cultured in the presence of the test compound in comparison with hSLCs cultured in the absence of the test compound; and determining the ratio of the fold change in ornithine, or fragment, adduct, deduct or loss thereof, to the fold change in cystine, or fragment, adduct, deduct or loss thereof, wherein a ratio of less than or equal to about 0.88 is indicative of the teratogenicity of the test compound and a ratio of greater than about 0.88 is indicative of the non-teratogenicity of the test compound.

The present invention includes a method of predicting teratogenicity of a test compound, the method including culturing undifferentiated human stem cell-like cells (hSLCs) in the presence of the test compound and in the absence of the test compound; determining the fold change in ornithine, or fragment, adduct, deduct or loss thereof, in the culture media of undifferentiated hSLCs cultured in the presence of the test compound in comparison with hSLCs cultured in the absence of the test compound; determining the fold change in cystine, or fragment, adduct, deduct or loss thereof, in the culture media of undifferentiated hSLCs cultured in the presence of the test compound in comparison with hSLCs cultured in the absence of the test compound; and determining the ratio of the fold change in ornithine, or fragment, adduct, deduct or loss thereof, to the fold change in cystine, or fragment, adduct, deduct or loss thereof, wherein a ratio of less than or equal to about 0.88 is indicative of the teratogenicity of the test compound and a ratio of greater than about 0.88 is indicative of the non-teratogenicity of the test compound.

The present invention includes a method for validating a test compound as a teratogen, the method including culturing undifferentiated human stem cell-like cells (hSLCs) in the presence of the test compound and in the absence of the test compound; determining the fold change in ornithine, or fragment, adduct, deduct or loss thereof, in the culture media of undifferentiated hSLCs cultured in the presence of the test compound in comparison with hSLCs cultured in the absence of the test compound; determining the fold change in cystine, or fragment, adduct, deduct or loss thereof, in the culture media of undifferentiated hSLCs cultured in the presence of the test compound in comparison with hSLCs cultured in the absence of the test compound; and determining the ratio of the fold change in ornithine, or fragment, adduct, deduct or loss thereof, to the fold change in cystine, or fragment, adduct, deduct or loss thereof, wherein a ratio of less than or equal to about 0.88 is indicative of the teratogenicity of the test compound and a ratio of greater than about 0.88 is indicative of the non-teratogenicity of the test compound.

The present invention includes a method for determining the exposure concentration at which a test compound is teratogenic, the method including culturing undifferentiated human stem cell-like cells (hSLCs) in a range of concentrations of the test compound and in the absence of the test compound; determining the fold change in ornithine, or fragment, adduct, deduct or loss thereof, in the culture media of undifferentiated hSLCs cultured in each concentration of the test compound in comparison with hSLCs cultured in the absence of the test compound; determining the fold change in cystine, or fragment, adduct, deduct or loss thereof, in the culture media of undifferentiated hSLCs cultured in each concentration of the test compound in comparison with hSLCs cultured in the absence of the test compound; and determining the ratio of the fold change in ornithine, or fragment, adduct, deduct or loss thereof, to the fold change in cystine, or fragment, adduct, deduct or loss thereof, for each concentration of test compound, wherein a ratio of less than or equal to about 0.88 at a given concentration of the test compound is indicative of the teratogenicity of the test compound at that given concentration and a ratio of greater than about 0.88 at a given concentration of the test compound is indicative of the non-teratogenicity of the test compound at that given concentration.

In some aspects of the methods of the present invention, cystine, or fragment, adduct, deduct or loss thereof, and/or ornithine, or fragment, adduct, deduct or loss thereof, are identified using a physical separation method. In some aspects, a physical separation method includes mass spectrometry. In some aspects, mass spectrometry includes liquid chromatography/electrospray ionization mass spectrometry.

In some aspects of the methods of the present invention, cystine, or fragment, adduct, deduct or loss thereof, and/or ornithine, or fragment, adduct, deduct or loss thereof, are measured using a colorimetric or immunological assay.

In some aspects of the methods of the present invention, hSLCs includes human embryonic stem cells (hESCs), human induced pluripotent (iPS) cells, or human embryoid bodies.

In some aspects of the methods of the present invention, the hSLCs are cultured at a concentration of the test compound including the test compound's human therapeutic Cmax.

In some aspects of the methods of the present invention, the hSLCs are cultured in a range of concentrations of the test compound. In some aspects, the range of concentrations includes a serial dilution. In some aspects, the range of concentrations includes nine three-fold dilutions. In some aspects, the range of concentrations includes from about 0.04 µM to about 300 µM, about 4 µM to about 30,000 µM, and about 0.0001 µM to about 10µ. In some aspects, the range of concentrations of the test compound includes the test compound's human therapeutic Cmax.

In some aspects of the methods of the present invention, the method further includes detecting one or more additional metabolites associated with hSLCs cultured in the presence of the test compound in comparison with hSLCs cultured in the absence of the test compound. In some aspects, one or more additional metabolite includes arginine, ADMA, cystathionine, and/or a fragment, adduct, deduct or loss thereof. In some aspects, one or more additional metabolites are identified using a physical separation method. In some aspects, a physical separation method includes mass spectrometry. In some aspects, mass spectrometry includes liquid chromatography/electrospray ionization mass spectrometry. In some aspects, one or more additional metabolites are measured using a colorimetric or immunological assay.

In some aspects of the methods of the present invention, the method further includes determining the ratio of the fold change in arginine, or fragment, adduct, deduct or loss thereof, to the fold change in ADMA, or fragment, adduct, deduct or loss thereof, wherein a ratio of less than at least about 0.9 or greater than at least about 1.1 is indicative of the teratogenicity of the test compound and a ratio of greater than at least about 0.9 and less than at least about 1.1 is indicative of the non-teratogenicity of the test compound.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. The embodiment(s) described, and references in the specification to "one embodiment," "an embodiment of the invention," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The terms "comprises" and variations thereof do not have a limiting meaning where these terms appear in the description and claims. It is understood that wherever embodiments are described herein with the language "comprising," otherwise analogous embodiments described in terms of "consisting of" and/or "consisting essentially of" are also provided.

Unless otherwise specified, "a," "an," "the," and "at least one" are used interchangeably and mean one or more than one.

In the following description, for purposes of explanation, specific numbers, parameters and reagents are set forth in order to provide a thorough understanding of the invention. It is understood, however, that the invention can be practiced without these specific details. In some instances, well-known features can be omitted or simplified so as not to obscure the present invention.

Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 4A, 4B, and 4C. Metabolic perturbation of ornithine (FIG. 4A), cystine (FIG. 4B), and the o/c ratio (FIG. 4C) measured in experimental Phase 1. Each point represents the mean value of the 9 independent experimental blocks. Filled points indicate teratogens and open points indicate non-teratogens. Error bars are the standard error of the mean. The vertical grey line(s) represent the teratogenicity threshold. The x-axis is the reference normalized fold change of each metabolite (FIGS. 4A and 4B) or the ratio of ornithine/cystine reference normalized values (FIG. 4C). The y-axis is the treatment ordered by non-teratogens and teratogens. Open arrows indicate range where a compound would be classified as a non-teratogen. Filled arrows indicate the range where a compound would be classified as a teratogen.

DETAILED DESCRIPTION OF ILLUSTRATIVE EMBODIMENTS

Figure 1A:
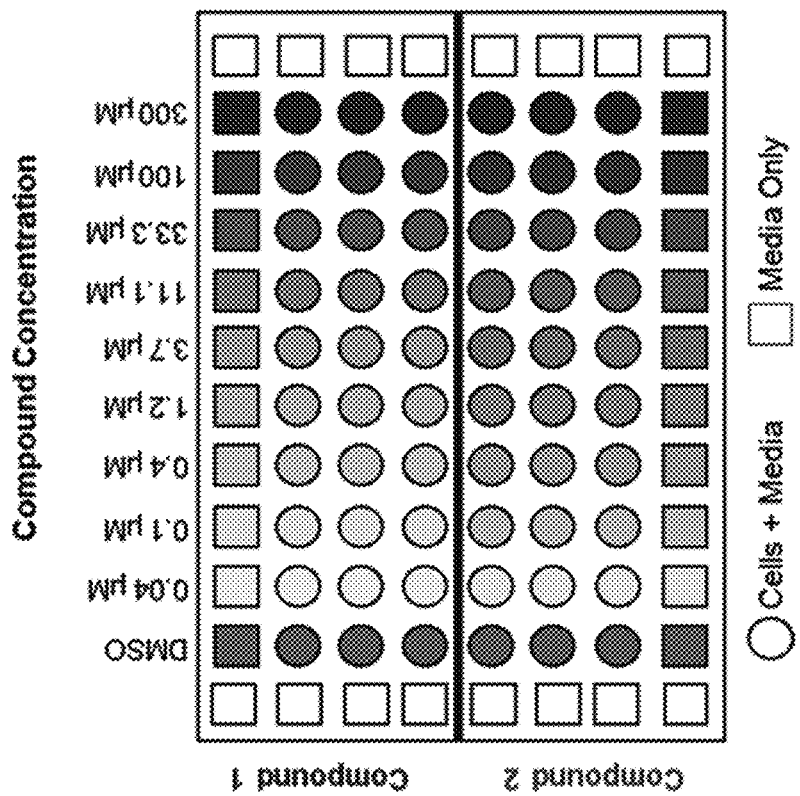
FIGS. 1A and 1B. Plate design for untargeted metabolomics treated at single exposure levels used in Phase 1 experiments (FIG. 1A) and targeted biomarker experiments treated at multiple exposure levels used for Phase 2 experiments (FIG. 1B). Both plates incorporate a reference design where the experimental control or reference treatment (0.1% DMSO) is present on each plate. Media only (lacking cells) controls are used to assess the impact of the test compounds on the sample matrix. Each well is analyzed as an individual sample. Filled circles represent cell samples and filled squares depict media control samples.

The present invention provides human-specific in vitro methods for determining toxicity, particularly developmental toxicity, and teratogenicity of pharmaceuticals and other non-pharmaceutical chemical compounds using human stem-like cells (hSLCs). The present invention utilizes hSLCs and metabolomics to provide a predictive, quantitative, all-human in vitro screening method for predicting human developmental toxicity of compounds. The present methods overcome limitations associated with interspecies animal models and provide innovative and robust alternative in vitro model systems to predict developmental toxicity of chemicals. The application of more predictive developmental toxicity screens would reduce the prevalence of birth defects and increase pharmaceutical and chemical safety.

The present invention provides an exposure-based in vitro assay by measuring a metabolic perturbation in the culture media that could be used as an early signal for the potential of developmental toxicity.

With the methods of the present invention, any of a variety of human stem-like cells (hSLCs) may be used to predict developmental toxicity of chemical entities. Human stem-like cells include, but are not limited to, pluripotent, undifferentiated human embryonic stem cells (hESCs), human induced pluripotent (iPS) cells, human embryoid bodies, and hSLC-derived lineage-specific cells.

hESCs are pluripotent, self-renewing cells isolated directly from preimplantation human embryos that recapitulate organogenesis in vitro. Lineage-specific precursor cells are derived from hESCs and have entered a specific cellular lineage, but yet remain multipotent with regard to cell type within that specific lineage. For example, neural precursors have committed to neural differentiation but yet remain unrestricted as to its neural cell type. As used herein, the term "human embryonic stem cells (hESCs)" is intended to include undifferentiated stem cells originally derived from the inner cell mass of developing blastocysts, and specifically pluripotent, undifferentiated human stem cells and partially-differentiated cell types thereof (e.g., downstream progenitors of differentiating hESC). As provided herein, in vitro cultures of hESCs are pluripotent and not immortalized, and can be induced to produce lineage-specific cells and differentiated cell types using methods well-established in the art. hESCs useful in the practice of the methods of the present invention include, but are not limited to, those are derived from preimplantation blastocysts, for example, as described by Thomson et al., in U.S. Pat. No. 6,200,806. Multiple hESC lines are currently available in US and UK stem cell banks. hESCs used may include any of the three hES cell lines, WA01, WA07, and WA09. Previous work has established that an untargeted metabolomics-based evaluation of hES cell spent media following exposure to compounds with known human teratogenicity outcomes produces predictive signatures that can be utilized as a developmental toxicity screen (Kleinstreuer et al., 2011, *Toxicol Appl Pharmacol;* 257:111-121; and West et al., 2010, *Toxicol Appl Pharmacol;* 247:18-27, each of which is incorporated herein in its entirety).

Human induced pluripotent stem cells (iPS) cells are a type of pluripotent stem cell artificially derived from a non-pluripotent cell, typically an adult somatic cell, by inducing a forced expression of certain genes. iPS cells are believed to be identical to natural pluripotent stem cells, such as embryonic stem cells in many respects, such as the expression of certain stem cell genes and proteins, chromatin methylation patterns, doubling time, embryoid body formation, teratoma formation, viable chimera formation, and potency and differentiability. iPS cells may be obtained, for example, from adult tissues (such as for example, from cells obtained from the bone the marrow) and by parthenogenesis (see, for example, Vrana et al., 2003, *Colloquium;* 100, Supp. 1:11911-11916).

Human embryoid bodies are aggregates of cells derived from human embryonic stem cells. Cell aggregation is imposed by hanging drop, plating upon non-tissue culture treated plates or spinner flasks; either method prevents cells from adhering to a surface to form the typical colony growth. Upon aggregation, differentiation is initiated and the cells begin to a limited extent to recapitulate embryonic development. Embryoid bodies are composed of cells from all three germ layers: endoderm, ectoderm and mesoderm.

The cells of the present invention can include hSLC-derived lineage specific cells. The terms "hSLC-derived lineage specific cells,", "stem cell progenitor," "lineage-specific cell," "hSLC derived cell," and "differentiated cell" as used herein are intended to encompass lineage-specific cells that are differentiated from hSLCs such that the cells have committed to a specific lineage of diminished pluripotency. For example, hSLC-derived lineage specific cells are derived from hSLCs and have entered a specific cellular lineage, but yet remain multipotent with regard to cell type within that specific lineage. The hSLC-derived lineage specific cells can include, for example, neural stem cells, neural precursor cells, neural cells, cardiac stem cells, cardiac precursor cells, cardiomyocytes, and the like. In some embodiments, these hSLC-derived lineage-specific cells remain undifferentiated with regard to final cell type. For example, neuronal stem cells are derived from hSLCs and have differentiated enough to commit to neuronal lineage. However, the neuronal precursor retains "stemness" in that it retains the potential to develop into any type of neuronal cell. Additional cell types include terminally-differentiated cells derived from hESCs or lineage-specific precursor cells, for example neural cells.

With the methods of the present invention, hSLCs may be cultured using methods of cell culture well-known in the art, including, for example, methods disclosed in Ludwig et al. (2006, *Nat Methods;* 3:637-46), U.S. patent application Ser. No. 11/733,677 ("Reagents and Methods for Using Human Embryonic Stem Cells to Evaluate Toxicity of Pharmaceutical Compounds and other Compounds"), PCT/US2011/029471 and U.S. patent application Ser. No. 13/069,326 ("Predicting Human Developmental Toxicity of Pharmaceuticals Using Human Stem-Like Cells and Metabolomics"), and any of those described herein.

In some aspects of the present invention, hSLCs are maintained in an undifferentiated state prior to and/or during exposure to a test compound. In some aspects of the present invention, hSLCs may be cultured in the absence of a feeder cell layer during exposure to a test compound and/or cultured on feeder cell layer prior to such exposure.

The methods of the present invention profile changes in cellular metabolism that are measured in the spent cell culture medium from hSLCs following compound exposure. This metabolic footprint of the culture medium is a functional measurement of cellular metabolism referred to as the "secretome." The secretome refers to the metabolites present in the spent media (which may also be referred be herein as "cell culture supernatant," "culture supernatant," "supernatant," "cell supernatant," "cell culture media," "culture media," "cell culture medium," "culture medium," "media," or "medium") following cell culture. The secretome includes media components, metabolites passively and actively transported across the plasma membrane, intracellular metabolites release upon lysis, and those produced through extracellular metabolism of enzymes. The change in the secretome elicited by test compound exposure relative to untreated cultures produces a metabolic signature of toxicity. The secretome is measured because of several unique qualities for profiling cell culture media; it is very easy to reproducibly sample, minimal handling is required to quench metabolism, it does not destroy the cells that can then be used for other assays, it is amenable to high-throughput evaluation, and strong signals can be measured due to the accumulation of metabolites over time. The ability to measure metabolic changes following compound exposure has identified new biomarkers associated with disruption of human development and provided the opportunity to develop highly predictive models of developmental toxicity based on these changes.

Metabolites include, but are not limited to, sugars, organic acids, amino acids, fatty acids, hormones, vitamins, oligopeptides (less than about 100 amino acids in length), as well as ionic fragments thereof. In some aspects, metabolites are less than about 3000 Daltons in molecular weight, and more particularly from about 50 to about 3000 Daltons.

With the present invention, a fold change in a metabolite in hSLCs cultured in the presence of a test compound in comparison with hSLCs cultured in the absence of the teratogenic compound may be determined. The metabolic effect of a teratogenic compound refers to the difference in one or more metabolites in hSLCs cultured in presence of the teratogenic compound in comparison with hSLCs cultured in absence of the teratogenic compound (or, in some aspects, hSLCs cultured in presence of a known non-teratogenic compound). A metabolite may be differentially expressed, for example, the expression of a metabolite may be increased or decreased when exposed to a teratogenic compound.

In some aspects, a ratio of the fold changes of two metabolites in hSLCs cultured in presence of a test compound in comparison with hSLCs cultured in absence of the teratogenic compound may be determined. For example, with the present invention, it has been determined that altered ratios in the fold changes of ornithine to cystine, asymmetric dimethylarginine (ADMA) to cystine, and/or cystathionine to cystine may be predictive of the developmental toxicity/teratogenicity of a test compound. Any one, two or all three of these ration may be utilized in the determination of the developmental toxicity of a compound.

With the present invention, a change in the secretome elicited by test compound exposure relative to untreated cultures produces a metabolic signature that may be used for measuring cell viability. Changes in cellular metabolism as measured in the spent medium following cell culture are a functional measure of cell health. The change in the secretome elicited by exposure to a test agent relative to untreated cultures produces a metabolic signature that can be used to infer the number of metabolically viable cells present within a cell culture. One or more of the secreted metabolites described herein can be utilized to infer the number viable cells relative to the number of cells in a reference culture "control group." These metabolites could be utilized to determine the number of viable cells within a cell culture without a requirement to destroy or impact the cells. These metabolites can be used as novel measure of viability that does not require disrupting the growing cells.

With the present invention, a change in the secretome elicited by exposure to a range of concentrations of a test compound relative to untreated cultures may be used to determine the concentration at which a test compound is teratogenic. The teratogenic potential of a compound is associated with the level of exposure to the fetus. Therefore a compound could be considered both teratogenic and non-teratogenic depending on the exposure level. For example, retinol (vitamin A), when taken at or below the Food and Drug Administration (FDA) maximum recommended daily allowance (RDA; 8,000 IU), does not have an adverse effect on the developing fetus. However, high doses of retinol (>25,000 IU/day) have been shown to cause malformations similar to those seen following 13-cis retinoic acid exposure in both experimental animals and humans (Teratology Society, 1987, "Teratology Society position paper: recommendations for vitamin A use during pregnancy," *Teratology;* 35:269-275).

In some aspects, the teratogenicity of a compound may be tested at concentrations corresponding to their IC50 or EC50 dose levels, at concentrations corresponding to their circulating dose, at concentrations corresponding to in maternal circulation and/or at concentrations corresponding to the test compound's human therapeutic $C_{max}$. Such dosing recapitulates the exposure level to a developing human embryo in vivo and the toxic or teratogenic effect of the dosing compound on human development.

In some aspects, the teratogenicity of a compound may be tested over a range of concentrations of the test compound. Such a range may include, for example, about 0.04 µM to about 300 µM, about 4 µM to about 30,000 µM, and about 0.0001 µM to about 10 µM. Such a range may include, for example, a serial dilution of, for example, five, six, seven, eight, nine, ten, or more dilutions. Such dilutions may be, for example, two-fold, three-fold, four-fold, five-fold, ten-fold, or more.

With the present invention, individual metabolites and/or ratios of fold changes may be utilized in concordance with cell viability data for the prediction of developmental toxicity. The quickPredict method described herein combines cell culture based evaluation of a nine-point dose curve with a metabolic index to predict the dose at which a test agent may exhibit developmental toxicity and cytotoxicity within a seven day time frame. This assay workflow represent a significant five-fold increase in throughput over traditional 'omics' based computational approaches. In the previously described devTox assay (see, for example, PCT/US2011/029471 and U.S. patent application Ser. No. 13/069,326 ("Predicting Human Developmental Toxicity of Pharmaceuticals Using Human Stem-Like Cells and Metabolomics," West et al., 2010, *Toxicol Appl Pharmacol;* 247(1):18-27, and Kleinstreuer et al., 2011, *Toxicol Appl Pharmacol;* 257(1):111-121), stem cells are dosed with a test compound in two steps, (1) at multiple concentrations for cell viability measurements which are performed to determine the optimal dose levels for metabolomics studies that provide a maximum metabolic response with a minimum of cell death, and (2) then after the best concentration was determined, a new batch of cells is then dosed with 3 concentrations derived from the optimal concentration and $IC_{50}$, the media is collected for LC-MS analysis using both ESI positive and ESI negative ionization polarities. In the QuickPredict methods of the present invention, media is collected from the first step 96-well plates containing the cells dosed at multiple concentrations and is analyzed directly on the mass spectrometer using a much shorter LC gradient (6.5 minutes versus 23 minutes for the previous method), using only positive polarity ESI. In some aspects, the QuickPredict method may utilize a Waters Acquity UPLC BEH Amide 2.1×50 1.7 uM column, rather than a longer Phenomenex Luna HILIC 100×3 mm 1.7 uM column. LC-MS data can be acquired for two 96 well plates (corresponding to 2 test compounds) in 18 hours.

In some aspects, a fold change ratio of other than about 1 is indicative of the teratogenicity of the test compound, for example, a fold change ratio of greater than about 1 (for example, including, but not limited to, about 1.01, about 1.02, about 1.03, about 1.04, about 1.05, about 1.06, about 1.07, about 1.08, about 1.09, about 1.1, about 1.11, about 1.12, about 1.13, about 1.14, about 1.15, about 1.16, about 1.17, about 1.18, about 1.19, about 1.2, about 1.21, about 1.22, about 1.23, about 1.24, about 1.25, about 1.26, about 1.27, about 1.28, about 1.29, about 1.3, about 1.31, about 1.32, about 1.33, about 1.34, about 1.35, about 1.36, about 1.37, about 1.38, about 1.39, about 1.4, about 1.41, about 1.42, about 1.43, about 1.44, about 1.45, about 1.46, about 1.47, about 1.48, about 1.49, or about 1.5) and/or a fold change ratio of less than about 1 (for example, including, but not limited to, about 0.99, about 0.98, about 0.97, about 0.96, about 0.95, about 0.94, about 0.93, about 0.92, about 0.91, about 0.9, about 0.89, about 0.88, about 0.87, about 0.86, about 0.85, about 0.84, about 0.83, about 0.82, about 0.81, about 0.8, about 0.79, about 0.78, about 0.77, about 0.76, about 0.75, about 0.74, about 0.73, about 0.72, about 0.71, about 0.7, about 0.69, about 0.68, about 0.67, about 0.66, about 0.65, about 0.64, about 0.63, about 0.62, about 0.61, about 0.6, about 0.59, about 0.58, about 0.57, about 0.56, about 0.55, about 0.54, about 0.53, about 0.52, about 0.51, or about 0.5).

For example, in some aspects, a fold change ratio of less than about 0.9 and/or greater than about 1.1 is indicative of the teratogenicity of the test compound and a fold change ratio of greater than about 0.9 and/or less than about 1.1 is indicative of the non-teratogenicity of the test compound. In some aspects, a fold change ratio of less than or equal to about 0.9 and/or greater than or equal to about 1.1 is indicative of the teratogenicity of the test compound and a fold change ratio of greater than about 0.9 and/or less than about 1.1 is indicative of the non-teratogenicity of the test compound.

For example, in some aspects, a fold change ratio of less than about 0.89 and/or greater than about 1.11 is indicative of the teratogenicity of the test compound and a fold change ratio of greater than about 0.89 and/or less than about 1.11 is indicative of the non-teratogenicity of the test compound. In some aspects, a fold change ratio of less than or equal to about 0.89 and/or greater than or equal to about 1.11 is indicative of the teratogenicity of the test compound and a fold change ratio of greater than about 0.89 and/or less than about 1.1 is indicative of the non-teratogenicity of the test compound.

For example, in some aspects, a fold change ratio of less than about 0.88 and/or greater than about 1.12 is indicative of the teratogenicity of the test compound and a fold change ratio of greater than about 0.88 and/or less than about 1.12 is indicative of the non-teratogenicity of the test compound. In some aspects, a fold change ratio of less than or equal to about 0.88 and/or greater than or equal to about 1.12 is indicative of the teratogenicity of the test compound and a fold change ratio of greater than about 0.88 and/or less than about 1.12 is indicative of the non-teratogenicity of the test compound.

For example, in some aspects, a fold change ratio of less than about 0.87 and/or greater than about 1.13 is indicative of the teratogenicity of the test compound and a fold change ratio of greater than about 0.87 and/or less than about 1.13 is indicative of the non-teratogenicity of the test compound. In some aspects, a fold change ratio of less than or equal to about 0.87 and/or greater than or equal to about 1.13 is indicative of the teratogenicity of the test compound and a fold change ratio of greater than about 0.87 and/or less than about 1.13 is indicative of the non-teratogenicity of the test compound.

For example, in some aspects, a fold change ratio of less than about 0.86 and/or greater than about 1.14 is indicative of the teratogenicity of the test compound and a fold change ratio of greater than about 0.86 and/or less than about 1.14 is indicative of the non-teratogenicity of the test compound. In some aspects, a fold change ratio of less than or equal to about 0.86 and/or greater than or equal to about 1.14 is indicative of the teratogenicity of the test compound and a fold change ratio of greater than about 0.86 and/or less than about 1.14 is indicative of the non-teratogenicity of the test compound.

For example, in some aspects, a fold change ratio of less than about 0.85 and/or greater than about 1.15 is indicative of the teratogenicity of the test compound and a fold change ratio of greater than about 0.85 and/or less than about 1.15 is indicative of the non-teratogenicity of the test compound. In some aspects, a fold change ratio of less than or equal to about 0.85 and/or greater than or equal to about 1.15 is indicative of the teratogenicity of the test compound and a fold change ratio of greater than about 0.85 and/or less than about 1.15 is indicative of the non-teratogenicity of the test compound.

For example, in some aspects, a fold change ratio of less than about 0.84 and/or greater than about 1.16 is indicative of the teratogenicity of the test compound and a fold change ratio of greater than about 0.84 and/or less than about 1.16 is indicative of the non-teratogenicity of the test compound. In some aspects, a fold change ratio of less than or equal to about 0.84 and/or greater than or equal to about 1.16 is indicative of the teratogenicity of the test compound and a fold change ratio of greater than about 0.84 and/or less than about 1.16 is indicative of the non-teratogenicity of the test compound.

A determination of a metabolite, fragment, adduct, deduct or loss thereof, may be identified using a physical separation method. In some embodiments, a metabolite, fragment, adduct, deduct or loss thereof, may be identified using a methodology other than a physical separation method. Such measurement methods may include, for example, colorimetric assays, enzymatic assays, or immunological assays. Immunological assays may include, for example, IF, MA, ELISA and other immunoassays. Alternatively, certain biomarkers can be identified by, for example, gene expression analysis, including real-time PCR, RT-PCR, Northern analysis, and in situ hybridization.

The term "physical separation method" as used herein refers to method known to those with skill in the art sufficient to produce a profile of changes and differences in small molecules produced in hSLCs, contacted with a toxic, teratogenic or test chemical compound. In some embodiments, physical separation methods permit detection of cellular metabolites including but not limited to sugars, organic acids, amino acids, fatty acids, hormones, vitamins, and oligopeptides, as well as ionic fragments thereof and low molecular weight compounds (preferably with a molecular weight less than 3000 Daltons, and more particularly between 50 and 3000 Daltons). For example, mass spectrometry can be used. In particular embodiments, this analysis may be performed by liquid chromatography/electrospray ionization time of flight mass spectrometry (LC/ESI-TOF-MS). However it will be understood that metabolites as set forth herein can be detected using alternative spectrometry methods or other methods known in the art, including, but not limited to, any of those described herein.

For example, biomarkers are identified by methods including LC/ESI-TOF-MS and/or QTOF-MS. Metabolomic biomarkers are identified by their unique molecular mass and consistency with which the marker is detected in response to a particular toxic, teratogenic or test chemical compound; thus the actual identity of the underlying compound that corresponds to the biomarker is not required for the practice of this invention.

Biomarkers may be identified using, for example, Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, tandem mass spectrometry (e.g., MS/MS, MS/MS/MS, ESI-MS/MS etc.), secondary ion mass spectrometry (SIMS), and/or ion mobility spectrometry (e.g. GC-IMS, IMS-MS, LC-IMS, LC-IMS-MS etc.).

In some aspects, a gas phase ion spectrophotometer may be used. In other aspects, laser-desorption/ionization mass spectrometry may be used to identify biomarkers. For example, modern laser desorption/ionization mass spectrometry (LDI-MS) may be practiced in two main variations; matrix assisted laser desorption/ionization (MALDI) mass spectrometry and surface-enhanced laser desorption/ionization (SELDI). In MALDI, the analyte is mixed with a solution containing a matrix, and a drop of the liquid is placed on the surface of a substrate. The matrix solution then co-crystallizes with the biomarkers. The substrate is inserted into the mass spectrometer. Laser energy is directed to the substrate surface where it desorbs and ionizes the proteins without significantly fragmenting them. However, MALDI has limitations as an analytical tool. It does not provide means for fractionating the biological fluid, and the matrix material can interfere with detection, especially for low molecular weight analytes. In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the biomarker of interest and that contain a photolytic bond that is broken upon application of the laser. In each of these methods, the derivatizing agent generally is localized to a specific location on the substrate surface where the sample is applied. The two methods can be combined by, for example, using a SELDI affinity surface to capture an analyte (e.g. biomarker) and adding matrix-containing liquid to the captured analyte to provide the energy absorbing material.

Data from mass spectrometry may be represented as a mass chromatogram. A "mass chromatogram" is a representation of mass spectrometry data as a chromatogram, where the x-axis represents time and the y-axis represents signal intensity. In one aspect the mass chromatogram may be a total ion current (TIC) chromatogram. In another aspect, the mass chromatogram may be a base peak chromatogram. In other aspects, the mass chromatogram may be a selected ion monitoring (SIM) chromatogram. In yet another aspect, the mass chromatogram may be a selected reaction monitoring (SRM) chromatogram. In yet another aspect, the mass chromatogram may be an extracted ion chromatogram (EIC). In an EIC, a single feature is monitored throughout the entire run. The total intensity or base peak intensity within a mass tolerance window around a particular analyte's mass-to-charge ratio is plotted at every point in the analysis. The size of the mass tolerance window typically depends on the mass accuracy and mass resolution of the instrument collecting the data. As used herein, the term "feature" refers to a single small metabolite, or a fragment of a metabolite. In some embodiments, the term feature may also include noise upon further investigation.

A person skilled in the art understands that any of the components of a mass spectrometer, e.g., desorption source, mass analyzer, detect, etc., and varied sample preparations can be combined with other suitable components or preparations described herein, or to those known in the art. For example, a control sample may contain heavy atoms, e.g. $^{13}C$, thereby permitting the test sample to be mixed with the known control sample in the same mass spectrometry run. Good stable isotopic labeling is included.

A laser desorption time-of-flight (TOF) mass spectrometer may be used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio. In one aspect, levels of biomarkers may be detected by MALDI-TOF mass spectrometry.

Methods of detecting biomarkers also include the use of surface plasmon resonance (SPR). The SPR biosensing technology may be combined with MALDI-TOF mass spectrometry for the desorption and identification of biomarkers.

A computer may be used for statistical analysis. Data for statistical analysis can be extracted from chromatograms (spectra of mass signals) using softwares for statistical methods known in the art. Statistics is the science of making effective use of numerical data relating to groups of individuals or experiments. Methods for statistical analysis are well-known in the art.

For example, the Agilent MassProfiler or MassProfiler-Professional software may be used for statistical analysis. Or, the Agilent MassHunter software Qual software may be used for statistical analysis. Alternative statistical analysis methods can be used. Such other statistical methods include the Analysis of Variance (ANOVA) test, Chi-square test, Correlation test, Factor analysis test, Mann-Whitney U test, Mean square weighted derivation (MSWD), Pearson product-moment correlation coefficient, Regression analysis, Spearman's rank correlation coefficient, Student's T test, Welch's T-test, Tukey's test, and Time series analysis.

In some aspects, signals from mass spectrometry can be transformed in different ways to improve the performance of the method. Either individual signals or summaries of the distributions of signals (such as mean, median or variance) can be so transformed. Possible transformations include taking the logarithm, taking some positive or negative power, for example the square root or inverse, or taking the arcsin (Myers, *Classical and Modern Regression with Applications*, 2nd edition, Duxbury Press, 1990).

In some aspects, statistical classification algorithms can be used to create a classification model in order to predict teratogenicity and non-teratogenicity of test compounds. Machine learning-based classifiers have been applied in various fields such as machine perception, medical diagnosis, bioinformatics, brain-machine interfaces, classifying DNA sequences, and object recognition in computer vision. Learning-based classifiers have proven to be highly efficient in solving some biological problems.

As used herein, a "training set" is a set of data used in various areas of information science to discover potentially predictive relationships. Training sets are used in artificial intelligence, machine learning, genetic programming, intelligent systems, and statistics. In all these fields, a training set has much the same role and is often used in conjunction with a test set.

As used herein, a "test set" is a set of data used in various areas of information science to assess the strength and utility of a predictive relationship. Test sets are used in artificial intelligence, machine learning, genetic programming, intelligent systems, and statistics. In all these fields, a test set has much the same role.

"Sensitivity" and "specificity" are statistical measures of the performance of a binary classification test. Sensitivity measures the proportion of actual positives which are correctly identified as such (e.g. the percentage of sick people who are correctly identified as having the condition). Specificity measures the proportion of negatives which are correctly identified (e.g. the percentage of healthy people who are correctly identified as not having the condition). These two measures are closely related to the concepts of type I and type II errors. A theoretical, optimal prediction can achieve 100% sensitivity (i.e. predict all people from the sick group as sick) and 100% specificity (i.e. not predict anyone from the healthy group as sick). A specificity of 100% means that the test recognizes all actual negatives—for example, in a test for a certain disease, all disease free people will be recognized as disease free. A sensitivity of 100% means that the test recognizes all actual positives—for example, all sick people are recognized as being ill. Thus, in contrast to a high specificity test, negative results in a high sensitivity test are used to rule out the disease. A positive result in a high specificity test can confirm the presence of disease. However, from a theoretical point of view, a 100%-specific test standard can also be ascribed to a 'bogus' test kit whereby the test simply always indicates negative. Therefore the specificity alone does not tell us how well the test recognizes positive cases. A knowledge of sensitivity is also required. For any test, there is usually a trade-off between the measures. For example, in a diagnostic assay in which one is testing for people who have a certain condition, the assay may be set to overlook a certain percentage of sick people who are correctly identified as having the condition (low specificity), in order to reduce the risk of missing the percentage of healthy people who are correctly identified as not having the condition (high sensitivity). This trade-off can be represented graphically using a receiver operating characteristic (ROC) curve.

The "accuracy" of a measurement system is the degree of closeness of measurements of a quantity to its actual (true) value. The "precision" of a measurement system, also called reproducibility or repeatability, is the degree to which repeated measurements under unchanged conditions show the same results. Although the two words can be synonymous in colloquial use, they are deliberately contrasted in the context of the scientific method. A measurement system can be accurate but not precise, precise but not accurate, neither, or both. For example, if an experiment contains a systematic error, then increasing the sample size generally increases precision but does not improve accuracy. Eliminating the systematic error improves accuracy but does not change precision.

The term "predictability" (also called banality) is the degree to which a correct prediction or forecast of a system's state can be made either qualitatively or quantitatively. Perfect predictability implies strict determinism, but lack of predictability does not necessarily imply lack of determinism. Limitations on predictability could be caused by factors such as a lack of information or excessive complexity.

In some aspects, a method of the present invention may predict the teratogenicity of a test compound with at least about 80% accuracy, at least about 85% accuracy, at least about 90% accuracy, or at least about 95% accuracy.

In some aspects, a method of the present invention may predict the teratogenicity of a test compound with at least about 80% sensitivity, at least about 85% sensitivity, at least about 90% sensitivity, or at least about 95% sensitivity.

In some aspects, a method of the present invention may predict the teratogenicity of a test compound with at least about 80% specificity, at least about 85% specificity, at least about 90% specificity, or at least about 95% specificity.

In some aspects, the methods described herein may utilize cystine determinations alone, or cystine in combinations with any of a variety of other metabolites, including, but not limited to one or more of the metabolites described herein. For example, a determination of a fold change in cystine alone can be used to classify teratogens, using a threshold of at least a 10% increase relative to the reference treatment.

In some aspects, the methods described herein may utilize ornithine determinations alone, ornithine in combinations with any of a variety of other metabolites, including, but not limited to one or more of the metabolites described herein. For example, a determination of a fold change in ornithine alone can be used to classify teratogens, using a threshold of about a 20% increase and/or an 18.5% decrease relative to the reference treatment.

In addition to determining altered ratios in the fold changes of ornithine to cystine, asymmetric dimethylarginine (ADMA) to cystine, and/or cystathionine to cystine, the accuracy of the methods described herein may be improved by further determining the fold change in one or more additional metabolites associated with hSLCs cultured in the presence of the test compound in comparison with hSLCs cultured in the absence of the test compound.

In some embodiments, a method may further include a determination of the ratio of the fold change in arginine, or fragment, adduct, deduct or loss thereof, to the fold change in ADMA, or fragment, adduct, deduct or loss thereof. In some aspects, a ratio of less than at least about 0.9 or greater than at least about 1.1 is indicative of the teratogenicity of the test compound and a ratio of greater than at least about 0.9 and less than at least about 1.1 is indicative of the non-teratogenicity of the test compound. See, for example, PCT/US2011/029471 and U.S. patent application Ser. No. 13/069,326 ("Predicting Human Developmental Toxicity of Pharmaceuticals Using Human Stem-Like Cells and Metabolomics"), West et al., 2010, Toxicol Appl Pharmacol; 247(1):18-27, and Kleinstreuer et al., 2011, Toxicol Appl Pharmacol; 257(1):111-121.

Additional metabolites may include, for example, one or more additional metabolites, two or more additional metabolites, three or more additional metabolites, four or more additional metabolites, five or more additional metabolites, six or more additional metabolites, seven or more additional metabolites, eight or more additional metabolites, nine or more additional metabolites, ten or more additional metabolites, eleven or more additional metabolites, twelve or more additional metabolites, thirteen or more additional metabolites, fourteen or more additional metabolites, or fifteen or more additional metabolites.

One or more additional metabolite may include a metabolite of a metabolic pathway selected from, for example, an alanine, aspartate and glutamate metabolic network; an arginine and proline metabolic network; an ascorbate and aldarate metabolic network; a citrate cycle; a cysteine and methionine metabolic network; a galactose metabolic network; a glutathione metabolic network; a glyoxylate and dicarboxylate metabolic network; a nicotinate and nicotinamide metabolic network; a pantothenate and coenzyme A biosynthesis pathway; a pentose and glucoronate interconversions pathway; a pentose phosphate pathway; a propanoate metabolic network; a pyruvate metabolic network; and/or a vitamin B6 metabolic network.

For example, one or additional metabolite may include a metabolite of the pantothenate and coenzyme A biosynthesis pathway, such as, for example, pyruvate, L-valine, dimethylmalate, pantoate, patothenate, phosphorpatothenoyl-L-cyteine, 5,6-dihydrouracil, N-carbamoyl-β-alanine, and/or coenzyme A.

For example, one or additional metabolite may include a metabolite of the glutathione metabolic network, such as, for example, 5-oxoproline, L-glutamate, glycine, L-γ-glutamylcysteine, glycine, dehydroascorbate, glutathionyl spermine, and/or L-ornithine.

For example, one or additional metabolite may include a metabolite of the arginine and proline metabolic network, such as, for example, pyruvate, dimethlarginine, L-arginine, L-citrulline, glutamine, aspartate, L-argosuccinate, guanidino-acetate-phosphate, fumarate, sarcosine, 2-oxoarginine, pyruvate, 5-amino-pentanoate, linatine, pyrrole-2-carbosylate, putrescine, 6-oxo-1,4,5,6-tetrahydronicotinate, 2,6-dihydroxynictinate, fumarate, and/or GABA.

For example, one or additional metabolite may include a metabolite of the nicotinate and nicotinamide metabolic network, such as, for example, 6-oxo-1,4,5,6-tetrahydronicotinate, 2,6-dihydroxynictinate, and/or fumarate.

For example, additional metabolites may include one or more, two or more, three or more, four or more, or five or more additional metabolites selected from cystine, N1-acetyl spermidine, asymmetric dimethylarginine, cystathionine, 2'-deoxyuridine, GABA, malic acid, succinic acid, and aspartic acid.

For example, additional metabolites may include any one or more, any two or more, any three or more, any four or more, any five or more, any six or more, any seven or more, any eight or more, any nine or more, any ten or more, any eleven or more, any twelve or more, any thirteen or more, or any fourteen or more of the additional metabolites selected from methyl sulfonylacetonitrile; aspartic acid, N-acetyl spermidine; dimethyl-L-arginine; L-cystathionine; GABA; fumaric acid; valine; succinic acid; aspartic acid; pantoic acid; the metabolite having m/z of 215.1387, RT of 466, and ESI(+) polarity; the metabolite having m/z of 234.8904, RT of 246, and ESI(+) polarity; the metabolite having m/z of 251.0666, RT of 105, and ESI(+) polarity; and the metabolite having m/z of 403.0839, RT of 653, and ESI(+) polarity. In some aspects, all fold changes in fifteen metabolites is determined. See, Table 11 of PCT/US2011/029471 and U.S. patent application Ser. No. 13/069,326 ("Predicting Human Developmental Toxicity of Pharmaceuticals Using Human Stem-Like Cells and Metabolomics"), each of which is hereby incorporated by reference in its entirety.

The hSLC and metabolomics based methods of the present invention offer a significant advantage over other studies that use mouse or zebra fish-based models to determine toxicity and teratogenicity of chemical compounds.

The methods of the present invention may be used for classifying a test compound as a teratogen or a non-teratogen, for predicting the teratogenicity of a test compound, and/or for validating a test compound as a teratogen. The methods of the present invention may also serve as a high throughput screening tool in preclinical phases of drug discovery. In addition, this approach can be used to detect detrimental effects of environmental (heavy metals, industrial waste products) and nutritional chemicals (such as alcohol) on human development. Further, the methods of this invention can assist pharmaceutical, biotechnology and environmental agencies on decision-making towards development of compounds and critical doses for human exposure. The integration of chemical biology to embryonic stem cell technology also offers unique opportunities to strengthen understanding of human development and disease. Metabolomics of cells differentiated from hSLCs should serve similar roles and be useful for elucidating mechanisms of toxicity and disease with greater sensitivity for particular cell or tissue types, and in a human-specific manner.

Biomarker portfolios produced using the hSLC-dependent methods of this invention may also be used in high throughput screening methods for preclinical assessment of drug candidates and lead compounds in drug discovery. This aspect of the inventive methods produces minimal impact on industry resources in comparison to current developmental toxicology models, since implementation of this technology does not require experimental animals. The resulting positive impact on productivity enables research teams in the pharmaceutical industry to select and advance compounds into exploratory development with greater confidence and decreased risk of encountering adverse developmental effects.

The present invention includes a kit for identifying and/or measuring one or more metabolites. In some aspects, the kit may be for the determination of a metabolite by a physical separation method. In some aspects, the kit may be for the determination of a metabolite by a methodology other than a physical separation method, such as for example, a colorimetric, enzymatic, immunological methodology. In some aspects an assay kit may also include one or more appropriate negative controls and/or positive controls. Kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a polypeptide. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

In some aspects, a kit may be a packaged combination comprising the basic elements of a first container comprising, in solid form, a specific set of one or more purified metabolites, as described herein, and a second container comprising a physiologically suitable buffer for resuspending the specific subset of purified metabolites.

The present invention is illustrated by the following examples. It is to be understood that the particular examples, materials, amounts, and procedures are to be interpreted broadly in accordance with the scope and spirit of the invention as set forth herein.

EXAMPLES

Example 1

Establishment and Assessment of a New Human Embryonic Stem Cell-Based Biomarker Assay for Developmental Toxicity Screening With this example a metabolic biomarker-based in vitro assay utilizing human embryonic stem (hES) cells was developed to identify the concentration of test compounds that perturbs cellular metabolism in a manner indicative of teratogenicity. This assay is designed to aid the early discovery-phase detection of potential human developmental toxicants. In this study, metabolomic data from hES cell culture media was used to assess potential biomarkers for development of a rapid in vitro teratogenicity assay. hES cells were treated with pharmaceuticals of known human teratogenicity at a concentration equivalent to their published human peak therapeutic plasma concentration. Two metabolite biomarkers (ornithine and cystine) were identified as indicators of developmental toxicity. A targeted exposure-based biomarker assay using these metabolites, along with a cytotoxicity endpoint, was then developed using a 9-point dose response curve. The predictivity of the new assay was evaluated using a separate set of test compounds. To illustrate how the assay could be applied to compounds of unknown potential for developmental toxicity, an additional 10 compounds were evaluated that do not have data on human exposure during pregnancy, but have shown positive results in animal developmental toxicity studies. The new assay identified the potential developmental toxicants in the test set with 77% accuracy (57% sensitivity, 100% specificity). The assay had a high concordance (>75%) with existing in vivo models, demonstrating that the new assay can predict the developmental toxicity potential of new compounds as part of discovery phase testing and provide a signal as to the likely outcome of required in vivo tests.

This example describes the development of a rapid, reproducible, biomarker-based screen for developmental toxicity testing designed to identify the exposure level at which a test compound perturbs metabolism in a manner predictive of developmental toxicity. Perturbation of two metabolites, ornithine and cystine, in response to the test compound was assessed across nine independent experimental replications to ensure repeatability across experiments and liquid chromatography high resolution mass spectrometry (LC-HRMS) systems. Using the ornithine/cystine ratio (o/c ratio), we developed a rapid, targeted assay that measured changes in metabolism and cellular viability across a 9-point dose response curve to determine the exposure level at which a test compound perturbs metabolism in a manner associated with developmental toxicity potential. To assess the predictivity of the assay for known human teratogens in the training and test sets of compounds, the exposure level where a compound was predicted to have developmental toxicity potential was scored against the compound's human peak plasma in vivo concentration ($C_{max}$) following therapeutic doses. The $C_{max}$ value in this case is used as a benchmark exposure level to aid in interpreting the performance of the assay as it is the highest concentration a human would normally be exposed to under therapeutic circumstances and we would expect to detect developmental toxicity at this exposure level.

However, application of the assay in the discovery stage of a compound's development would not require this $C_{max}$ information, and a test compound's teratogenic potential is based on the exposure level at which a test compound perturbs metabolism in a manner indicative of teratogenicity. The design and sensitivity of the assay allows for identification of teratogenic potential at non-cytotoxic levels of the test compound, by negating the confounding effects of changes in metabolite abundance due strictly to cytotoxicity. The ability to identify developmental toxicity in the absence of cytotoxicity at a variety of exposure levels is a key strength of the assay and distinguishes it from existing in vitro assays.

Useful Terms and Definitions

Teratogenicity Threshold. A threshold of metabolic perturbation that is associated with the potential for teratogenesis. The threshold was empirically determined to be 0.88 for the targeted biomarker assay using the training set results. This threshold was applied to all test set and unknown compounds evaluated using the assay.

Ornithine/Cystine Ratio (O/C Ratio). The fold change of ornithine (Orn) for treatment x divided by the fold change of cystine (Cyss) for treatment x.

$$O/C \text{ Ratio} = \frac{(Orn_x / Orn_{DMSO})}{(Cyss_x / Cyss_{DMSO})}$$

Teratogenicity Potential. Interpolated exposure level (concentration) of a test compound where the dose response curve for the o/c ratio or cell viability crosses the teratogenicity threshold. Exposure levels greater than this concentration are associated with teratogenicity.

Accuracy. Number of correct predictions divided by the number test compounds evaluated.

Sensitivity. Detection of teratogens, True Positives/(False Negatives+True Positives).

Specificity. Detection of non-teratogens, True Negatives/(True Negatives+False Positives).

Training Set. Set of compounds that have well established human developmental toxicity information used to identify biomarkers of developmental toxicity. This set of compounds was tested in both phases of the study and used to set the teratogenicity threshold.

Test Set. Set of compounds with well-established human developmental toxicity information that were not used to identify the biomarkers, but used to evaluate the predictivity of the biomarkers of developmental toxicity. This set of compounds was used to evaluate the performance of the targeted biomarker assay and the teratogenicity threshold set using the training set.

Application Set. Set of compounds with poorly defined human developmental toxicity information used to demonstrate application of the assay. These compounds are not classified as a teratogen or non-teratogen based on their $C_{max}$ since human teratogenicity is unknown at this concentration.

Materials and Methods

Development and evaluation of the targeted biomarker-based assay was conducted in two phases. In the first phase (Phase 1), the predictive potential of two previously identified predictive biomarkers (ornithine and cystine, Kleinstreuer et al., 2011, Toxicol Appl Pharmacol; 257:111-121) was characterized across nine independent experimental replications (experimental blocks) of the training set using untargeted metabolomic methods. In the second phase (Phase 2), the predictive biomarkers were used to develop a rapid turnaround, targeted, exposure-based assay for compound prioritization based on teratogenicity potential. The predictivity of the new assay was evaluated using the original training set as well as an independent test set of compounds.

Test Chemical Selection and Classification. A total of 46 compounds were used to evaluate the ability of ornithine, cystine and the o/c ratio to predict developmental toxicity in two experimental phases. These 46 compounds were divided into three groups, named the training, test, and application sets. The training set was a set of compounds that have well established human developmental toxicity information used to identify biomarkers of developmental toxicity. The test set was a set of compounds with well-established human developmental toxicity information that were not used to identify the biomarkers, but used to evaluate the predictivity of the biomarkers of developmental toxicity. The application set was a set of compounds with poorly defined human developmental toxicity information used to demonstrate application of the assay. These compounds are not classified as a teratogen or non-teratogen based on their $C_{max}$ since human teratogenicity is unknown at this concentration.

The training set consisted of 23 well characterized pharmaceutical compounds (11 known human non-teratogens and 12 known human teratogens, Table 2) and was previously used to build a computational model and identify biomarkers predictive of teratogenicity (Kleinstreuer et al., 2011, Toxicol Appl Pharmacol; 257:111-121). This training set was utilized in both experimental phases. To assess the predictive capacity of the targeted biomarker assay developed in these studies, an additional test set of 13 well characterized pharmaceutical compounds (6 known human non-teratogens and 7 known human teratogens, Table 3) was used in the second experimental phase to evaluate the predictivity of the new assay. The final set of compounds (the application set, Table 4) consists of 10 compounds that do not have conclusive developmental toxicity data available on exposure during human pregnancy, but do have animal data available on developmental toxicity potential. A two-class system of compound classification (teratogen and non-teratogen) was applied for assay development, focusing the teratogenicity classification strictly on observed human risk associated with each chemical. Compounds were purchased from Sigma-Aldrich (St. Louis, Mo.), except for amprenavir, bosentan, entacapone (Toronto Research Chemicals, Toronto, Ontario, Canada), lapatinib (Chemie Tek, Indianapolis, Ind.), cidovofir and ramelteon (Selleck Chemicals, Houston, Tex.).

TABLE 1

Description of the Training Set Compounds.

| Compound | Pharmacology/Chemical Class | FDA Pregnancy Category[a] | Preclinical in vivo and known human developmental effects[b] |
|---|---|---|---|
| Human Non-teratogens | | | |
| Ascorbic Acid | Vitamin | A | None |
| Caffeine | Central Nervous System Stimulant | C | Low Doses: None; High Doses: Limb, craniofacial, embryo toxicity[c] |
| Diphenhydramine | Antihistamine/H1 histamine receptor antagonist | B | None |
| Doxylamine | Antihistamine/H1 histamine receptor antagonist | B | None |
| Folic Acid | Vitamin | A | None |
| Isoniazid | Antibacterial/Antitubercular | C | None |
| Levothyroxine | Synthetic hormone | A | None |
| Penicillin G | Antibiotic | B | None |
| Retinol | Vitamin | C | Low Doses: None; High Doses: Craniofacial, central nervous system, cardiovascular, skeletal |
| Saccharin | Artificial Sweetener | A | None |
| Thiamine | Vitamin | A | None |
| Human Teratogens | | | |
| 13-cis Retinoic Acid | RAR/RXR ligand | X | Craniofacial, limb, central nervous system, cardiovascular, skeletal |
| 5-Fluorouracil | Antineoplastic/Antimetabolite | D | Craniofacial, central nervous system, skeletal |
| All-trans Retinoic Acid | RAR/RXR ligand | D | Craniofacial, limb, central nervous system, cardiovascular, skeletal, embryo toxicity[c] |
| Busulfan | Antineoplastic/Alkylating | D | Craniofacial, limb, embryo toxicity[c] |
| Carbamazepine | Anticonvulsant | D | Craniofacial, central nervous system, cardiovascular |
| Cytosine Arabinoside | Antineoplastic/Antimetabolite | D | Limb |
| Diphenylhydantoin | Anticonvulsant | D | Craniofacial, limb, cardiovascular, neurobehavioral |
| Hydroxyurea | Antineoplastic/Enzyme Inhibitor | D | Central nervous system, craniofacial, limb, cardiovascular, embryo toxicity[c] |
| Methotrexate | Antineoplastic/Dihydrofolate acid reductase inhibitor | X | Craniofacial, limb, skeletal, central nervous system, embryo toxicity[c] |
| Thalidomide | Immunomodulant | X | Craniofacial, cardiovascular, limb, embryo toxicity[c] |
| Valproic Acid | Anticonvulsant/GABA inhibitor | D | Central nervous system, craniofacial, cardiovascular, skeletal, neurobehavioral, embryo toxicity[c] |
| Warfarin | Anticoagulant | X | Central nervous system, craniofacial, skeletal, embryo toxicity[c] |

[a]FDA classification requirements described in Shuren (2008, *Federal Register*; 73: 30831-30868).
[b]The preclinical in vivo and known human developmental effects were summarized from the Teratogen Information System (TERIS, see the worldwide web at depts.washington.edu/terisweb/teris/) and Briggs et al. (2011, "Drugs in pregnancy and lactation," 9th ed. Philadelphia: Lippincott Williams & Wilkins).
[c]Embryo toxicity in addition to teratogenic effects (e.g., growth retardation, embryo lethality).

TABLE 2

Description of the Test Set Compounds.

| Compound | Pharmacology/Chemical Class | FDA Pregnancy Category[a] | Preclinical in vivo and known human developmental effects[b] |
|---|---|---|---|
| Human Non-teratogens | | | |
| Acetaminophen | Analgesic | B | None |
| Acycloguanosine | Antiviral | B | None |
| Amoxicillin | Antibiotic | B | None |
| Loratadine | Antihistamine/H1 histamine receptor antagonist | B | None |
| Metoclopramide | Antiemetic | B | None |
| Sitagliptin | Hypoglycemic | B | Low doses: None; High doses: Skeletal |
| Human Teratogens | | | |
| Aminopterin | Antineoplastic/Dihydrofolate acid reductase inhibitor | X | Craniofacial, limb, skeletal, central nervous system |
| Bosentan | Antihypertensive | X | Craniofacial, cardiovascular |
| D-Penicillamine | Chelator | D | Skeletal |
| Everolimus | Immunosuppressive | D | Skeletal, embryo toxicity[c] |
| Lapatinib | Antineoplastic/Protein Kinase Inhibitors | D | Skeletal, embryo toxicity[c] |
| Lovastatin | Anticholesteremic | X | Skeletal, embryo toxicity[c] |
| ThioTEPA | Antineoplastic/Alkylating | D | Skeletal, embryo toxicity[c] |

[a]FDA classification requirements described in Shuren (2008, *Federal Register*; 73: 30831-30868).
[b]The preclinical in vivo and known human developmental effects were summarized from the Teratogen Information System (TERIS, see the worldwide web at depts.washington.edu/terisweb/teris/) and Briggs et al. (2011, "Drugs in pregnancy and lactation," 9th ed. Philadelphia: Lippincott Williams & Wilkins).
[c]Embryo toxicity in addition to teratogenic effects (e.g., growth retardation, embryo lethality).

TABLE 3

Description of the Application Set Compounds.

| Compound | Pharmacology/Chemical Class | FDA Pregnancy Category[a] | Preclinical in vivo developmental effects[b] |
|---|---|---|---|
| 6-Aminonicotinamide | Nicotinic Acid Antagonist | NA | Craniofacial |
| Abacavir | Anti-HIV | C | Skeletal, embryo toxicity[c] |
| Adefovir dipivoxil | Antiviral | C | None |
| Amprenavir | Anti-HIV | C | Skeletal, embryo toxicity[c] |
| Artesunate | Antimalarial | NA | Cardiovascular, skeletal, embryo toxicity[c,b] |
| Cidofovir | Antiviral | C | None |
| Entacapone | Antiparkinson | C | Eye defects |
| Fluoxetine | Serotonin reuptake inhibitor | C | Embryo toxicity[c] |
| Ramelteon | Sedative/Hypnotics | C | None |
| Rosiglitazone | Hypoglycemic | C | Embryo toxicity[c] |

[a]FDA classification requirements described in Shuren (2008, *Federal Register*; 73: 30831-30868).
[b]The preclinical in vivo and known human developmental effects were summarized from the Teratogen Information System (TERIS, see the worldwide web at depts.washington.edu/terisweb/teris/) and Briggs et al. (2011, "Drugs in pregnancy and lactation," 9th ed. Philadelphia: Lippincott Williams & Wilkins).
[c]Embryo toxicity in addition to teratogenic effects (e.g., growth retardation, embryo lethality).
[d]Clark, 2009, *Reprod Toxicol*; 28: 285-296.

Undifferentiated hES Cell Line Maintenance (Phases 1 and 2). WA09 hES cells were obtained from the WiCell Research Institute (Madison, Wis.) and were maintained in feeder free conditions using mTeSR1 media (StemCell Technologies, Inc., Vancouver, BC, Canada) on hESC-qualified Matrigel (BD Biosciences, San Jose, Calif.) coated 6-well plates. To maintain the undifferentiated stem cell population, differentiated colonies were removed daily through aspiration and media was replaced. Additionally, the hES cells were only used in experiments up to passage 40 and were karyotyped approximately every 10 passages to minimize and monitor the potential for genetic instability. hES cells were passaged at 90-95% confluency (approximately every 7 days) using Versene (Life Technologies, Grand Island, N.Y.). Cell cultures were maintained at 37° C. under 5% $CO_2$.

96-well hES Cell Plating (Phases 1 and 2). All experimental treatments were carried out in 96-well plates. To minimize plating variability and increase reproducibility, hES cells were plated as a single cell suspension and maintained in an undifferentiated state during compound exposure. Prior to plating in the 96-well plates, hES cells were removed from a 6-well plate using TrypLE (Life Technologies). The cells were washed with DMEM/F12 (Life Technologies) and resuspended in mTeSR1 containing 10 µM Y27632 Rho-associated kinase (ROCK) inhibitor (Merck KGaA/Calbiochem, Darmstadt, Germany). The ROCK inhibitor is added to the plating media to increase plating efficiency by decreasing dissociation-induced apoptosis. The inner 60 wells of hESC-qualified Matrigel coated 96-well plates were seeded at a density of 100,000 cells per well. The outer wells of the plate contained an equal volume media to minimize differences in humidity across the plate. Compound exposure began 24 hours after plating.

Phase I hES Cell Compound Exposure. hES cells were treated with a test compound at a single concentration equivalent to the compound's published therapeutic $C_{max}$. The therapeutic $C_{max}$ was used because it is considered to be a physiologically relevant exposure level and has been correlated with the developmental effect of the compound (National Research Council, 2000, "Scientific frontiers in developmental toxicology and risk assessment," Washington, D.C.: The National Academies Press). For six compounds (5-fluorouracil, aminopterin, busulfan, cytosine arabinoside, hydroxyurea and methotrexate) an experimentally determined $IC_{30}$ was used in place of the $C_{max}$ value due to greater than 30% cytotoxicity at the $C_{max}$ exposure level. This was done to ensure that enough cells were present at the time of sample collection to provide a signal for LC-HRMS analysis. For test compound exposure, all compound stock solutions, with the exception of valproic acid, were made with DMSO (Sigma-Aldrich). Valproic acid was insoluble in DMSO at the concentrations used in this study, so it was diluted in mTeSR1 containing 0.1% DMSO. Each 96-well plate included media controls with and without test compound, 0.1% DMSO solvent control cells and cells exposed to a single concentration of eight different test compounds (FIG. 1A). Media controls were included on each plate to assess the impact of test compound on the sample matrix. hES cells were exposed to the test compound for 72 hours, with media and test compound replacement every 24 hours. Cells were monitored throughout the treatment period to ensure that no differentiation was occurring. After 72 hours of treatment, the spent media from the final 24-hour treatment period was collected and added to acetonitrile (Sigma-Aldrich, final acetonitrile concentration 40%), to halt metabolic processes and precipitate proteins from solution. Individual wells from each 96-well plate were collected and analyzed as separate samples. These samples were then stored at −80° C. until prepared for LC-HRMS analysis. Cell viability was assessed using the CellTiter-Fluor Cell Viability Assay as per the manufacturer's instructions (Promega, Madison, Wis.). Quality control parameters were set such that if the coefficient of variation (CV) for the viability relative fluorescent units (RFU) of the 6 cellular samples in a treatment exceeded 10% and no outliers were identified using the Grubb's test (see the worldwide web at graphpad.com/quickcalcs/Grubbs1.cfm), analysis was halted for that compound and the cell culture experiment was repeated. If outliers were present, the outlier sample was removed from analysis. If the CV for the DMSO control cell samples on a plate were outside of the quality control parameters, the entire plate was repeated. hES cell exposure to each of the 23 compounds was replicated a total of nine times.

Figure 1B:
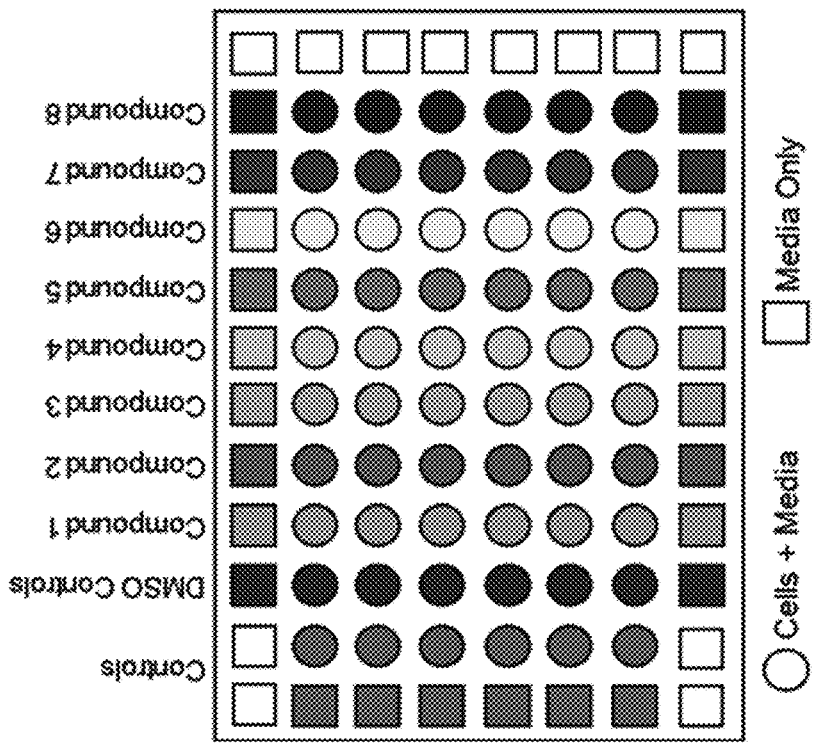

Phase 2 hES Cell Compound Exposure. The predictivity of the targeted biomarker assay was evaluated in the original training set as well as an independent test set (Tables 2 and 3). The assay was additionally applied to the application set of compounds (Table 4) to demonstrate utility when human teratogenicity is unknown. The standard compound exposure levels used for most compounds were nine, 3-fold dilutions ranging from 0.04 µM-300 µM (FIG. 1B). The exposure range for valproic acid was increased to 4 µM-30,000 µM because its therapeutic $C_{max}$ was outside the standard exposure range. Compounds that were cytotoxic at concentrations below 1 µM were repeated at lower exposure levels (0.001 µM 10 µM). A stock solution of each test compound was prepared in 100% DMSO at a concentration of 1000 times the highest exposure level, with the exception of ascorbic acid, folic acid, and valproic acid. These three compounds were completely insoluble in DMSO and stocks were prepared in mTeSR1 containing 0.1% DMSO. The stock solution was diluted 1:1000 in mTeSR1 media and subsequent dilutions were performed in mTeSR1 containing 0.1% DMSO such that the final concentration of DMSO was 0.1% in all treatments. hES cells were treated for 72 hours and spent media from the last 24-hour treatment period was collected and added to acetonitrile containing $^{13}C_6$ labeled arginine (Cambridge Isotope Laboratories, Andover, Md.) as described under Phase 1. Spent media samples were stored at −80° C. until prepared for LC-HRMS analysis. Cell viability was assessed using the CellTiter-Fluor Cell Viability Assay. A quality control step was included with criteria that the CV of the measured viability RFU of the DMSO control cells could not exceed 10% for a plate to undergo LC-HRMS analysis. A dose response curve was fit to the reference treatment (0.1% DMSO treated control cells) normalized data (Viability $RFU_{Trt\ x}$/Viability $RFU_{DMSO}$) using a four-parameter log-logistic model with the R package "drc" (Ritz and Streibig, 2005, *J Statistical Software;* 12:1-22).

Sample Preparation (Phases 1 and 2). High molecular weight constituents (>10 KDa) of the spent media samples were removed using a Millipore Multiscreen Ultracel-10 filter plate (EMD Millipore, Billerica, Mass.). Prior to sample filtration, the filter plate was washed with 0.1% NaOH to remove a known contaminant polymer. The plate was then rinsed twice with HPLC-grade water to remove residual polymers and NaOH. Spent media samples were added to the washed filter plate. In Phase 1, samples were spiked with $^{13}C_6$ labeled arginine. Samples were centrifuged at 2,000×g at 4° C. for 200 minutes. The filtrate was collected and concentrated overnight in a Savant High Capacity Speedvac Plus Concentrator. The concentrated sample was resolubilized in a 1:1 0.1% formic acid in water: 0.1% formic acid in acetonitrile mixture containing $^{13}C_5$ labeled glutamic acid (Cambridge Isotope Laboratories). The $^{13}C$ labeled compounds were used as internal standards to track preparatory efficiency and track LC-HRMS performance.

Phase 1 Mass Spectrometry. LC-HRMS data was acquired for nine biological replications on three separate LC-HRMS systems with three replications evaluated on each system. Each system consisted of an Agilent 1290 Infinity LC system interfaced either with an Agilent G6520A QTOF high resolution mass spectrometer (QTOF HRMS), an Agilent G6530A QTOF HRMS, or an Agilent G6224A TOF HRMS system (Agilent Technologies, Santa Clara, Calif.). To facilitate separation of biological small molecules with a wide range of structures and to allow increased retention of hydrophilic species, Hydrophilic Interaction Liquid Chromatography (HILIC) was utilized. A Luna HILIC column (Phenomenex, Torrance, Calif.) with dimensions 3×100 mm and 3 µm particle size was used and maintained at 30° C. Sample (2 µL) was injected and the data acquisition time was 23 minutes (min) at a flow rate of 0.5 ml/min, using a 17 min solvent gradient with 0.1% formic acid in water (Solvent A) and 0.1% formic acid in acetonitrile (Solvent B). Electrospray ionization was employed using a dual ESI source. The scan range of the instrument was 70-1600 Da. Data acquisition was performed with MassHunter Acquisition software (version B 04.00, Agilent Technologies) using high-resolution exact mass conditions and each set of samples was run first under ESI positive polarity then under ESI negative polarity conditions.

Phase 2 Mass Spectrometry. Data was acquired to assess the performance of the targeted biomarker assay using two instrument platforms. Ultra high performance liquid chromatography (UPLC)-HRMS data acquisition for each compound was performed using one of two systems. System 1 consisted of an Agilent 1290 Infinity LC system interfaced with an Agilent G6520A QTOF HRMS. System 2 used the same model LC system interfaced with an Agilent G6224A TOF HRMS. A Waters Acquity UPLC BEH Amide 2.1×50 mm 1.7 μm particle size column (Waters, Milford, Mass.) maintained at 40° C. was applied for separation of metabolites. A solvent gradient with 0.1% formic acid in water (Solvent A) and 0.1% formic acid in acetonitrile (Solvent B) at a flow rate of 1.0 ml/min was used and 2 μL of sample was injected. Electrospray ionization was employed using a dual ESI source operated in positive ionization mode only. The mass range of the instrument was set to 60-1600 Da and data was acquired over 6.5 min using MassHunter Acquisition software (version B 04.00). Identification of cystine and ornithine metabolites in samples was previously confirmed by comparison of their collision-induced dissociation mass spectra to reference standards (Sigma-Aldrich).

Peak Detection (Phases 1 and 2). Agilent raw data files were converted to the open source mzData file format using MassHunter Qualitative Analysis software version 5.0 (Agilent Technologies). During the conversion process, deisotoping (+1 charge state only) was performed on the centroid data and peaks with an absolute height less than 200 were excluded from analysis. Peak picking and feature creation were performed using the R package "xcms" (Smith et al., 2006, *Anal Chem;* 78:779-787). Mass features (peaks) were detected using the centwave algorithm. Deviations in retention times were corrected using the obiwarp algorithm that is based on a non-linear clustering approach to align the data from the LC-MS samples. Mass feature bins or groups were generated using a density based grouping algorithm. After the data had been grouped into mass features, missing features were integrated based on retention time and mass range of a feature bin using the iterative peak filling. Feature intensity is based on the Mexican hat integration values of the feature extracted ion chromatograms.

Ornithine/Cystine Ratio Calculation. In both phases of the study, every 96-well plate of samples contained a reference treatment (0.1% DMSO) to allow compensation for the differences in LC-MS instrument response over time. Relative fold changes were calculated for each metabolite by dividing the integrated area of each sample within a treatment level by the median integrated area of the reference treatment (DMSO) samples to produce a normalized value for both metabolites in each sample within a plate of cell culture samples. The o/c ratio was calculated for each sample in a treatment by dividing the reference normalized value of ornithine by the reference normalized value of cystine. In Phase 2, a four-parameter log-logistic model of dose response was fit using the mean o/c ratio value of each concentration using the R package "drc" (Ritz and Streibig, 2005, *J Statistical Software;* 12:1-22).

Teratogenicity Threshold Selection (Phases 1 and 2). Classification of teratogenicity was based on the premise that a threshold of metabolic perturbation could be identified for individual metabolites that is associated with developmental toxicity. This threshold of metabolic change is called the teratogenicity threshold and is a measure of the magnitude of metabolic perturbation required to differentiate teratogens from non-teratogens. The teratogenicity threshold was empirically generated for ornithine, cystine, and the o/c ratio by iteration through a range from 10% to 25% change, to identify a one-sided or two-sided asymmetrical threshold that was able to classify the training set with the greatest accuracy and highest sensitivity. In the case of a tie in classification accuracy and sensitivity between one-sided and two-sided thresholds, one-sided thresholds were given priority to favor simplicity. A teratogenicity threshold was determined for each phase of the study, since the assays performed in Phase 1 used only a single concentration of each compound and the targeted biomarker assay developed in Phase 2 utilized an exposure based approach. The teratogenicity threshold was determined in Phase 2 using only the results from the training set. This threshold was then applied to the results from the test and application sets.

Phase 1 Prediction of Developmental Toxicity Potential. A test compound was classified as a developmental toxicant if the mean of the change in the abundance in the treated sample compared to the reference treatment (DMSO) across the nine experimental replications for either metabolite or the o/c ratio exceeded its respective teratogenicity threshold at the concentration tested. The predictive accuracy (correct prediction), sensitivity (true positive rate), and specificity (true negative rate) were based on scoring the predicted result (teratogen or non-teratogen) against the known human teratogenicity of the compound.

Figure 2:
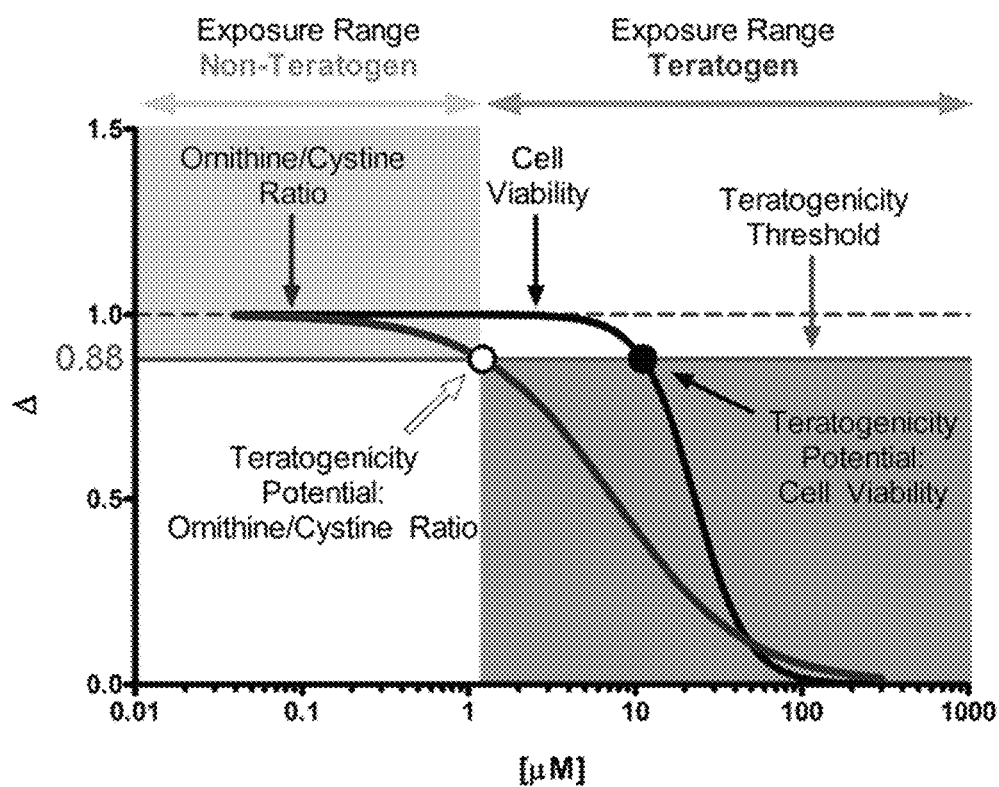
FIG. 2. Graphical representation of the targeted biomarker assay. Human embryonic stem (hES) cells were exposed to nine concentrations of a test compound that spanned four log units. The dose response curve for the ornithine/cystine ratio (o/c ratio; grey curve) and cell viability (black curve) was fit using a four-parameter log-logistic model. The concentration predicted by the interpolated point where the dose response curve of the o/c ratio crosses the teratogenicity threshold (0.88; grey line) indicates the exposure level where a metabolic perturbation has teratogenic potential (i.e., teratogenicity potential: o/c ratio, open circle). The teratogenicity potential concentration from cell viability (filled circle) is the interpolated point where the cell viability dose response curve exceeds the teratogenicity threshold. The teratogenicity potential creates a two-sided toxicity model based on exposure: one where exposure does not perturb metabolism in a manner associated with teratogenicity (lighter shaded box) and another where exposure may cause a potentially teratogenic shift in metabolism (darker shaded box). The x-axis is the concentration (μM) of the compound. Both the cell viability measurements and o/c ratio measurements exist on the same scale represented by $\Delta$ on the y-axis. The y-axis value of the o/c ratio is the ratio of the reference treatment normalized (fold change) values (ornithine/cystine). The y-axis value of the viability measurement is the treatment cell viability RFU normalized to the reference treatment cell viability RFU.

Phase 2 Prediction of Developmental Toxicity Potential. For test compounds with unknown developmental toxicity potential, the targeted biomarker assay is utilized to identify the exposure level where a test compound perturbs metabolism in a manner indicative of teratogenicity and does not require any pharmacokinetic information (e.g., $C_{max}$). FIG. 2 illustrates how the assay is applied in this situation. A test compound is considered to be teratogenic at the exposure level where the o/c ratio exceeds the teratogenicity threshold (red box, FIG. 2). The interpolated concentration from the four-parameter log-logistic model of the o/c ratio or cell viability at the teratogenicity threshold is considered to be the teratogenicity potential exposure level of a test compound (FIG. 2). Exposure levels greater than the teratogenicity potential concentrations are predicted to have developmental toxicity potential.

Figure 3A:
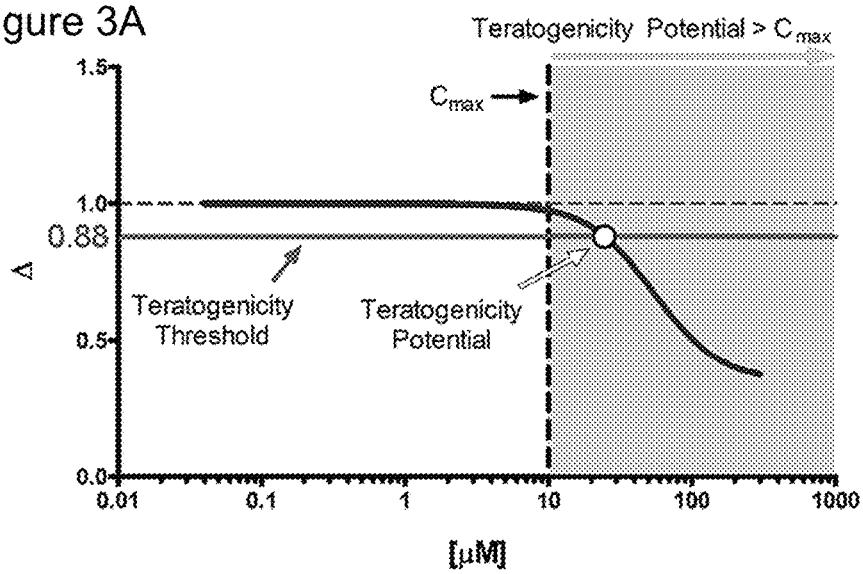
FIGS. 3A and 3B. Graphical representation of the classification scheme for known human teratogens and non-teratogens utilizing the therapeutic $C_{max}$ concentration to set the classification windows. The dose response curve for the o/c ratio (grey curve) was fit using a four-parameter log-logistic model and used to interpolate the concentration where the o/c ratio crosses the teratogenicity threshold (i.e., teratogenicity potential, open circle). A test compound was predicted as a non-teratogen when the teratogenicity potential concentration is higher than the human therapeutic $C_{max}$ (FIG. 3A). A test compound was predicted as a teratogen when the teratogenicity potential concentration is lower than the human therapeutic $C_{max}$ (FIG. 3B). The same logic outlined here is also applied to the viability measurements. The x-axis is the concentration (μM) of the compound. The y-axis value of the o/c ratio is the ratio of the reference treatment normalized (fold change) values (ornithine/cystine).
Figure 3B:
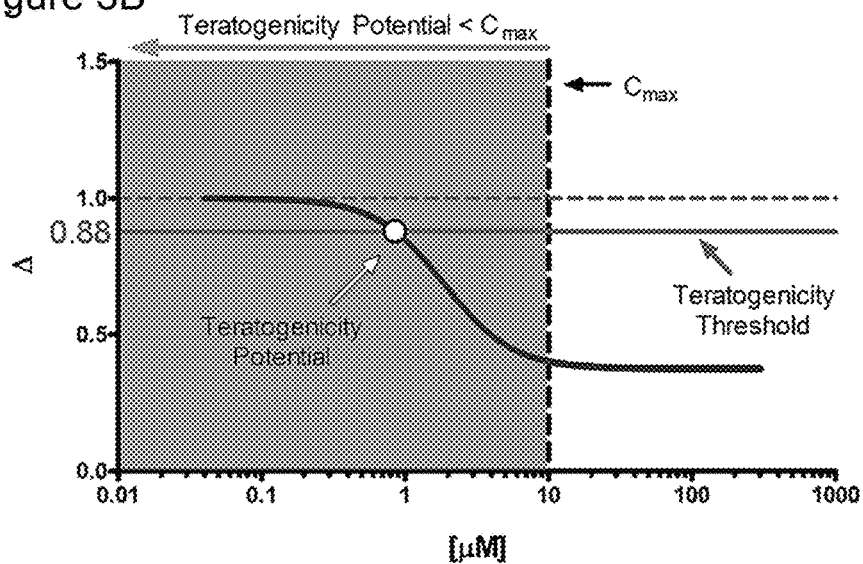

In order to assess the predictivity of the assay in the training and test sets, the teratogenicity potential concentrations determined from the o/c ratio and cell viability were used to classify the teratogenicity of the test compound relative to the human therapeutic $C_{max}$ concentrations. This approach was not applied to the application set since the developmental toxicity potential of these compounds in humans is unknown. The logic of scoring a test compound as a teratogen or non-teratogen using the human therapeutic $C_{max}$ is based on the paradigm that exposure is a critical factor in teratogenesis, and that a known human teratogen would likely perturb cellular metabolism at or below the highest exposure that is likely to occur at the therapeutic circulating levels. If perturbation of the o/c ratio was exhibited at concentrations greater than the compound's $C_{max}$ concentration (FIG. 3A), it was scored as a non-teratogen because perturbation was observed outside of a range likely to be encountered during routine therapy. If a compound exhibited teratogenicity potential at a concentration that was at or below its therapeutic $C_{max}$ it was classified as a teratogen (FIG. 3B), since a metabolic perturbation indicative of teratogenesis was exhibited within the therapeutic concentration range. The teratogenicity potential concentration from cell viability was used to predict the teratogenicity of a compound using the same paradigm. The predictive accuracy, sensitivity, and specificity of the assay were calculated by comparing the predicted result to the known human teratogenicity of a compound.

Comparison of the Targeted Biomarker Assay to Other Developmental Toxicity Tests. A literature review compared the developmental toxicity prediction of the in vivo rodent and rabbit models and three in vitro screens (the European Centre for the Validation of Alternative Methods (ECVAM)-evaluated mouse embryonic stem cell test (mEST), the zebrafish embryotoxicity test (ZET), and the post-implantation rat whole embryo culture (WEC) test) for the compounds tested in the targeted biomarker assay. The predictions made in these assays using each original author's classification methods were used for comparison and the data was not reinterpreted. The other in vitro systems employ a three class classification system (non-, weak/moderate, and strong teratogens; Brown, 2002, *Altern Lab Anim;* 30:177-198), compared to the two class system used in this study. Thus, in order to compare the results from the targeted biomarker assay to other models, the predicted results from these assays needed to be modified to a two class system. Compounds that were predicted to be either weak/moderate or strong teratogens were both labeled as a predicted teratogen. The accuracy, sensitivity and specificity were calculated for each assay by scoring the predicted result against the known human teratogenicity. These values were additionally calculated for the targeted biomarker assay for the specific set of compounds that had been tested in the other model system. Concordance between the targeted biomarker assay and the other above-mentioned models was evaluated by comparing the classification of teratogen or non-teratogen within the common treatments of each comparison.

Results

Phase 1 Model Confirmation and Characterization of Metabolites Predictive of Developmental Toxicity. The first phase of this study was conducted to confirm the predictivity of individual metabolites. Characterization of the predictive metabolites led to the development of the new targeted biomarker assay described in the second phase of this study. Previously, a training set of 23 pharmaceutical compounds (Table 2) was utilized to identify a metabolic signature capable of predicting teratogenicity in vitro (Kleinstreuer et al., 2011, *Toxicol Appl Pharmacol;* 257:111-121). The metabolites that exhibited a statistically significant change upon treatment with teratogens, and lacked a response in non-teratogens, were characterized for their ability to classify developmental toxicants using a simple fold change threshold. Of these metabolites, ornithine and cystine were identified as metabolites that are representative of the previously applied metabolic signature that was highly predictive of developmental toxicity. The capacity of each of these two metabolites to classify developmental toxicants was characterized by determining a teratogenicity threshold based on the fold change of cells treated with a test compound versus the reference treatment (0.1% DMSO) of each metabolite. The threshold was used to evaluate the classification accuracy of each metabolite within the training set.

Ornithine and cystine each exhibited characteristics amenable to rapid evaluation of the potential for a test compound to perturb metabolism in manner consistent with teratogenicity. Both metabolites are highly abundant in spent cell culture media from hES cells and show changes in their abundance in response to treatment that were reproducibly measured on multiple LC-HRMS instruments. To confirm these initial observations, and the reproducibility of the approach, the metabolites were further evaluated in a study that encompassed 9 independent experimental replications (blocks) of the training set. The secreted metabolite ornithine was able to distinguish teratogens from non-teratogens with 83% accuracy (Table 5) using a two-sided threshold consisting of either an 18.5% decrease or 20% increase in accumulation of ornithine (FIG. 4A). Cystine (a media constituent) was the most predictive individual metabolite in classifying teratogens and had an accuracy of 83% (Table 5) using a threshold of a 10% increase relative to the reference treatment (FIG. 4B). Cystine exhibits a significant increase in abundance relative to the reference treatment for most of the teratogens that did not cause cytotoxicity in hES cells (such as hydroxyurea, all-trans retinoic acid, 13-cis retinoic acid, carbamazepine, and thalidomide). Ornithine decreased with cytotoxic treatments (such as 5-fluorouracil, cytosine arabinoside, methotrexate, and valproic acid) but increased when cells were exposed to the related non-cytotoxic teratogens all-trans retinoic acid and 13-cis retinoic acid.

Next, the possibility that the fold changes in the ratio of ornithine and cystine would be more predictive than their individual fold changes was evaluated. When the ornithine fold change was divided by the cystine fold change (i.e., the o/c ratio), the resulting ratio was able to correctly classify 91% (Table 5) of the training set (FIG. 4C) using a teratogenicity threshold of a 12% decrease in the o/c ratio, misclassifying only diphenylhydantoin and warfarin. Compared to the accuracy of ornithine and cystine alone, application of the o/c ratio increased the overall prediction accuracy by 8%, capturing the high specificity of ornithine and high sensitivity of cystine (Table 5) yielding a more accurate classification of teratogenicity.

TABLE 4

Teratogenicity Threshold and Metabolite Model Metrics in the Untargeted Metabolomics-Based Developmental Toxicity Assay.

| Metabolite | Teratogenicity Threshold | Accuracy | Sensitivity | Specificity |
|---|---|---|---|---|
| Ornithine | ≤81.5% or ≥120% | 0.83 | 0.67 | 1.00 |
| Cystine | ≥110% | 0.83 | 0.83 | 0.82 |
| Ornithine/Cystine | ≤88% | 0.91 | 0.83 | 1.00 |

Teratogenicity Threshold, A critical threshold of metabolic perturbation that is associated with teratogenesis;
Accuracy, number of correct predictions divided by the number test compounds evaluated;
Sensitivity, Detection of teratogens;
Specificity, Detection of non-teratogens.

Phase 2 Development and Evaluation of a Targeted Biomarker Assay to Predict Developmental Toxicity Associated with Exposure.

Targeted LC-HRMS Method Development. In the second phase of this study, a targeted biomarker-based assay was developed using the metabolites confirmed in Phase 1. Since toxicity is a function of both the chemical agent and exposure level, the high level of predictivity associated with a threshold of toxicity of the o/c ratio provided an opportunity for development of a targeted, rapid, teratogenicity assay. To that end, a short and reproducible analysis method was developed and optimized for fast-turnaround analysis of relative changes in ornithine and cystine abundance in hES cell spent media samples. In contrast, the untargeted metabolomic methods that had been previously used were designed to analyze a wider breadth of small molecules, and thus required a lengthy chromatographic separation. The prior platform also depended upon two data acquisitions for each sample, in positive and negative ionization modes. Focusing on the chromatographic separation, ionization and detection of ornithine and cystine only, a new, targeted method was designed specifically to more rapidly measure the relative changes of these metabolites observed in the hES cell model system. The new UPLC-HRMS method was developed and assessed using spent media samples (prepared as previously described) for added speed, sensitivity, and retention time reproducibility for measurements of ornithine and cystine. This resulted in a significant reduction in assay turn-around time. The data acquisition time for each sample was reduced from 23 to 6.5 minutes, providing a four-fold increase in LC-HRMS throughput. The positive ionization mode was preferentially amenable for detection of these metabolites, thereby eliminating the need for the negative mode, which further reduced the total analysis time by half for each sample batch, thus increasing total instrument throughput eight-fold. Method reproducibility was evaluated across 17 batches performed over 120 days using reference treatment samples (DMSO treated cells). The average CV for the integrated area of the internal standards and endogenous metabolites was <5% and <8%, respectively, demonstrating that the method performs in a reproducible manner.

Figure 5A:
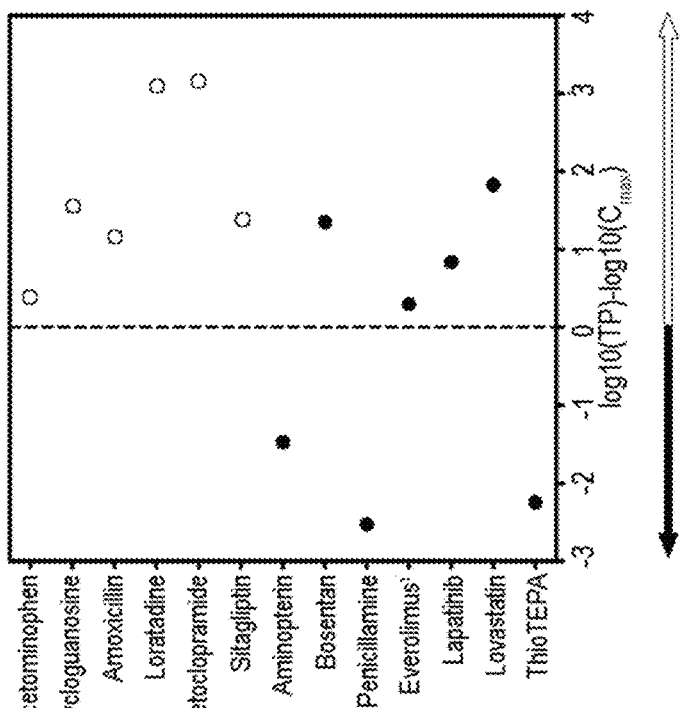
FIGS. 5A and 5B. Visualization of the difference between a compound's teratogenicity potential concentration for the o/c ratio (TP) determined in Phase 2 and $C_{max}$ values from the targeted biomarker assay for the training set (FIG. 5A) and test set (FIG. 5B). Filled points correspond to teratogens and open points correspond to non-teratogens. Treatments that have a difference between the TP and $C_{max}$ less than 0 are classified as teratogens and treatments with a difference between the TP and $C_{max}$ greater than 0 are classified as non-teratogens. The x-axis is the log base 10 transformed teratogen potential concentration value subtracted from the log base 10 transformed $C_{max}$ concentration value (see Tables 6 and 7). The y-axis is the treatment ordered by non-teratogens and teratogens. Open arrows indicate the range where a compound would be classified as a non-teratogen. Filled arrows indicate the range where a compound would be classified as a teratogen. [1]The $C_{max}$ for everolimus is below the lowest exposure level used in the assay, the o/c ratio for this compound begins below the teratogenicity threshold, so it is classified as a teratogen.

Identification of the Teratogenicity Threshold. Based on the high classification accuracy achieved in Phase 1 using a defined teratogenicity threshold, a 9-point concentration curve was used to classify developmental toxicity potential based on a range of exposures. The teratogenicity threshold was optimized using the Phase 2 training set data by selecting a threshold that produced the highest accuracy of prediction with the greatest sensitivity. The predicted teratogenicity potential concentration was compared to the therapeutic $C_{max}$ to score the performance and classification accuracy of this new assay design (described in FIG. 3, Table 6). With this approach, a 12% decrease in the o/c ratio relative to the reference treatment was the optimum threshold and was able to classify the training set of compounds with 96% accuracy (Table 7, FIG. 5A). The assay correctly classified all the non-teratogens (100% specificity) and misclassified only one of the known human development toxicants, diphenylhydantoin (92% sensitivity).

Figure 5B:
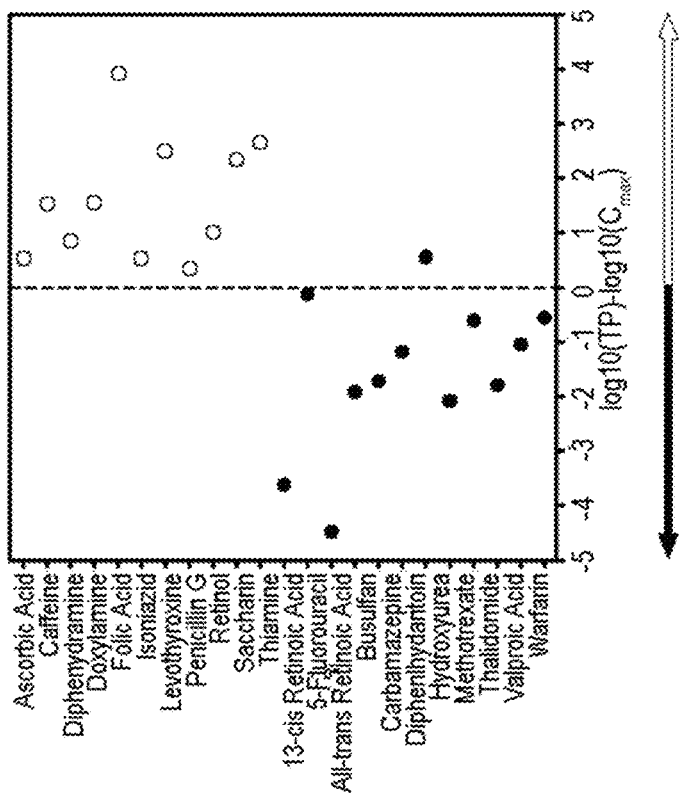
Figure 6A:
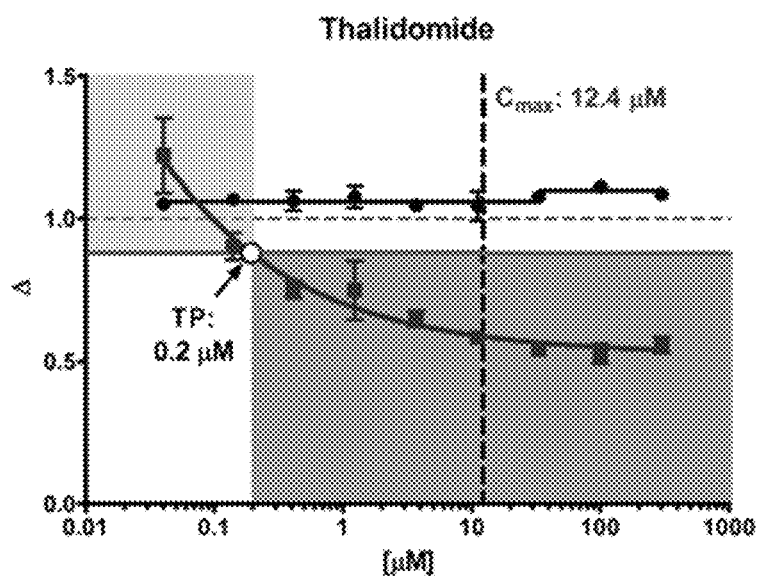
FIGS. 6A to 6F. Targeted biomarker assay results for a representative subset of the training set compounds (Table 6). The dose response curves for the viability analysis (black curve) and o/c ratio (grey curve) are shown for 4 known human teratogens: thalidomide (FIG. 6A), all-trans retinoic acid (FIG. 6B), valproic acid (FIG. 6C), 5-fluorouracil (FIG. 6D), and 2 non-teratogens: retinol (FIG. 6E) and saccharin (FIG. 6F). The x-axis is the concentration (µM) of the compound. Both the cell viability measurements and o/c ratio measurements exist on the same scale represented by Δ on the y-axis. The y-axis value of the o/c ratio is the ratio of the reference treatment normalized (fold change) values (ornithine/cystine). The y-axis value for the viability measurement is the treatment cell viability RFU normalized to the reference treatment cell viability RFU. The vertical broken black line indicates the compound specific $C_{max}$ and the horizontal grey line indicates the teratogenicity threshold (0.88). The open circle represents the teratogen potential concentration (TP) for the o/c ratio. The lighter and darker shaded areas represent the concentrations where the compound is predicted to be non-teratogenic or teratogenic, respectively. The points are mean values and error bars are the standard error of the mean. Interpretation of these figures is outlined in FIGS. 2 and 3.
Figure 6B:
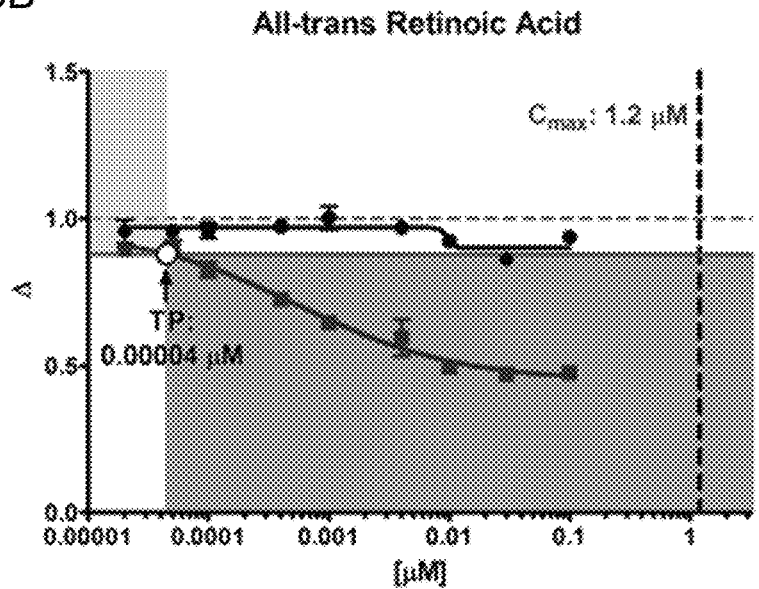
Figure 6C:
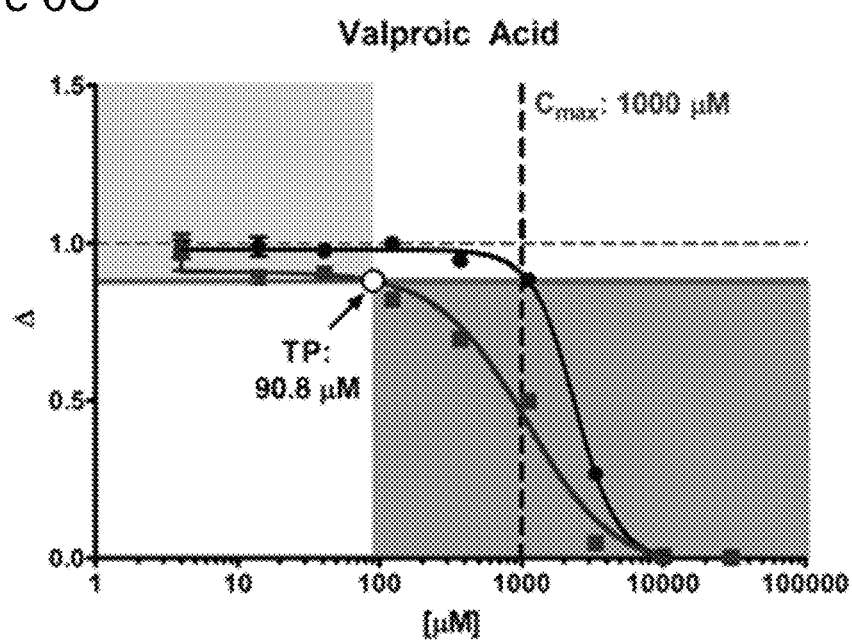
Figure 6D:
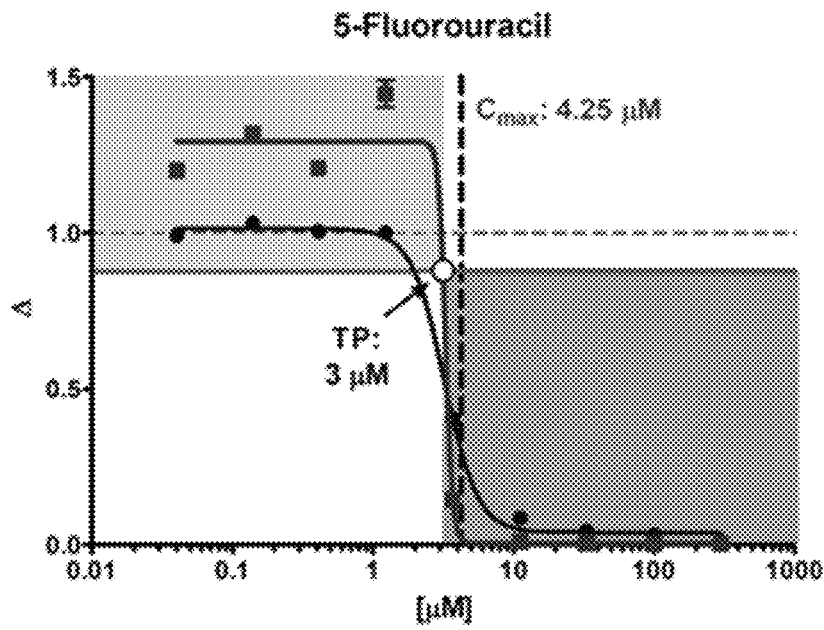
Figure 6E:
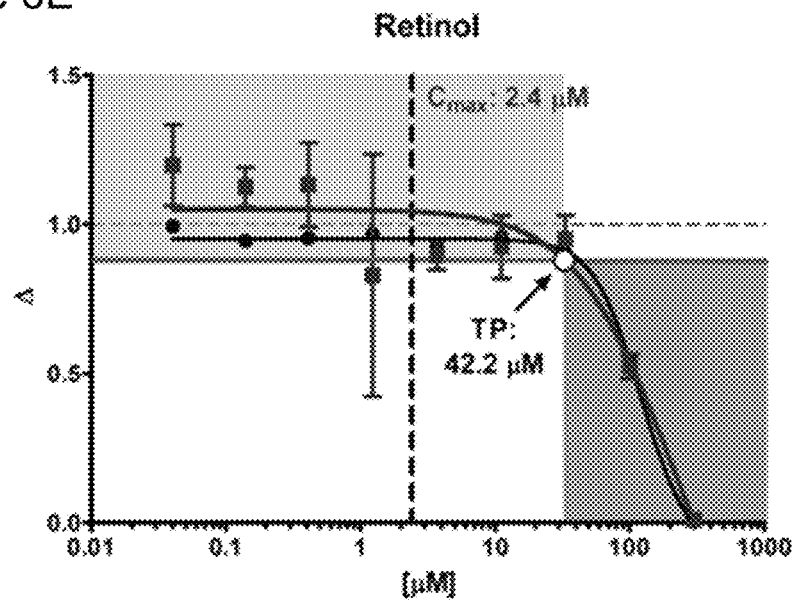
Figure 6F:
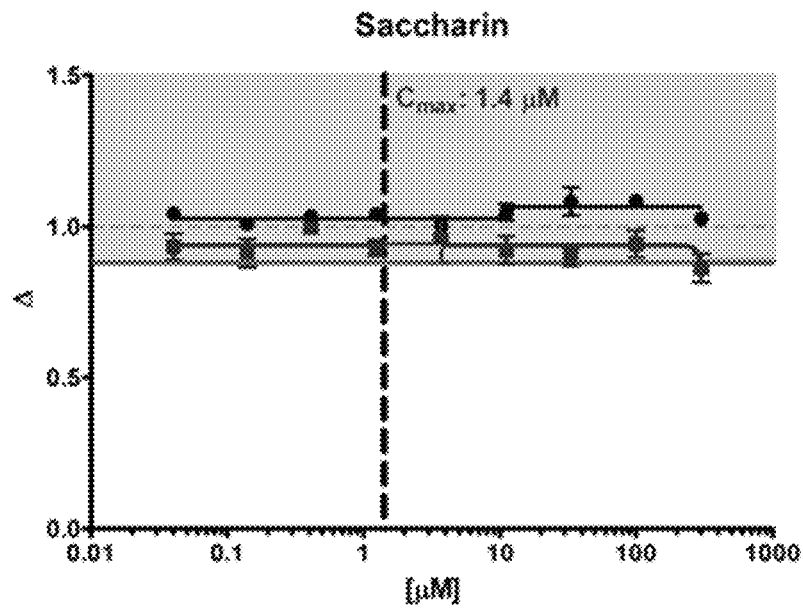

Evaluation of the Targeted Biomarker Assay Performance based on the Test Set Predictions. The teratogenicity threshold identified using the training set was applied to the test set of compounds to assess the predictivity of the targeted biomarker assay developed in this study. The test set consisted of 13 compounds not included in the training set with known human teratogenicity, having FDA pregnancy classifications of B, D and X. The teratogenicity potential concentration of each compound for the o/c ratio was scored against the compound's therapeutic $C_{max}$. The test set was classified with 77% accuracy (100% specificity, 57% sensitivity, Table 7). The o/c ratio incorrectly classified teratogens bosentan, lapatinib and lovastatin (Table 8, FIG. 5B). Please note that the $C_{max}$ for everolimus is below the lowest exposure level used in the assay and the o/c ratio for this compound begins below the teratogenicity threshold, so it is classified as a teratogen even though it groups with the non-teratogens in FIG. 5B.

TABLE 5

Targeted Biomarker Assay Results: Training Set.

| Compound | $C_{max}$ (μM) | Teratogenicity Potential (μM) O/C Ratio | Cell Viability | O/C Ratio Prediction | Viability Prediction | $C_{max}$ Ref. |
|---|---|---|---|---|---|---|
| Non-Teratogens | | | | | | |
| Ascorbic Acid | 90 | >300 | >300 | NON | NON | a |
| Caffeine | 9.3 | >300 | >300 | NON | NON | b |
| Diphenhydramine | 0.25 | 1.8 | 78.9 | NON | NON | c |
| Doxylamine | 0.38 | 12.9 | >300 | NON | NON | c |
| Folic Acid | 0.035 | >300 | >300 | NON | NON | d |
| Isoniazid | 51 | 165.4 | >300 | NON | NON | e |
| Levothyroxine | 0.14 | 43.5 | >300 | NON | NON | f |
| Penicillin G | 134.6 | >300 | >300 | NON | NON | g |
| Retinol | 2.4 | 42.2 | 42.8 | NON | NON | h |
| Saccharin | 1.4 | >300 | >300 | NON | NON | i |
| Thiamine | 0.67 | >300 | >300 | NON | NON | j |
| Teratogens | | | | | | |
| 13-cis Retinoic Acid | 2.9 | 0.0007 | >300 | TER | NON | k |
| 5-Fluorouracil | 4.25 | 3 | 2 | TER | TER | l |
| All-trans Retinoic Acid | 1.2 | 0.00004 | 114.5 | TER | NON | m |
| Busulfan | 49.6 | 0.6 | 3 | TER | TER | n |
| Carbamazepine | 47 | 0.9 | >300 | TER | NON | o |
| Cytosine Arabinoside | 0.6 | 0.04 | 0.1 | TER | TER | p |
| Diphenylhydantoin | 79.3 | 263.3 | 288.7 | NON | NON | q |
| Hydroxyurea | 565 | 5 | 251.6 | TER | TER | r |
| Methotrexate | 0.2 | 0.05 | 0.05 | TER | TER | s |

TABLE 5-continued

Targeted Biomarker Assay Results: Training Set.

| Compound | $C_{max}$ (μM) | Teratogenicity Potential (μM) O/C Ratio | Teratogenicity Potential (μM) Cell Viability | O/C Ratio Prediction | Viability Prediction | $C_{max}$ Ref. |
|---|---|---|---|---|---|---|
| Thalidomide | 12.4 | 0.2 | >300 | TER | NON | t |
| Valproic Acid | 1000 | 90.8 | 1113.7 | TER | NON | u |
| Warfarin | 23.4 | 6.5 | >300 | TER | NON | v |

$C_{max}$, therapeutic peak plasma in vivo concentration; Teratogenicity Potential, interpolated concentration when the dose response curve of the o/c ratio or cell viability crosses the teratogenicity threshold;
NON, potential non-teratogen;
TER, potential teratogen.
Teratogenicity potential values for the o/c ratio and viability measurements that occur at an exposure level below the $C_{max}$ value are bolded.
a Padayatty et al., 2004, *Ann Intern Med*; 140: 533-537.
b *Caffeine Pharmacology* (see worldwide web at reference.medscape.com/drug/cafcit-nodoz-caffeine-342995#10).
c Luna et al., 1989, *J Clin Pharmacol*; 29: 257-260.
d Ubeda et al., 2011, *Nutrition*; 27: 925-930.
e Isoniazid (systemic), (see the worldwide web at drugs.com/mmx/isoniazid.html).
f Briggs et al., 2011, "Drugs in pregnancy and lactation," 9th ed. Philadelphia: Lippincott Williams & Wilkins
g Penicillin G Potassium Injection (Product Information, 2012), Baxter Healthcare, Deerfield, Illinois.
h Aquasol A (Product Information), Mayne Pharma, Paramus, New Jersey.
i Vaisman et al., 2001, *Arzneimittelforschung*; 51: 246-252.
j Drewe et al., 2003, *J Clin Pharm Ther*; 28: 47-51.
k Accutane (Product Information, 2010), Roche Laboratories, Nutley, New Jersey.
l Oman et al., 2005, *Cancer Chemother Pharmacol*; 56: 603-609.
m Muindi et al., 1992, *Cancer Res*; 52: 2138-2142.
n Busulfex (Product Information, 2011), Otsuka America Pharmaceutical, Rockville, Maryland.
o Mahmood and Chamberlin, 1998, *Br J Clin Pharmacol*; 45: 241-246.
p Weinstein et al., 1982, *Blood*; 59: 1351-1353.
q Dilantin (Product Information, 2012), Pfizer, New York, New York.
r Liebelt et al., 2007, *Birth Defects Res B Dev Reprod Toxicol*; 80: 259-366.
s Shoda et al., 2007, *Mod Rheumatol*; 17: 311-316.
t Thalidomide Pharmacology (see the worldwide web at reference.medscape.com/drug/thalomid-thalidomide-343211#10).
u Depacon (Product Information, 2013), AbbVie, North Chicago, Illinois.
v Welle-Watne et al., 1980, *Medd Norsk Farm Selsk*; 42: 103-114.

TABLE 6

Model Metrics of the Ornithine/Cystine Ratio Compared to Cell Viability from the Targeted Biomarker Assay.

| Assay | Accuracy | Sensitivity | Specificity |
|---|---|---|---|
| Training Set | | | |
| O/C Ratio | 0.96 | 0.92 | 1.00 |
| Cell Viability | 0.70 | 0.42 | 1.00 |
| Test Set | | | |
| O/C Ratio | 0.77 | 0.57 | 1.00 |
| Cell Viability | 0.62 | 0.29 | 1.00 |

Accuracy, number of correct predictions divided by the number test compounds evaluated;
Sensitivity, Detection of teratogens;
Specificity, Detection of non-teratogens.

TABLE 7

Targeted Biomarker Assay Results: Test Set.

| Compound | $C_{max}$ (μM) | Teratogenicity Potential (μM) O/C Ratio | Teratogenicity Potential (μM) Cell Viability | O/C Ratio Prediction | Viability Prediction | $C_{max}$ Ref. |
|---|---|---|---|---|---|---|
| Non-Teratogens | | | | | | |
| Acetaminophen | 116.4 | >300 | >300 | NON | NON | a |
| Acycloguanosine | 3 | 95.8 | >300 | NON | NON | b |
| Amoxicillin | 20.5 | >300 | >300 | NON | NON | c |
| Loratadine | 0.03 | 37.8 | 76.3 | NON | NON | d |
| Metoclopramide | 0.15 | 190.8 | >300 | NON | NON | e |
| Sitagliptin | 0.95 | 22.6 | >300 | NON | NON | f |
| Teratogens | | | | | | |
| Aminopterin | 0.3 | 0.01 | 0.01 | TER | TER | g |
| Bosentan | 2 | 44.9 | 221.9 | NON | NON | h |
| D-Penicillamine | 13.4 | <0.04 | >300 | TER | NON | i |
| Everolimus | 0.02 | <0.04 | 5.2 | TER | NON | j |
| Lapatinib | 4.2 | 29 | 20.8 | NON | NON | k |

TABLE 7-continued

Targeted Biomarker Assay Results: Test Set.

| Compound | $C_{max}$ (μM) | Teratogenicity Potential (μM) O/C Ratio | Teratogenicity Potential (μM) Cell Viability | O/C Ratio Prediction | Viability Prediction | $C_{max}$ Ref. |
|---|---|---|---|---|---|---|
| Lovastatin | 0.02 | 1.3 | 4.1 | NON | NON | l |
| ThioTEPA | 7 | 0.04 | 0.5 | TER | TER | m |

$C_{max}$, therapeutic peak plasma in vivo concentration; Teratogenicity Potential, interpolated concentration when the dose response curve of the o/c ratio or cell viability crosses the teratogenicity threshold;
NON, potential non-teratogen;
TER, potential teratogen.
Teratogenicity potential values for the o/c ratio and viability measurements that occur at an exposure level below the $C_{max}$ value are bolded.
a Tylenol (Product Information, 2010), McNeil Consumer Healthcare, Fort Washington, Pennsylvania.
b Palma-Aguirre et al., 2007, Clin Ther; 29: 1146-1152.
c Amoxil (Product Information, 2011), Dr Reddy's Laboratories, Bridgewater, New Jersey.
d Hilbert et al., 1987, J Clin Pharmacol; 27: 694-698.
e Leucuta et al., 2004, Rom J Gastroenterol; 13: 211-214.
f Januvia (Product Information, 2013), Merck, Whitehouse Station, New Jersey.
g Cole et al., 2005, Clin Cancer Res; 11: 8089-8096.
h van Giersbergen et al., 2007, Clin Pharmacol Ther; 81: 414-419.
i Cuprimine (Product Information. 2004), Merck, Whitehouse Station, New Jersey.
j Everolimus (Product Information, 2011), Novartis Sverige A B, Täby, Sweden.
k Tykerb (Product Information, 2013), GlaxoSmithKline, Research Triangle Park, North Carolina.
l Altoprev (Product Information, 2012), Andrx Labs, Fort Lauderdale, Florida.
m Thiotepa (Product Information, 2001), Bedford Laboratories, Bedford, Ohio.

Comparison of the Ornithine/Cystine Ratio and Cell Viability. Because the metabolites that make up the o/c ratio are measured in spent cell culture media, the treated cells were available to perform cell viability analysis. The cell viability results were compared to the o/c ratio to determine if the change in the ratio was due to cell death or if it was due to metabolic changes unrelated to changes in cell viability. The viability results were evaluated to determine classification performance using an approach similar to the o/c ratio (FIG. 3). The teratogenicity threshold that was determined using the o/c ratio results from the training set was also used to classify teratogenicity by cell viability based on the interpolated concentration at which the cell viability dose response curve exceeds the teratogenicity threshold (Tables 6 and 8). This enabled a direct comparison of the o/c ratio and cell viability at equal levels of change from controls. Cell viability had an accuracy of 70% for the training set and 62% for the test set (Table 7). The cell viability assay was successful in correctly classifying all of the non-teratogens in both the training and test sets but performed poorly for the classification of teratogens, correctly classifying only 5 of the 12 compounds in the training set (42% sensitivity, Table 7) and 2 of the 7 teratogens in the test set (29% sensitivity, Table 7). Those that were correctly classified by cell viability are antineoplastic compounds that kill dividing cells.

When applied to the training and test sets, the o/c ratio was 26% and 15% more accurate, respectively, than viability alone for the prediction of development toxicity (Table 7). Both the o/c ratio and cell viability assay correctly classify non-teratogens with respect to the $C_{max}$ having 100% specificity, however they differ in their ability to discriminate teratogens (Table 7). The o/c ratio is 50% more sensitive in the detection of teratogens than viability alone in the training set and 28% more sensitive in the test set (Table 7). Additionally, the o/c ratio is able to classify both cytotoxic and non-cytotoxic teratogens correctly. The decrease in false negatives provided by the o/c ratio is related to the assay's measurement of metabolic perturbation that can occur independent of changes in cell viability.

Highlighted in FIG. 6 is a subset of the results that demonstrate several characteristics of the assay with respect to the o/c ratio performance relative to cell viability. Thalidomide (FIG. 6A) and all-trans retinoic acid (FIG. 6B) are examples of teratogens that exhibit a change in the o/c ratio indicative of developmental toxicity in the absence of cytotoxicity. The teratogen valproic acid (FIG. 6C) is an example of a cytotoxic teratogen that causes a marked change in the o/c ratio at exposure levels well before cytotoxicity is observed. 5-fluorouracil (FIG. 6D) is an antineoplastic teratogen that yields a change in o/c ratio that is directly correlated with a decrease in cell viability and the change in the metabolite ratio is likely a direct result of cell death. Retinol (FIG. 6E) is an example of a cytotoxic non-teratogen where the o/c ratio is directly correlated with cell death at exposure levels almost 20 times higher than those normally encountered by humans. The non-teratogen saccharin (FIG. 6F) is a compound that yields no change in the o/c ratio or viability at the exposures examined in this study.

Application of the O/C Ratio to Compounds with Unknown Human Teratogenicity. The targeted biomarker assay was applied to an application set of 10 compounds that have unknown human developmental toxicity outcomes. Since the human developmental toxicity of these compounds is unknown, the $C_{max}$ approach (illustrated in FIG. 3) to score assay performance was not applied and the compounds were treated as unknowns, as is illustrated in FIG. 2. The results are presented as they would be generated by the assay utilized in an industrial setting. The teratogenicity potential concentrations for the o/c ratio and cell viability are summarized in Table 9. All 10 compounds exhibited a change in the o/c ratio indicative of teratogenicity, although concentration at which this change occurred varied greatly between compounds. Nine of the 10 compounds exhibited a change in cell viability within the exposure range tested (Table 9). Seven of the 10 compounds caused a change in the o/c ratio prior to or in the absence of cytotoxicity (bolded compounds, Table 9). Rodent developmental toxicity testing identified a teratogenic and/or embryotoxic effect in seven of the 10 compounds in the absence of maternal toxicity. The other three compounds (adefovir dipivoxil, cidofovir, and ramelteon) were only embryotoxic at exposure levels that also caused maternal toxicity so it is unknown if the effect was due to compound exposure.

TABLE 8

Targeted Biomarker Assay Results: Application Set.

| Compound | $C_{max}$ (µM) | Teratogenicity Potential (µM) | | Rodent in vivo test results[a] | | $C_{max}$ Ref. |
|---|---|---|---|---|---|---|
| | | O/C Ratio | Cell Viability | Teratogenic[b] | Embryotoxic[c] | |
| 6-Aminonicotinamide | NA | <0.04 | 24.5 | +[d] | −[d] | NA |
| Abacavir | 14.9 | 95.1 | 94.1 | + | + | i |
| Adefovir dipivoxil[e] | 0.03 | 0.0015 | 0.02 | − | − | j |
| Amprenavir | 15.1 | 236.9 | 259.5 | + | + | k |
| Artesunate | 73.9 | 0.64 | 0.58 | +[f] | +[f] | l |
| Cidofovir[g] | 41.2 | 0.3 | 1.9 | − | − | m |
| Entacapone | 3.9 | 6.7 | 127 | + | − | n |
| Fluoxetine | 0.04 | 25.1 | 23 | − | + | o |
| Ramelteon[h] | 0.02 | 34 | >300 | − | − | p |
| Rosiglitazone | 1.7 | 18.9 | 21.8 | − | + | q |

$C_{max}$, peak plasma concentration in humans; Teratogenicity Potential, interpolated concentration when the dose response curve of the o/c ratio or cell viability crosses the teratogenicity threshold;
NA, not available or undetermined.
Teratogenicity potential values for the o/c ratio that occur before cell viability are bolded.
[a]Data was compiled from Briggs et al. (2011, "Drugs in pregnancy and lactation," 9th ed. Philadelphia: Lippincott Williams & Wilkins) unless otherwise noted.
[b]A test compound was considered teratogenic if it caused structural malformations in the absence of maternal toxicity.
[c]This column refers to an embryotoxic effect in the absence of teratogenic effects. A test compound was considered embryotoxic if it caused growth retardation or embryo lethality in the absence of maternal toxicity.
[d]Shepard and Lemire, 2007, "Catalog of teratogenic agents," 12th ed. Baltimore: The Johns Hopkins University Press.
[e]Adefovir dipivoxil was teratogenic and embryotoxic at maternally toxic doses.
[f]Clark, 2009, *Reprod Toxicol*; 28: 285-296; and Shepard and Lemire, 2007, "Catalog of teratogenic agents," 12th ed. Baltimore: The Johns Hopkins University Press.
[g]Cidofovir was embryotoxic at maternally toxic doses.
[h]Ramelteon was teratogenic at maternally toxic doses.
i Ziagen (Product Information, 2012), GlaxoSmithKline, Research Triangle Park, North Carolina.
j Hepsera (Product Information, 2012), Gilead Sciences, Foster City, California.
k Agenerase (Product Information, 2005), GlaxoSmithKline, Research Triangle Park, North Carolina.
l Miller et al., 2012, *Malar J*; 11: 255.
m Vistide (Product Information 2000), Gilead Sciences, Foster City, California.
n Comtan (Product Information, 2010), Novartis Pharmaceuticals, East Hanover, New Jersey.
o Sarafem (Product Information, 2013), Warner Chilcott, Rockaway, New Jersey.
p Karim et al., 2006, *J Clin Pharmacol*; 46: 140-148.
q Avandia (Product Information, 2011), GlaxoSmithKline, Research Triangle Park, North Carolina.

Assay Performance (Comparison to Other Assays). The developmental toxicity predictions based on the o/c ratio for the training and test sets were compared to published results from other model systems (Table 10). The developmental toxicity predictions from the model systems presented in Table 10 for the application set are summarized in Supplementary Table 1. For the combined 36 training and test set compounds, comparisons were made on a model system-by-system basis using only the treatments evaluated in both the targeted biomarker assay and each model system it was being compared to. The results of the comparisons (Table 11) indicate that the o/c ratio described here is a more accurate predictor of human developmental toxicants than the other model systems considered. The increase in accuracy is due to a lower false positive rate (increased specificity) of the o/c ratio in each comparison with significant increase in specificity over other in vitro systems such as mEST and WEC, as well as a moderate gain in sensitivity. Interestingly, the o/c ratio is able to correctly classify the non-teratogens caffeine and retinol and teratogens warfarin and D-penicillamine, where the majority of other model systems fail. There is a high degree of concordance (>75%) between the teratogenicity prediction of the o/c ratio and the in vivo rodent and rabbit models as well as the ZET (Table 11). Concordance is lower between the o/c ratio and the mEST and WEC (67% and 69%, respectively, Table 11). The reason for lower concordance between the o/c ratio and these in vitro models is due to the high accuracy of the targeted biomarker assay.

TABLE 9

Comparison of Targeted Biomarker Assay Results to Published Developmental Toxicity Assay Results: Training and Test Set.

| Compound | Humans[a] | Targeted Biomarker Assay | Rodent[a] | Rabbit[a] | mEST | ZET | WEC |
|---|---|---|---|---|---|---|---|
| Acetaminophen | NON | NON | NON | NA | NA | NON[e] | TER[k] |
| Acycloguanosine | NON | NON | TER | NON | NA | NA | TER[l] |
| Amoxicillin | NON | NON | NON | NA | NA | NA | NA |
| Ascorbic Acid | NON | NON | NON | NA | NON[b] | NON[c,d,e] | NON[f] |
| Caffeine | NON | NON | TER | TER | TER[b] | TER[e] | TER[o] |
| Diphenhydramine | NON | NON | NON | NON | TER[b] | TER[e] | NON[f] |

TABLE 9-continued

Comparison of Targeted Biomarker Assay Results to Published Developmental Toxicity Assay Results: Training and Test Set.

| Compound | Humans[a] | Targeted Biomarker Assay | Rodent[a] | Rabbit[a] | mEST | ZET | WEC |
|---|---|---|---|---|---|---|---|
| Doxylamine | NON | NON | NON | NON | TER[m] | NA | NON[f] |
| Folic Acid | NON | NON | NON[g] | NA | NA | NA | NON[h] |
| Isoniazid | NON | NON | NON | NON | NON[b,i] | NON[c,n] | TER[f,j] |
| Levothyroxine | NON | NON | NON | NON | NA | NA | NA |
| Loratadine | NON | NON | NON | NON | NON[i] | TER[d] | NON[f,j] |
| Metoclopramide | NON | NON | NON | NON | TER[i,m] | NON[d] | NON[f,j] |
| Penicillin G | NON | NON | NON | NON | NON[b,i] | NON[c,e,n] | NON[f,j] |
| Retinol | NON | NON | TER | TER | NON[p] | TER[c,n] | TER[q] |
| Saccharin | NON | NON | NON | NON | NON[b,i] | NON[c,e] | NON[j] |
| Sitagliptin | NON | NON | TER | NON | NA | NA | NA |
| Thiamine | NON | NON | NA | NA | NA | NA | NA |
| 13-cis Retinoic | TER | TER | TER | TER | TER[p] | TER[r] | TER[s] |
| 5-Fluorouracil | TER | TER | TER | TER | TER[b,i] | TER[c] | TER[f,k] |
| All-trans Retinoic | TER | TER | TER | TER | TER[b,p] | TER[c,e,r] | TER[q,s] |
| Aminopterin | TER | TER | TER | TER | NA | NA | NA |
| Bosentan | TER | NON | TER | NON | NA | NA | NA |
| Busulfan | TER | TER | TER | TER | TER[i] | NA | TER[j] |
| Carbamazepine | TER | TER | TER | NA | TER[i] | TER[t] | TER[j] |
| Cytosine | TER | TER | TER | NA | TER[i] | TER[n] | TER[j] |
| Diphenylhydantoi | TER | NON | TER | TER | TER[b,i] | NON[a] | TER[f,j] |
| D-Penicillamine | TER | TER | TER | NA | NON[m] | NON[d] | NON[f] |
| Everolimus | TER | TER | TER | NON | NA | NA | NA |
| Hydroxyurea | TER | TER | TER | TER | TER[b,i] | TER[c] | TER[f,j] |
| Lapatinib | TER | NON | TER | TER | NA | NA | NA |
| Lovastatin | TER | NON | TER | NON | TER[m] | TER[d] | NA |
| Methotrexate | TER | TER | TER | TER | TER[b,i] | TER[d] | TER[f] |
| Thalidomide | TER | TER | NON[a] | TER | NA | TER[d] | TER[f] |
| ThioTEPA | TER | TER | TER | TER | NA | TER[v] | NA |
| Valproic Acid | TER | TER | TER | TER[u] | TER[b,i] | TER[e,n] | TER[f,j] |
| Warfarin | TER | TER | TER | NON | NON[i,m] | TER[d] | NON[j] | mEST, mouse embryonic stem cell test;

ZET, zebrafish embryotoxicity test;

WEC, whole embryo culture;

NON, non-teratogen;

TER, teratogen;

NA, not available.

If there were conflicting predictions, the classification from the more recent publication or with more publications in agreement was used. Bolded results indicate predictions that differ from known human developmental toxicity effects.

[a]Human, rodent and rabbit effects summarized from Drugs in Pregnancy and Lactation (Briggs et al., 2011, "Drugs in pregnancy and lactation," 9th ed. Philadelphia: Lippincott Williams & Wilkins); TERIS and/or the ACToR database (on the World Wide Web at actor.epa.gov/actor/faces/ACToRHome.jsp) unless otherwise noted.

[b]Genschow et al., 2004, Altern Lab Anim; 32: 209-244.

[c]Brannen et al., 2010, Birth Defects Res B Dev Reprod Toxicol; 89: 66-77.

[d]Gustafson et al., 2012, Reprod Toxicol; 33: 155-164.

[e]Selderslaghs et al., 2012, Reprod Toxicol; 33: 142-154.

[f]Zhang et al., 2012, Toxicol Sci; 127: 535-546.

[g]Hansen et al., 1993, Teratology; 47: 420.

[h]Hansen, 1995, Teratology; 51: 12A.

[i]Paquette et al., 2008, Birth Defects Res B Dev Reprod Toxicol; 83: 104-111.

[j]Thomson et al., 2011, Birth Defects Res B Dev Reprod Toxicol; 92: 111-121.

[k]Stark et al., 1990, J Pharmacol Exp Ther; 255: 74-82.

[l]Klug et al., 1985, Arch Toxicol; 58: 89-96.

[m]Marx-Stoelting et al., 2009, Altern Lab Anim; 37: 313-328.

[n]McGrath and Li, 2008, Drug Discov Today; 13: 394-401.

[o]Robinson et al., 2010, Toxicol Sci; 118: 675-685.

[p]Louisse et al., 2011, Toxicol Lett; 203: 1-8.

[q]Ritchie et al., 2003, Birth Defects Res A Clin Mol Teratol; 67: 444-451.

[r]Herrmann, 1995, Toxicol In Vitro; 9: 267-283.

[s]King et al., 1989, Arch Toxicol; 63: 185-192.

[t]Madureira et al., 2011, Environ Toxicol Pharmacol; 32: 212-217.

[u]Jelovsek et al., 1989, Obset Gynecol; 74: 624-636.

[v]Weigt et al., 2011, Toxicology; 281: 25-36.

TABLE 10

Model Metrics of the Targeted Biomarker Assay Predictions Compared to Other Model Predictions Based on Treatments in Common.

| Model System | N | Concordance | Acc | TB_Acc | Sen | TB_Sen | Spec | TB_Spec |
|---|---|---|---|---|---|---|---|---|
| Targeted Biomarker Assay | 36 | NA | 0.89 | NA | 0.79 | NA | 1.00 | NA |
| Rodent | 35 | 0.74 | 0.86 | 0.89 | 0.95 | 0.79 | 0.75 | 1.00 |
| Rabbit | 28 | 0.79 | 0.79 | 0.86 | 0.75 | 0.75 | 0.83 | 1.00 |
| mEST | 23 | 0.65 | 0.74 | 0.91 | 0.85 | 0.85 | 0.60 | 1.00 |
| ZET | 24 | 0.75 | 0.75 | 0.92 | 0.86 | 0.86 | 0.60 | 1.00 |
| WEC | 26 | 0.69 | 0.73 | 0.96 | 0.85 | 0.92 | 0.62 | 1.00 |

N, The number of treatments assayed that were common between the model system and the targeted biomarker assay;
TB, the targeted biomarker assay results using the treatments evaluated in that model system;
Acc, Accuracy of model system;
TB_Acc, Accuracy of targeted biomarker assay;
Sen, Sensitivity of model system;
TB_Sen, Sensitivity of targeted biomarker assay;
Spec, Specificity of the model system;
TB_Sen, Specificity of the targeted biomarker assay.

TABLE 11

Comparison of Targeted Biomarker Assay Results to Published Developmental Toxicity Assay Results: Application Set.

| Compound | Humans[a] | Targeted Biomarker Assay[b] | Rodent[a] | Rabbit[a] | mEST | ZET | WEC |
|---|---|---|---|---|---|---|---|
| 6-Aminonicotinamide | NA | TER | TER | TER | TER[c] | NA | TER[d] |
| Abacavir | NA | NON | TER | NON | NA | NA | NA |
| Adefovir dipivoxil | NA | TER | NON | NON | NA | NA | NA |
| Amprenavir | NA | NON | TER | TER | NA | NA | NA |
| Artesunate | NA | TER | TER | TER | NA | NA | NA |
| Cidofovir | NA | TER | NON | NON | NA | NA | NA |
| Entacapone | NA | TER | TER | NON | NA | NA | NA |
| Fluoxetine | NA | NON | TER | NON | TER[e] | NA | NON[f,g] |
| Ramelteon | NA | NON | NON | NON | NA | NA | NA |
| Rosiglitazone | NA | NON | TER | TER | NA | NA | NON[h] | mEST, mouse embryonic stem cell test;
ZET, zebrafish embryotoxicity test;
WEC, whole embryo culture;
NON, non-teratogen;
TER, teratogen;
NA, not available.
If there were conflicting calls, the classification from the more recent publication or with more publications in agreement was used.
[a]Human, rodent and rabbit effects summarized from Drugs in Pregnancy and Lactation (Briggs et al., 2011, "Drugs in pregnancy and lactation," 9th ed. Philadelphia: Lippincott Williams & Wilkins), TERIS and/or the ACToR database (on the World Wide Web at actor.epa.gov/actor/faces/ACToRHome.jsp) unless otherwise noted.
[b]Predictions for the targeted biomarker assay were made using the therapeutic $C_{max}$ when available as described in the methods section and illustrated in FIG. 3. However, in application of the assay this method will not be used as a $C_{max}$ will not be available.
[c]Genschow et al., 2004, Altern Lab Anim; 32: 209-244.
[d]Piersma et al., 1995, Reprod Toxicol; 9: 275-280.
[e]Paquette et al, 2008, Birth Defects Res B Dev Reprod Toxicol; 83: 104-111.
[f]Thomson et al., 2011, Birth Defects Res B Dev Reprod Toxicol; 92: 111-121.
[g]Zhang et al., 2012, Toxicol Sci; 127: 535-546.
[h]Chan and Lau, 2006, Fertil Steril; 86: 490-492.

Discussion

The present assay has been developed to address the need for more accurate, rapid, and less expensive alternatives to animal testing. Our goal was to provide toxicologists with a new and biologically germane tool to aid in compound prioritization prior to the currently required in vivo testing and as part of emerging multi-tiered testing strategies. Undifferentiated hES cells represent a simple and elegant test system for modeling a test compound's developmentally toxic effects on human cells at the very earliest stages of development, which in some cases can lead to implications of the compound's effects in later stage fetal development as well. A developmental toxicity test based on hES cells reduces the risk of false-negatives due specifically to interspecies differences in developmental pathways and pharmacokinetics (Scott et al., 2013, Toxicol Lett; 219:49-58). The present example modifies an untargeted metabolomics-based developmental toxicity assay to decrease complexity and increase throughput by focusing on two biologically relevant metabolites that can accurately model human toxic response over a wide range of exposure levels.

This example demonstrates that a certain degree of metabolic perturbation can be used to predict a test compound's potential to cause developmental toxicity. The assay of this example uses a multi-exposure approach that allows for a look at cellular response over a large range of exposure levels. Application of the teratogenicity threshold to this approach allowed the use of changes in metabolism at increasing exposure levels to identify the concentration at which metabolism was altered in a manner indicative of potential teratogenicity. The model created here allows the comparison of changes in a metabolic ratio of ornithine and cystine to cell viability to identify the exposure level where changes in metabolism are likely to lead to teratogenicity and relate it to cell death. The combined evaluation of cell viability and changes in metabolism allow this assay to also identify when exposure could lead to developmental toxicity due to cell death or possible embryo toxicity. The o/c ratio can discriminate between teratogens and non-teratogens with a combined 89% accuracy in the training and test sets using the teratogenicity threshold set in Phase 2 (Table 11).

Analysis of metabolites is a critical process in understanding mechanisms of toxicity since metabolites play critical roles in the maintenance of homeostasis and signaling. Perturbation of individual metabolites has the ability to disrupt normal developmental processes. Alterations in metabolite abundance can occur via mechanisms independent of protein and transcript abundance such as allosteric interaction of a compound or compound's metabolite with an enzyme, defects in post-translational modification, disrupted protein-protein interactions and/or altered transport. Changes in metabolism, as measured in the spent medium of cell culture systems, yield a distinguishable "metabolic footprint," which is a functional measure of cellular metabolism that can be used to evaluate response to treatment. The perturbation of biochemical pathways that contain ornithine and cystine as reactants or products have been experimentally associated with mechanisms of teratogenesis. Extracellularly, or within the secretome measured by our assays, cystine predominates over cysteine due to the oxidative state of the medium. Cystine is rapidly converted to cysteine once it is imported into the intracellular environment and is part of the cystine/cysteine thiol redox couple, a critical component of a cell's regulatory capacity to handle reactive oxygen species (ROS). Its role has been investigated with regard to its capacity to modulate differentiation, proliferation, apoptosis, and other cellular events that may lead to teratogenesis (Hansen, 2006, *Birth Defects Res C Embryo Today;* 78:293-307). A broad spectrum of teratogens including pharmaceuticals, pesticides, and environmental contaminants are suspected of creating ROS or disrupting cellular mechanisms that maintain the appropriate balance of a cell's redox state, which can lead to adverse effects on developmental regulatory networks as a mechanism of action of developmental toxicity (Hansen, 2006, *Birth Defects Res C Embryo Today;* 78:293-307; Kovacic and Somanathan, 2006, *Birth Defects Res C Embryo Today;* 78:308-325). It has been hypothesized that a major mechanism of thalidomide teratogenesis and its species specific manifestation of developmental toxicity is related to ROS related up-regulation of apoptotic pathways during limb formation (Hansen, 2006, *Birth Defects Res C Embryo Today;* 78:293-307). The measurement of cystine in this assay provides insight into a cell's redox status. When cystine's uptake is perturbed, it can act as a biomarker, indicating a disruption in the cell's ability to signal using ROS related pathways.

The second metabolite in this assay is ornithine, which is secreted by the hES cells during culture. Ornithine is formed as a product of the catabolism of arginine into urea, is critical to the excretion of nitrogen, and is a precursor to polyamines. Catabolism of ornithine is impacted by the teratogen all-trans retinoic acid, which is a suppressor of the transcription of ornithine decarboxylase (ODC), leading to increased ornithine secretion which in turn inhibits polyamine synthesis (Mao et al., 1993, *Biochem* 295:641-644). It is also clear that ODC plays an important role in development, since a mouse model with ODC knocked out leads to disruption of very early embryonic stages and is lethal to the developing embryo (Pegg, 2009, *IUBMB Life;* 61:880-894). Alterations in ornithine levels could lead to the disruption in polyamine metabolism, which is critical for cellular growth and differentiation during human development (Kalhan and Bier, 2008, *Annu Rev Nutr;* 28:389-410).

Only one of the 23 compounds in the training set (diphenylhydantoin) and three of the 13 compounds in the test set (bosentan, lapatinib, and lovastatin) were misclassified in the targeted biomarker assay (Tables 6 and 8). All four of these compounds exhibited a change in the o/c ratio indicative of teratogenicity; however the teratogenicity potential concentration is higher than the therapeutic $C_{max}$, which was set as a marker of biological relevance for exposure level. For discovery compounds that will not have an established $C_{max}$ value, these changes in the o/c ratio can be used as a signal regarding the teratogenic potential of the compound. While epidemiological studies have shown an association between diphenylhydantoin and birth defects, there have been no such studies describing the incidence of birth defects following bosentan, lapatinib and lovastatin exposure during pregnancy. No case reports have been published regarding birth defects in infants exposed to bosentan or lapatinib during pregnancy and only a handful of reports describing malformations following lovastatin exposure during early pregnancy (TERIS).

Figure 7B:
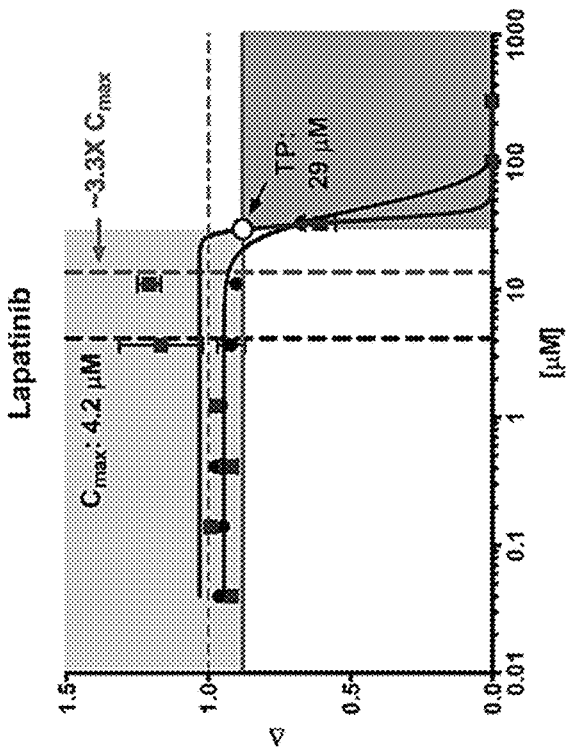
FIGS. 7A and 7B. Targeted biomarker assay results compared to rat in vivo developmental toxicity outcomes for two test set compounds (Table 7): lovastatin (FIG. 7A) and lapatinib (FIG. 7B). The dose response curves from the targeted biomarker assay for the viability analysis (black line) and o/c ratio (grey line) are shown. The x-axis is the concentration (µM) of the compound. Both the cell viability measurements and o/c ratio measurements exist on the same scale represented by Δ on the y-axis. The y-axis value of the o/c ratio is the ratio of the reference treatment normalized (fold change) values (ornithine/cystine). The y-axis value for the viability measurement is the treatment cell viability RFU normalized to the reference treatment cell viability RFU. The vertical broken black line indicates the compound specific $C_{max}$ and the horizontal grey line indicates the teratogenicity threshold (0.88). The open circle represents the teratogen potential concentration (TP) for the o/c ratio. The lighter and darker shaded areas represent the concentrations where the compound is predicted to be non-teratogenic or teratogenic, respectively. The broken grey line represents the concentration where a positive result was observed in the rat in vivo developmental toxicity test. The points are mean values and error bars are the standard error of the mean. Interpretation of these figures is outlined in FIGS. 2 and 3.
Figure 7A:
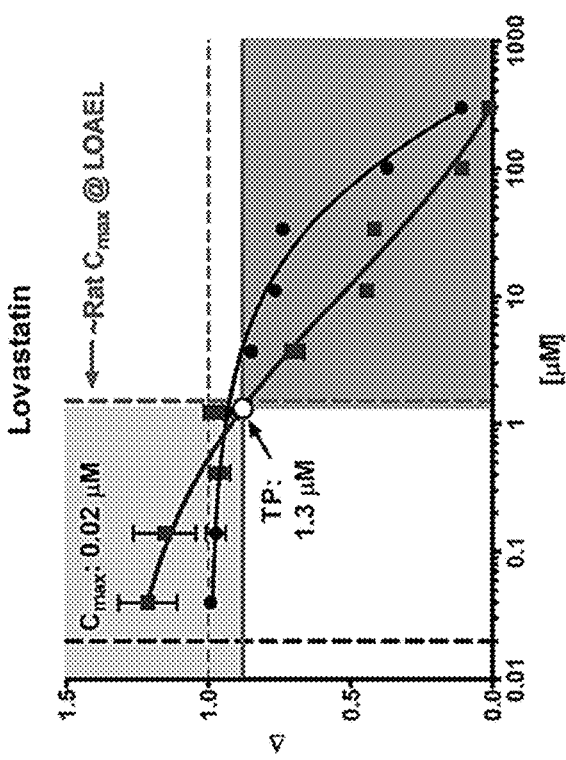

In vivo rat developmental toxicity studies have identified a lowest observed adverse effect level (LOAEL) for lovastatin of 100 mg/kg body weight per day during organogenesis (Lankas et al., 2004, *Birth Defects Res B Dev Reprod Toxicol;* 71:111-123). Interestingly, this level of exposure results in a $C_{max}$ around 1.5 µM (Lankas et al., 2004, *Birth Defects Res B Dev Reprod Toxicol;* 71:111-123), which is close to the teratogenicity potential identified by the o/c ratio in this study (1.3 µM, Table 7, FIG. 7A). Lapatinib causes rat pup mortality in vivo when given during organogenesis at exposure levels that are about 3.3 times the human clinical exposure based on AUC (Briggs G G, Freeman R K, Yaffe S J, 2011, "Drugs in pregnancy and lactation," 9th ed. Philadelphia: Lippincott Williams & Wilkins). This level of exposure is approximately equal to the concentration where cell viability decreases in hES cells following lapatinib exposure (FIG. 7B). Animal models are currently used to measure teratogenicity risk but it is still unknown how well their results correlate to human risk for individual compounds. While the primary goal of the assay is to predict potential for teratogenicity in humans, it is also important to understand concordance with in vivo animal models used for regulatory acceptance. These are a few examples of how the data generated in the targeted biomarker assay can be correlated to in vivo developmental toxicity data.

Figure 8:
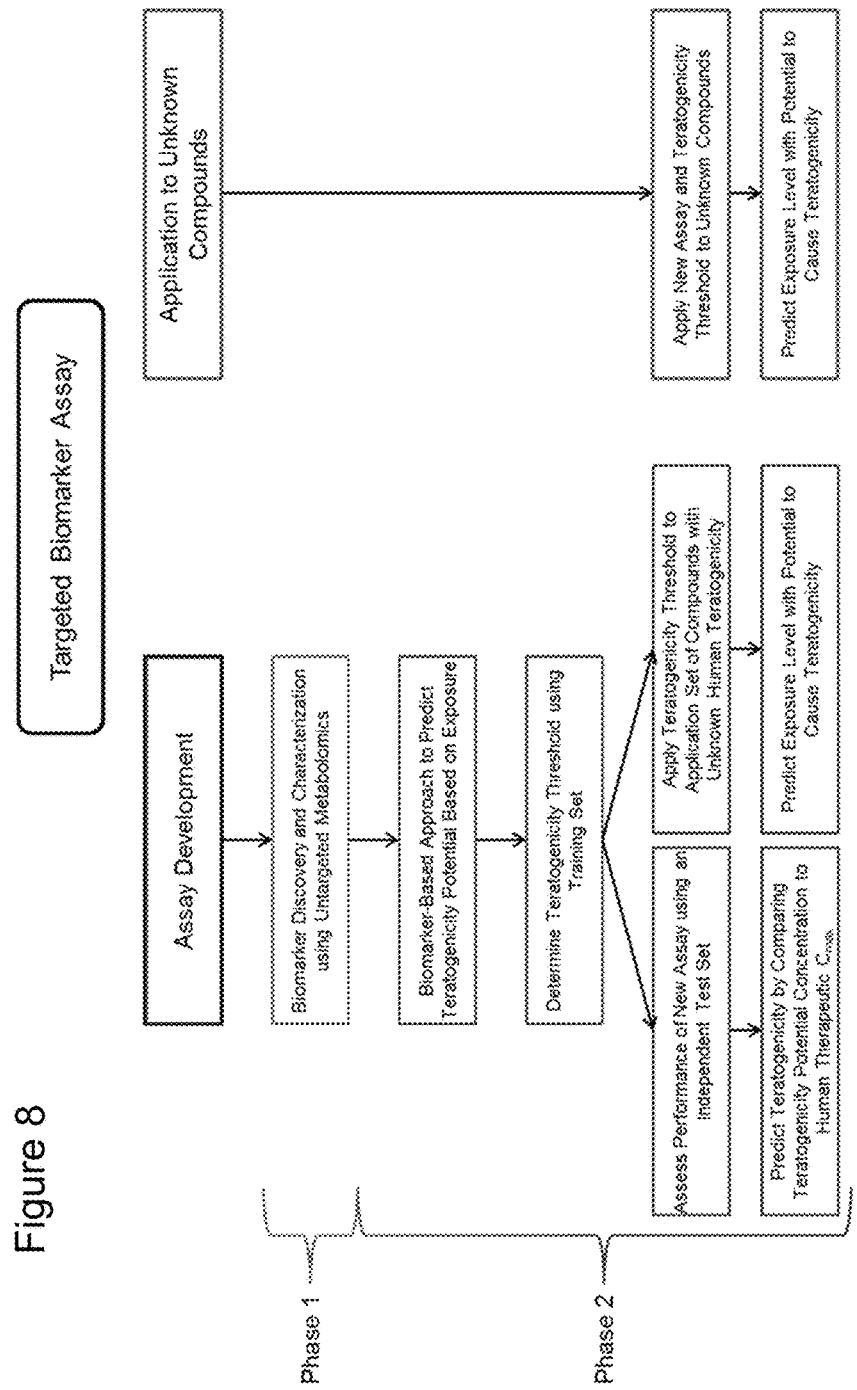
FIG. 8. Diagram outlining the development of the targeted biomarker assay compared to use with unknown compounds.

For the compounds evaluated in this study, the targeted biomarker assay agrees with in vivo rodent and rabbit studies about 75% of the time (Table 11). There is still significant opportunity to improve the understanding of how to translate compound concentrations from in vitro systems to human exposure levels (Bhattacharya et al., 2011, *PLoS One;* 6:e20887). The application set was used to demonstrate how the measurement of toxicity potential across an exposure range can put model response into perspective in terms of the overall compound risk when combined with additional assays conducted during a compound's discovery and development. The 10 compounds in this set have unknown human developmental toxicity outcomes, as would any novel compound. The o/c ratio was compared with the available $C_{max}$ for the application set of compounds to begin to assess the relevance of the signal of teratogenicity potential for each compound (Supplementary Table 1). The therapeutic $C_{max}$ was used to understand the potential exposure level encountered in humans. However, since the human teratogenicity of these compounds is unknown, the $C_{max}$ was not used to assess the predictivity of the assay. The application set was meant to demonstrate utility of the targeted biomarker assay for unknown compounds in contrast to assessment of assay performance for compounds with known human teratogenicity (FIG. 8). Any available preclinical in vivo findings were then used to develop and understanding of each compound and its risk potential. Such an approach could be used in adoption of the assay as part of a traditional compound discovery or preclinical development program, or as part of a new paradigm utilizing a panel of human cell based assays aimed at early decision making.

A significant advantage of the targeted biomarker assay is the use of human cells, derived from an embryo, which are able to recapitulate every cell type in the body and have an unlimited capacity to proliferate in culture. The possibility of species-specific differences in developmental toxicity that may be observed in other in vitro developmental toxicity assays is eliminated. In contrast to the ECVAM-evaluated mEST, the assay presented here does not require differentiation of the hES cells into specific lineages such as embryo bodies or cardiomyocytes. Differentiation into specific lineages may limit an assay's potential for predicting teratogens that affect a different developmental lineage. The assay described herein can correctly classify compounds that are known to affect multiple lineages, including cardiovascular, neural and skeletal (Tables 2 and 3). The targeted biomarker assay provides endpoints which are determined analytically and do not need any subjective interpretation of morphology, as is required by the mEST, post-implantation rat WEC test and ZET. Recent modifications to the mEST have begun to address these limitations by adding additional developmental endpoints (i.e., neural and osteoblast differentiation) and implementing molecular endpoints in place of subjective evaluation (reviewed in Theunissen and Piersma, 2012, *Front Biosci;* 17:1965-1975). Table 10 presents a comparison of the results of the targeted biomarker assay described here and five other developmental toxicity assays; the targeted biomarker assay has a higher accuracy than the other assays (Table 11). The higher accuracy of the predictions made with the o/c ratio is due to an increase in specificity, or the detection of non-teratogens, over the other assays. It is important to note that differences exist between each of the model systems in the way that compounds are predicted. None of the other assays included in Table 10 classify compounds based on human exposure levels, whereas our classification system directly compares a compound's teratogenicity potential to the known therapeutic $C_{max}$ for compounds that have known human developmental toxicity outcomes. When making predictions, the actual exposure levels of a compound likely to be encountered by a fetus are critical. Nine of the 17 human non-teratogens tested in the targeted biomarker assay caused a change in the o/c ratio at exposure levels above the therapeutic $C_{max}$. It is believed that any compound, given at the right dose, at the right time during development, in the right species will be teratogenic (Daston G P and Knudsen T B, 2010, "Fundamental concepts, current regulatory design and interpretation," In: Knudsen T B, Daston G P, editors. *Comprehensive Toxicology.* Vol 12, 2nd ed. New York: Elsevier. p 3-9). The ability of the targeted biomarker assay to separate exposure levels that are not indicative of teratogenicity from levels that are indicative of teratogenicity is a key strength of the assay.

Although the targeted biomarker assay described herein shows significant promise in predicting developmental toxicity, hES cells, as with other in vitro models, cannot fully reproduce all events contributing to the disruption of normal human development by exogenous chemicals. In vitro models of toxicity do not include the effects of absorption, distribution, metabolism and excretion (ADME), which may make it difficult to predict how a substance of unknown toxicity will act in vivo. The absence of metabolic activity could partially be overcome by the addition of an exogenous bioactivation system when metabolic activation is required or to test both the parent compound and any known metabolites for developmental toxicity potential. Testing both parent compounds and metabolites can help discern which agent is the proximate teratogen, which is essential to accurately predicting a test compound's developmental toxicity potential. Additionally, maternal-fetal interactions and organogenesis cannot be modeled using an in vitro model. However, one of the advantages of using an in vitro assay is the ability to separate adverse outcomes due to compound versus outcomes due to maternal toxicity from compound exposure. Developmental toxicity testing in cells derived from human embryos is likely to generate more reliable in vitro prediction endpoints than endpoints currently available through the use of animal models, or other in vitro non-human assays given the physiological relevance of hES cells to human development.

This assay can help reduce or eliminate species-specific misinterpretations, reduce need for a second species, and could be included as part of a panel of in vitro assays aimed at defining where potential adverse responses in human populations may exist. Much like other in vitro culture systems that are used to understand potential for target organ toxicity, this assay can assess potential for developmental toxicity. Part of its strength is that this is accomplished across a range of exposure levels. While there is no defined way to project safety margins or fully predict human response based on in vitro data, assays such as this one can help define exposure ranges where response may be expected as well as those where a response would not be expected to occur. Results could then be incorporated into a panel of tests that in aggregate develop an approximation of clinical safety margins. This information could help to drive decisions as to whether a compound should progress along its development path.

Example 1 has also published as Smith et al., 2013, "Establishment and assessment of a new human embryonic stem cell-based biomarker assay for developmental toxicity screening," *Birth Defects Res B Dev Reprod Toxicol;* 98(4): 343-63, which is hereby incorporated by reference in its entirety.

Example 2

ADMA/Cystine Ratio

With the present invention, it has been determined that the analysis of data obtained from a small number of metabolites can serve as very accurate predictors of teratogenicity. As described in Example 1, an algorithm was developed that evaluated the individual predictive capacity of these secreted features and media components with the training set to identify and confirm several key features that could be used to develop a much simplified predictive model. The selection process weighted the predictive capacity of a feature, overall intensity, and peak shape to identify very well behaved features/metabolites that could be measured by targeted LC-MS or even by other detection systems. Several pairs of features and some individual features were identified that could accurately identify at least 90% of the teratogens and non-teratogens in the training and test sets that were used for the development of the devTOX computational models.

In this example, cystine and asymmetric dimethylarginine (ADMA) were selected for the simplified predictive model due to their abundance, ideal peak shapes, and their exhibition of similar performance metrics as the computational model (Table 14) with both showing an accuracy of 93%. This simplified model is based on a ratio of the reference treatment (DMSO) normalized values of ADMA and cystine. This simple ratio is able to differentiate teratogens that generally exhibit a decrease in the ratio relative to non-teratogens. When evaluated across 9 independent replications of the training set it is clearly able to differentiate teratogens from non-teratogens (FIG. 9), using a criteria of ratios less than 0.9 indicates teratogenicity.

Figure 9:
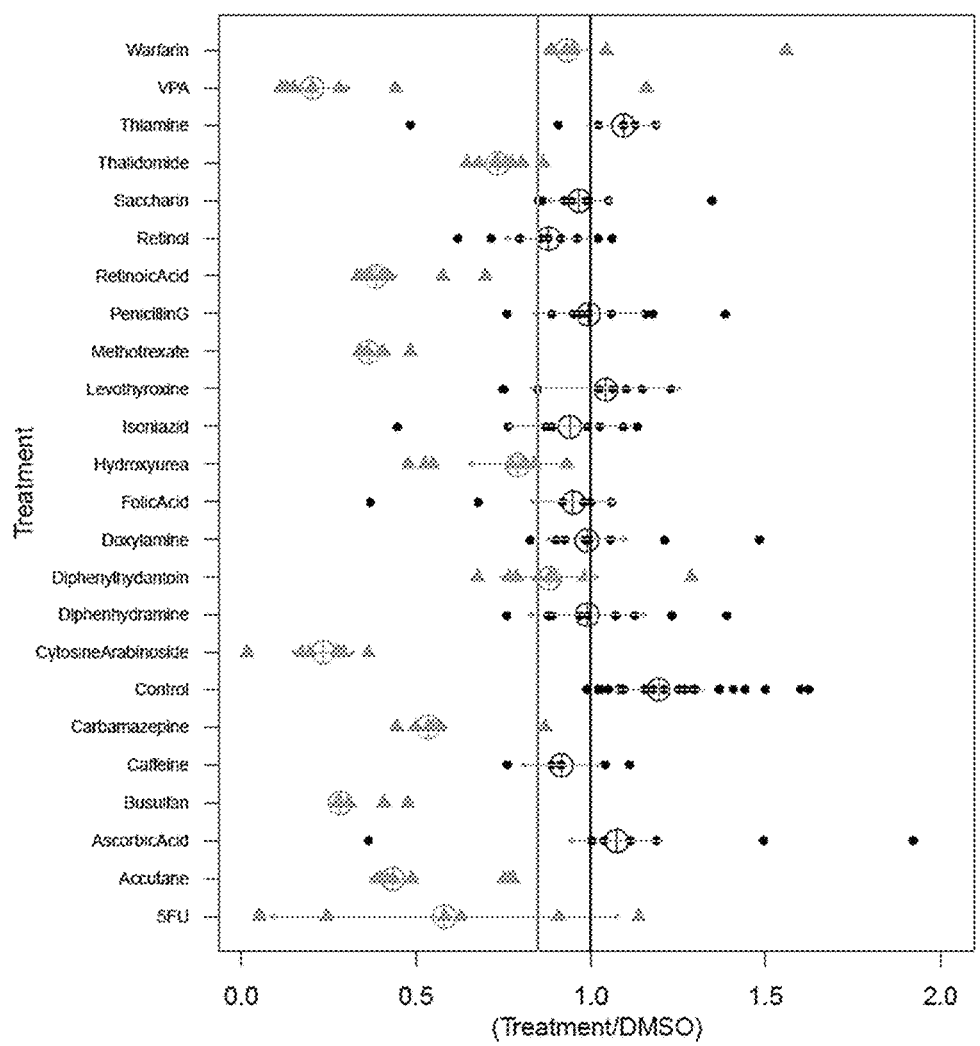
FIG. 9 shows the ratio of the reference treatment normalized ratio of ADMA and cystine for each training set agent.

FIG. 9 shows the ratio of the reference treatment normalized ratio of ADMA (secreted metabolite) and cystine (media constitute) for each training set agent. The X-axis is the reference normalized ratio of ADMA/Cystine. The y-axis is the training set of pharmaceuticals. Grey color with triangle glyphs represents teratogens and black color with circle glyphs represents non-teratogens. Each glyph point represents the media value of an independent experimental block (6 reps per block). The crosshair glyphs mark the sample medians. In FIG. 9, grey vertical line is threshold of teratogenicity, grey horizontal lines are the median absolute deviations, and black vertical line designates 1.0. The arrows at the bottom indicate the values used for differentiation of teratogens and nonteratogens, utilizing a cut off of 0.9 (grey line).

TABLE 12

Comparison of validation and test set model predictions.

| Treatment Metadata | | Model Predictions | | |
|---|---|---|---|---|
| Treatment | Dose | Known Effect | Version 2.0 | Version 2.1 | ADMA/Cystine |
| *Amoxicillin* | 20.5 | Non | Non | Non | Non |
| Ascorbic Acid | 90 | Non | Non | Non | Non |
| Caffeine | 9.3 | Non | Non | Non | Ter |
| Diphenhydramine | 0.25 | Non | Non | Non | Non |
| Doxylamine | 0.38 | Non | Non | Non | Non |
| FolicAcid | 0.035 | Non | Ter | Non | Non |
| Isoniazid | 51 | Non | Ter | Ter | Non |
| Levothyroxine | 0.14 | Non | Ter | Non | Non |
| *Metoclopramide* | 0.15 | Non | Ter | Non | Non |
| Penicillin G | 134.6 | Non | Non | Non | Non |
| Retinol | 2.4 | Non | Ter | Non | Non |
| Saccharin | 1.4 | Non | Non | Non | Non |
| Thiamine | 0.67 | Non | Non | Non | Non |
| 5FU | 2.7 | Ter | Ter | Ter | Ter |
| Accutane | 2.9 | Ter | Ter | Ter | Ter |
| *Acrolein* | 100 | Ter | Ter | Ter | Ter |
| *Aminopterin* | 0.008 | Ter | Ter | Ter | Ter |
| Busulfan | 5.3 | Ter | Ter | Ter | Ter |
| Carbamazepine | 47 | Ter | Ter | Ter | Ter |
| Cytosine Arabinoside | 0.13 | Ter | Ter | Ter | Ter |
| Diphenylhydantoin | 79.3 | Ter | Non | Non | Non |
| Hydroxyurea | 118.5 | Ter | Ter | Ter | Ter |
| Methotrexate | 0.04 | Ter | Ter | Ter | Ter |
| Retinoic Acid | 1.2 | Ter | Ter | Ter | Ter |
| Thalidomide | 12.4 | Ter | Ter | Ter | Ter |

TABLE 12-continued

Comparison of validation and test set model predictions.

| Treatment Metadata | | Model Predictions | | |
|---|---|---|---|---|
| Treatment | Dose | Known Effect | Version 2.0 | Version 2.1 | ADMA/Cystine |
| VPA | 1000 | Ter | Ter | Ter | Ter |
| Warfarin | 23.4 | Ter | Ter | Ter | Ter |

Treatments not included in the training set marked with an asterisk and italic.
Ter = Teratogen,
Non = Non-teratogen.

Example 3

Cystathionine/Cystine Ratio

Figure 10:
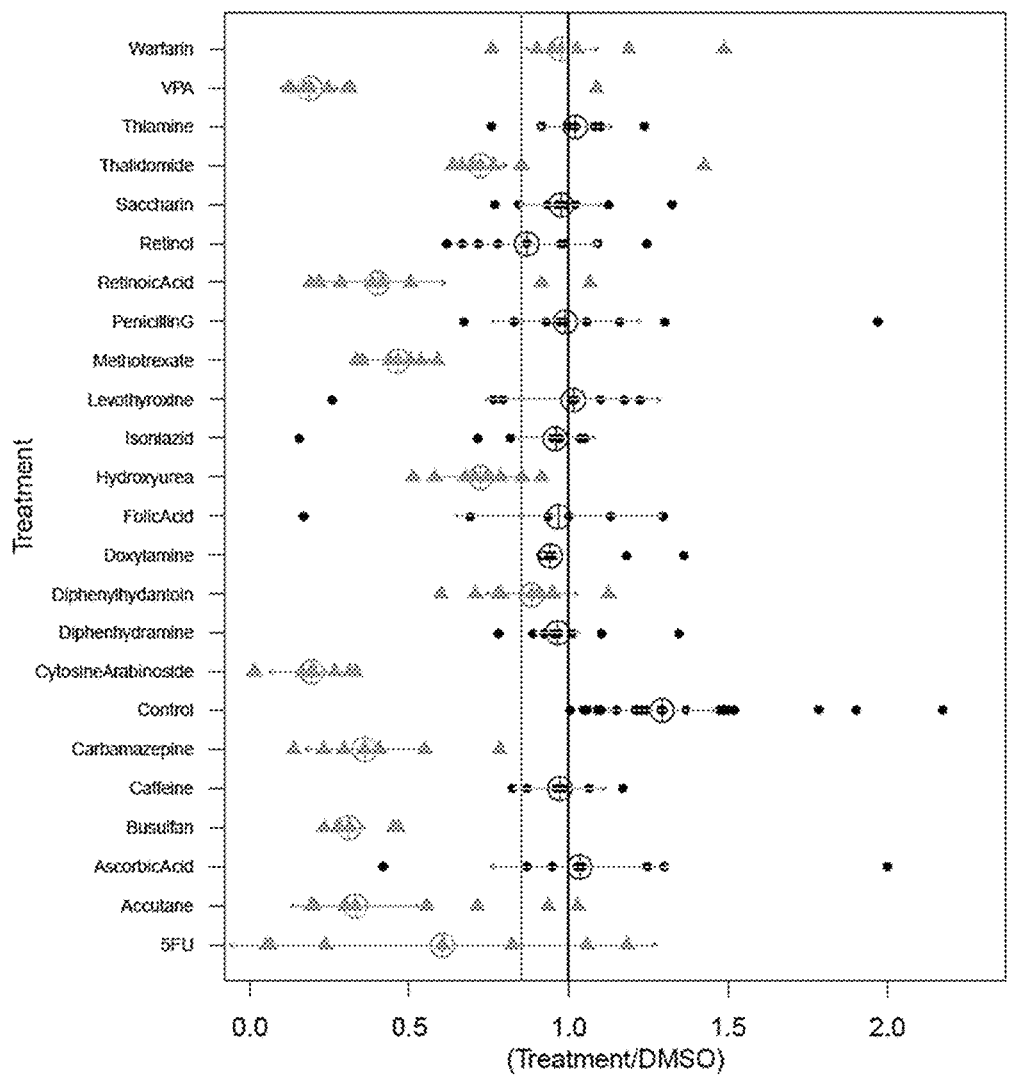
FIG. 10 shows the ratio of the reference treatment normalized ratio of cystathionine and cystine for each training set agent.

Following procedures as described in the previous examples, it was also determined the determination of cystathionine/cystine fold change ratios also provide excellent predictivity and general performance in the rapid teratogenicity screen described herein. This is shown in FIG. 10. In FIG. 10, grey color with triangle glyphs represents teratogens, black color with circle glyphs represents non-teratogens, grey vertical line is threshold of teratogenicity, crosshair glyphs mark the sample medians, grey horizontal line is the median absolute deviations, and black vertical line designates 1.0.

Example 4

Viability Analysis

Changes in cellular metabolism as measured in the spent medium following cell culture (the secretome) is a functional measure of cell health. The cell culture "secretome" refers to the metabolites present in the spent media or cell culture supernatant following cell culture. The secretome is comprised of media components, metabolites passively and actively transported across the plasma membrane, intracellular metabolites release upon lysis, and those produced through extracellular metabolism of enzymes. The change in secretome elicited by an experimental agent relative to untreated cultures produces a metabolic signature that can be used to infer the number of metabolically viable cells present within a cell culture. We have identified a number of secreted metabolites that can be utilized to infer the number viable cells relative to the number of cells in a reference culture "control group". We compared a number of secreted metabolites to the results of viability analysis performed using a commercial kit and discovered that a decrease in the relative abundance of the secreted metabolites are directly correlated with measurements of cell viability with a Pearson correlation coefficient greater than 0.86 (P value<<0.001) when cytotoxicity is observed in at least the two highest concentrations of a 9 point concentration curve. These metabolites could be utilized by LC-MS or kit based detection to determine the number of viable cells within a cell culture without a requirement to destroy or impact the cells. These metabolites can be used as novel measure of viability that does not require disrupting the growing cells.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. All headings are for the convenience of the reader and should not be used to limit the meaning of the text that follows the heading, unless so specified. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of screening the teratogenicity of a test compound, the method comprising:
    providing a test compound;
    culturing undifferentiated human stem cell-like cells (hSLCs) in the presence of the test compound and in the absence of the test compound, wherein hSLCs are selected from the group consisting of human embryonic stem cells (hESCs), human induced pluripotent (iPS) cells, human embryoid bodies, and hSLC-derived lineage-specific cells;
    determining the fold change in ornithine, or fragment, adduct, deduct or loss thereof, in the culture media of undifferentiated hSLCs cultured in the presence of the test compound in comparison with hSLCs cultured in the absence of the test compound;
    determining the fold change in cystine, or fragment, adduct, deduct or loss thereof, in the culture media of undifferentiated hSLCs cultured in the presence of the test compound in comparison with hSLCs cultured in the absence of the test compound; and
    determining the ratio of the fold change in ornithine, or fragment, adduct, deduct or loss thereof, to the fold change in cystine, or fragment, adduct, deduct or loss thereof, wherein a ratio of less than or equal to 0.88 is indicative of the teratogenicity of the compound, and a ratio of greater than 0.88 is indicative of the non-teratogenicity of the compound.

2. The method of claim 1, wherein the cystine, or fragment, adduct, deduct or loss thereof, and/or ornithine, or fragment, adduct, deduct or loss thereof, are identified using a physical separation method.

3. The method of claim 2, wherein the physical separation method comprises mass spectrometry.

4. The method of claim 3, wherein the mass spectrometry comprises liquid chromatography/electrospray ionization mass spectrometry.

5. The method of claim 1, wherein the cystine, or fragment, adduct, deduct or loss thereof, and/or ornithine, or fragment, adduct, deduct or loss thereof, are measured using a colorimetric or immunological assay.

6. The method of claim 1, wherein the hSLCs are cultured in a range of concentrations of the test compound.

7. The method of claim 6, wherein the range of concentrations comprises a serial dilution.

8. The method of claim 6, wherein the range of concentrations comprises nine three-fold dilutions.

9. The method of claim 6, wherein the range of concentrations is selected from about 0.04 pM to about 300 pM, about 4µM to about 30,000 µM, and about 0.0001 µM to about 10 µM.

10. The method of claim 6, wherein the range of concentrations of the test compound comprises the test compound's human therapeutic $C_{max}$.

11. The method of claim 1, wherein the hSLCs are cultured at a concentration of the test compound comprising the test compound's human therapeutic $C_{max}$.

12. The method of claim 1, further comprising detecting one or more additional metabolites associated with hSLCs cultured in the presence of the test compound in comparison with hSLCs cultured in the absence of the test compound, wherein the one or more additional metabolite comprises arginine, asymmetric dimethylarginine (ADMA), cystathionine, cystine, and/or a fragment, adduct, deduct or loss thereof.

13. The method of claim 12, further comprising determining the ratio of the fold change in arginine, or fragment, adduct, deduct or loss thereof, to the fold change in ADMA, or fragment, adduct, deduct or loss thereof.

14. The method of claim 12, further comprising determining the ratio of the fold change in ADMA, or fragment, adduct, deduct or loss thereof, to the fold change in cystine, or fragment, adduct, deduct or loss thereof.

15. The method of claim 12, further comprising determining the ratio of the fold change in cystathionine, or fragment, adduct, deduct or loss thereof, to the fold change in cystine, or fragment, adduct, deduct or loss thereof.

* * * * *